United States Patent
Hornstein et al.

(10) Patent No.: US 9,499,793 B2
(45) Date of Patent: Nov. 22, 2016

(54) DOWNREGULATION OF MIR-7 FOR PROMOTION OF BETA CELL DIFFERENTIATION AND INSULIN PRODUCTION

(75) Inventors: Eran Hornstein, Rehovot (IL); Sharon Kredo-Russo, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

(21) Appl. No.: 14/237,930

(22) PCT Filed: Aug. 9, 2012

(86) PCT No.: PCT/IL2012/050306
§ 371 (c)(1),
(2), (4) Date: Feb. 10, 2014

(87) PCT Pub. No.: WO2013/021389
PCT Pub. Date: Feb. 14, 2013

(65) Prior Publication Data
US 2014/0212395 A1    Jul. 31, 2014

Related U.S. Application Data

(60) Provisional application No. 61/521,411, filed on Aug. 9, 2011.

(51) Int. Cl.
| | | |
|---|---|---|
| *C12N 15/11* | (2006.01) | |
| *C12N 5/0775* | (2010.01) | |
| *A61K 31/7088* | (2006.01) | |
| *C12N 5/071* | (2010.01) | |
| *C12N 15/113* | (2010.01) | |
| *A61K 35/39* | (2015.01) | |

(52) U.S. Cl.
CPC ......... *C12N 5/0675* (2013.01); *A61K 31/7088* (2013.01); *A61K 35/39* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *C12N 5/0676* (2013.01); *C12N 15/113* (2013.01); *C12N 2310/14* (2013.01); *C12N 2310/141* (2013.01); *C12N 2320/11* (2013.01); *C12N 2501/65* (2013.01)

(58) Field of Classification Search
None
See application file for complete search history.

(56) References Cited

FOREIGN PATENT DOCUMENTS

| WO | WO 2009/067644 | 5/2009 |
|---|---|---|
| WO | WO 2013/021389 | 2/2013 |

OTHER PUBLICATIONS

Melkman-Zehavi et al, miRNAs control insulin content in pancreatic b-cells via downregulation of transcriptional repressors, published online on Feb. 1, 2011, The EMBO Journal, 30: 835-845.*
Russ et al, Insulin-Producing Cells Generated from Dedifferentiated Human Pancreatic Beta Cells Expanded In Vitro, Sep. 30, 2011, PLoS One, vol. 6, issue 9, e25566: 1-12.*
Communication Relating to the Results of the Partial International Search Dated Dec. 5, 2012 From the International Searching Authority Re. Application No. PCT/IL2012/050306.
International Search Report and the Written Opinion Dated Feb. 13, 2013 From the International Searching Authority Re. Application No. PCT/IL2012/050306.
Bravo-Egana et al. "Quantitative Differential Expression Analysis Reveals MiR-7 as Major Islet MicroRNA", Biochemical and Biophysical Research Communications, 366: 922-926, 2008.
Correa-Medina et al. "MicroRNA MiR-7 is Preferentially Expressed in Endocrine Cells of the Developing and Adult Human Pancreas", Gene Expression Patterns, XP026002084, 9(4): 193-199, Apr. 1, 2009. p. 195, Line 1—p. 197.
Czech "MicroRNAs as Therapeutic Targets", The New England Journal of Medicine, XP002532649, 354(11): 1194-1195, Mar. 16, 2006.
Joglekar et al. "Expression of Islet-Specific MicroRNAs During Human Pancreatic Development", Gene Expression Patterns, XP025769796, 9(2): 109-113, Feb. 1, 2009. Figs.1, 3.
Lynn et al. "MicroRNA Expression is Required for Pancreatic Islet Cell Genesis in the Mouse", Diabetes, 56: 2938-2945, 2007.
Melkman-Zehavi et al. "MiRNAs Control Insulin Content in Pancreatic Beta-Cells Via Downregulation of Transcriptional Repressors", The EMBO Journal, 30(5): 835-845, 2011.
Poy et al. "MiR-375 Maintains Normal Pancreatic Alpha- and Beta-Cell Mass", Proc. Natl. Acad. Sci. USA, PNAS, 106(14): 5813-5818, Apr. 7, 2009.
Scherr et al. "Lentivirus-Mediated Antagomir Expression for Specific Inhibition of MiRNA Function", Nucleic Acids Research, XP002492839, 35(22): E149-1-E149-9, Jan. 1, 2007. p. 149.
Notice of Reason for Refusal Dated Apr. 27, 2016 From the Japanese Patent Office Re. Application No. 2014-524486 and Its Translation Into English.

* cited by examiner

Primary Examiner — Tracy Vivlemore
Assistant Examiner — Kate Poliakova-Georgantas

(57) ABSTRACT

A method of ex-vivo increasing insulin content in beta cells or stem cells is disclosed. The method comprising contacting the beta cells or stem cells with an agent for downregulating an activity or expression of miR-7, thereby increasing the insulin content in the beta cells or stem cells.

15 Claims, 25 Drawing Sheets
(23 of 25 Drawing Sheet(s) Filed in Color)

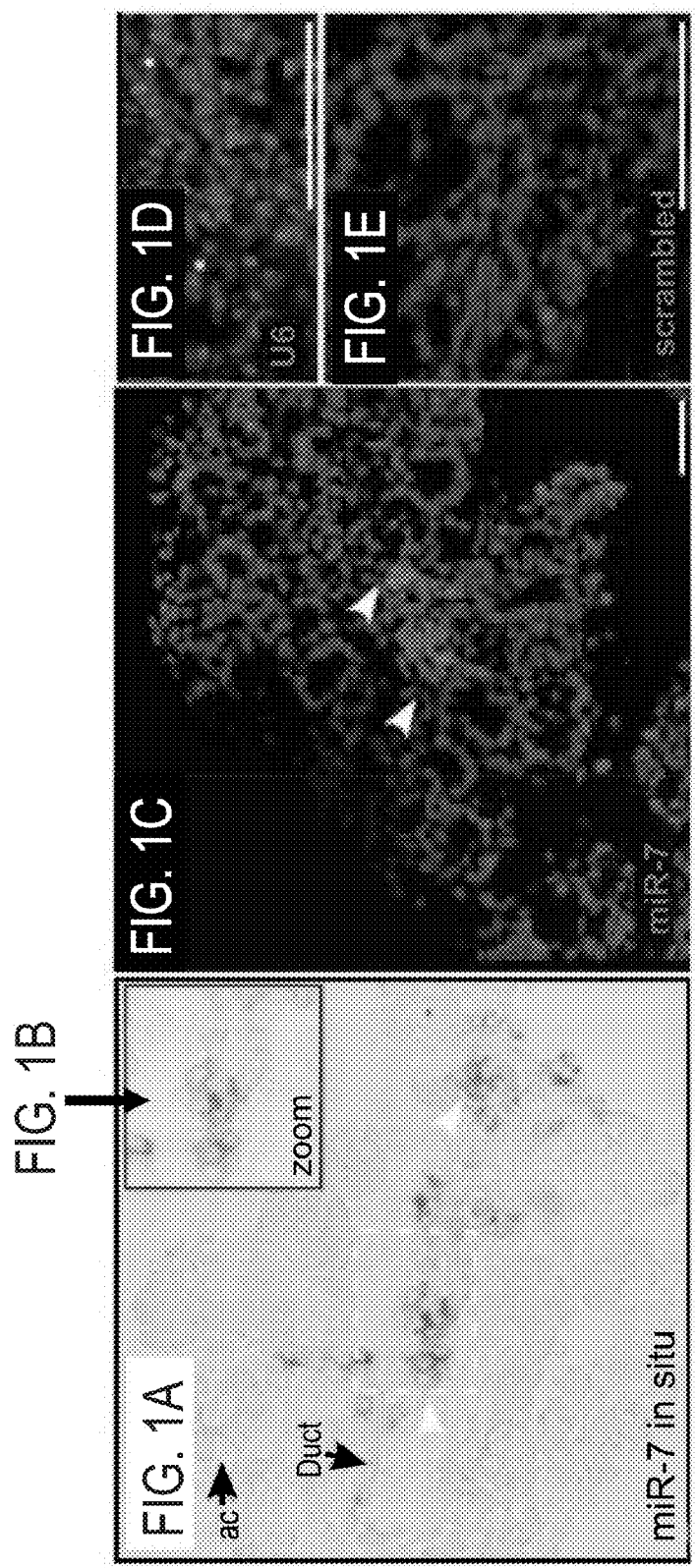

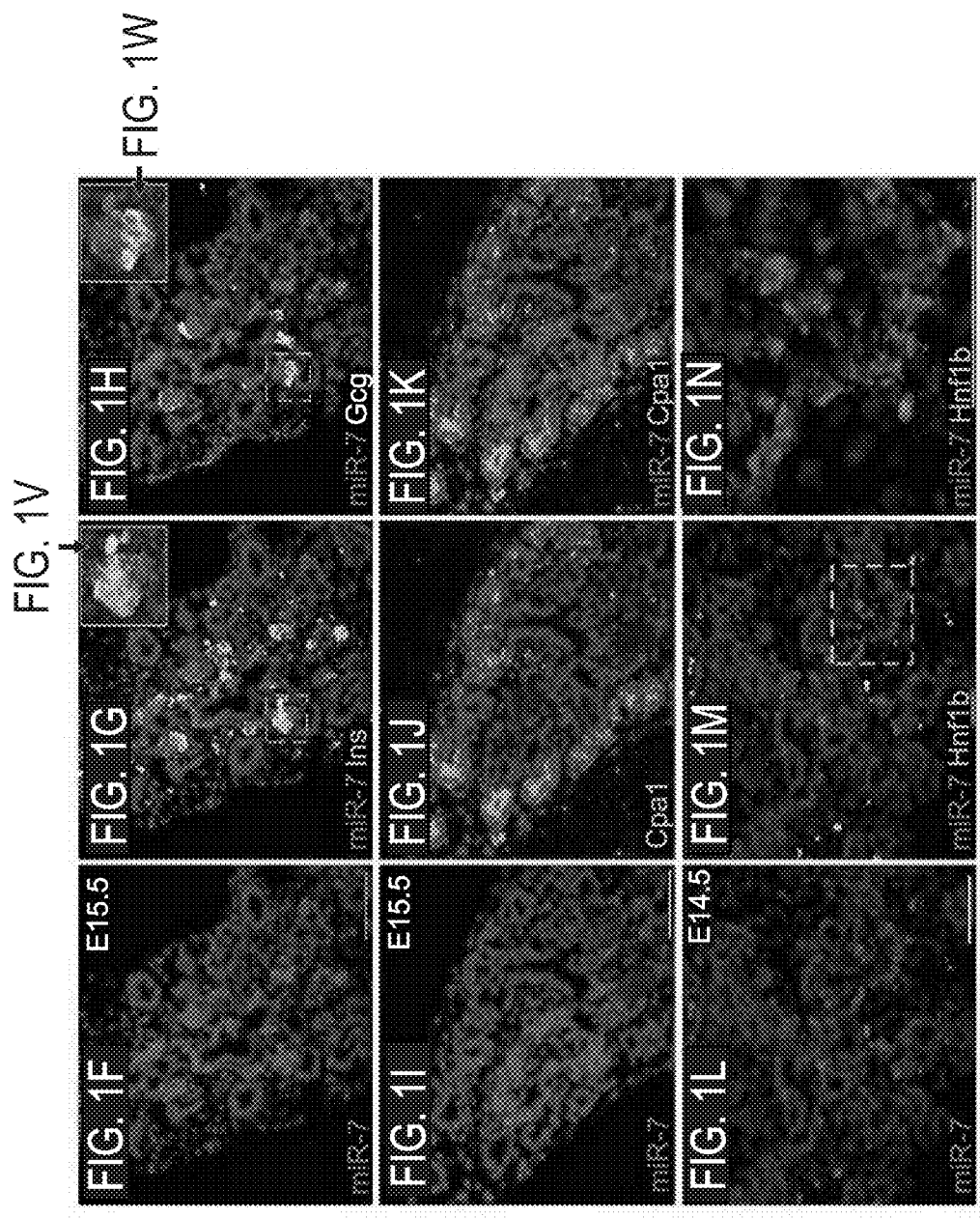

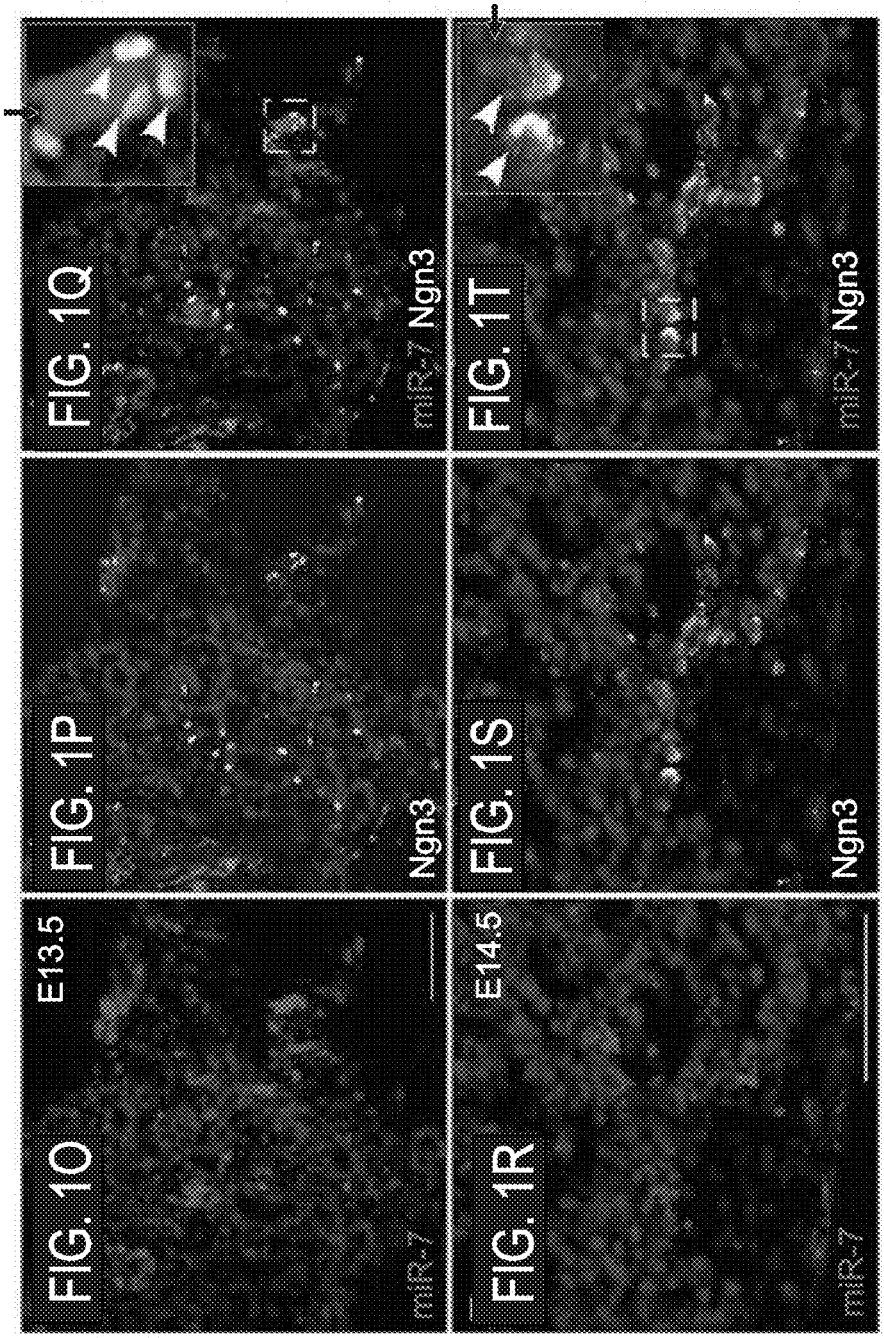

Predicted miR-7 targets (conserved)

Gene ontology analysis

"Regulation of transcription"

Pancreatic transcription factors within this list

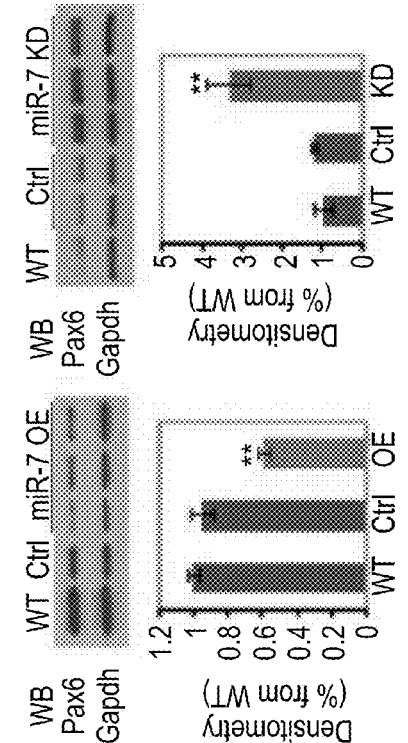
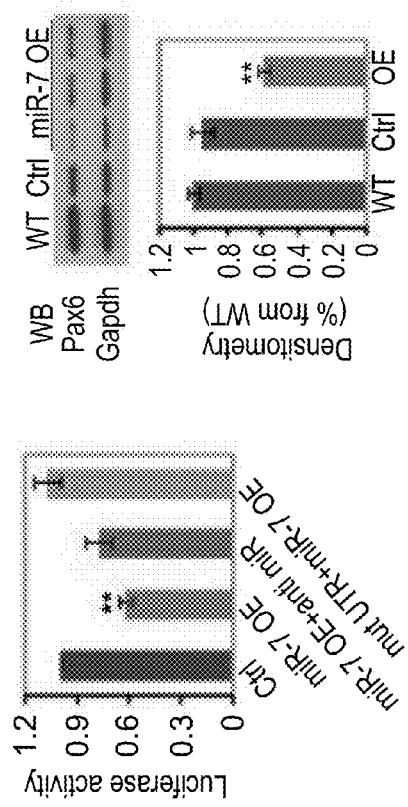

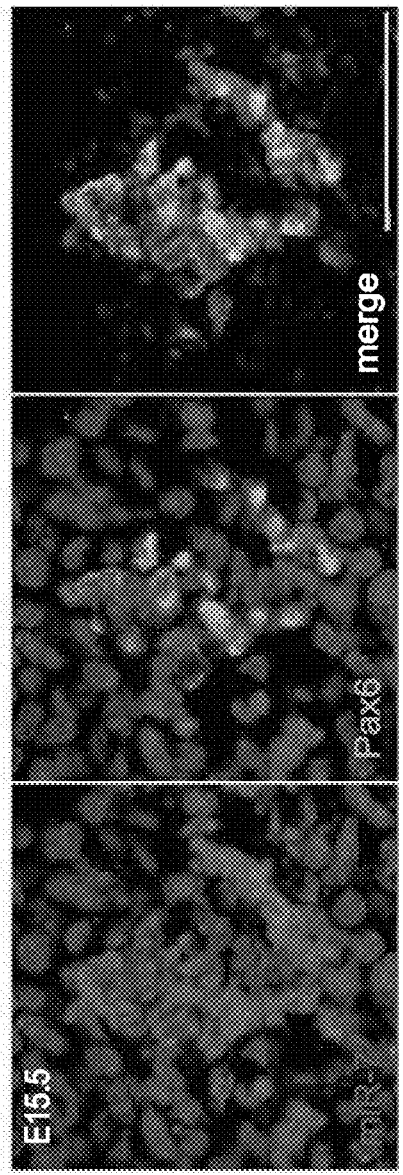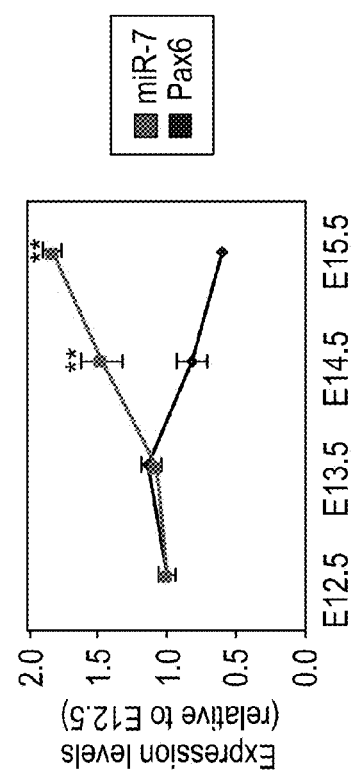

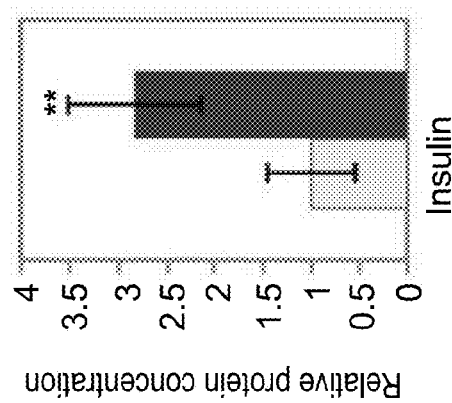
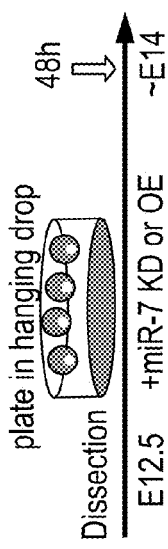
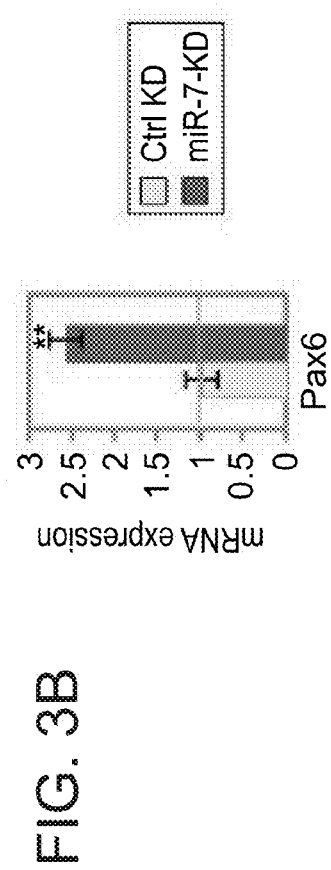
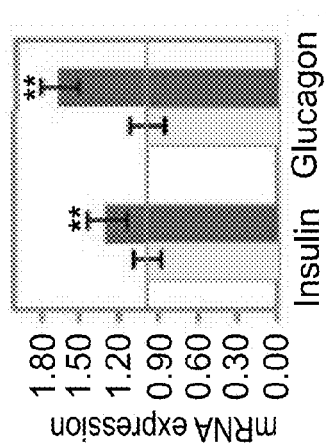
FIG. 3A
FIG. 3B
FIG. 3C
FIG. 3D

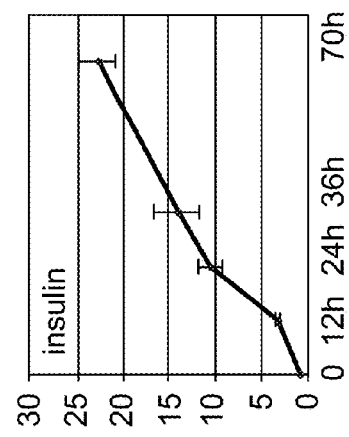
FIG. 4A
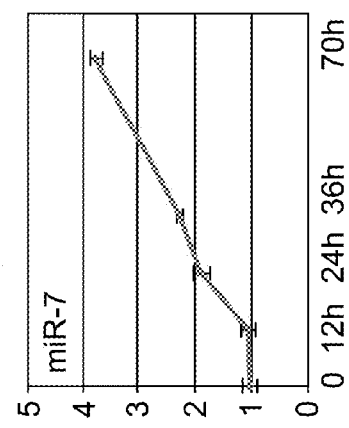
FIG. 4B
FIG. 4C
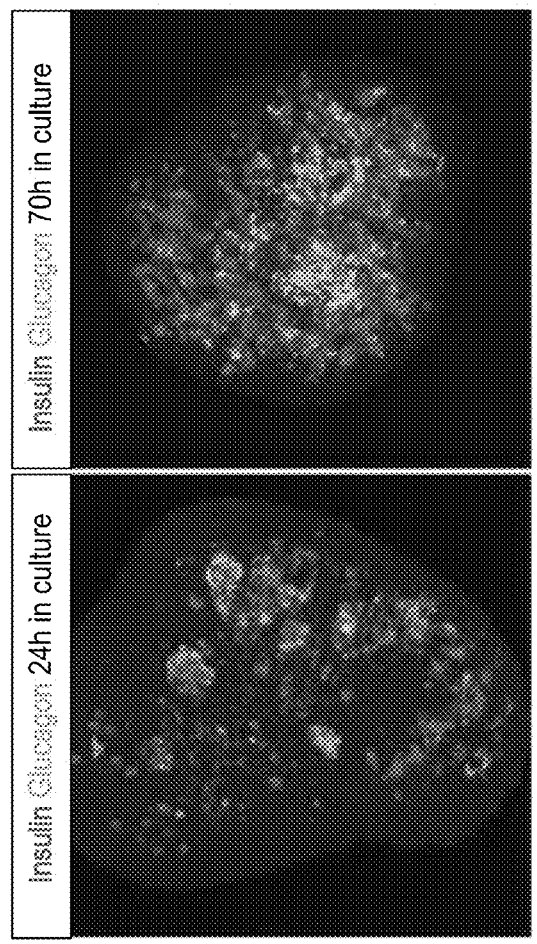
FIG. 4D
FIG. 4E

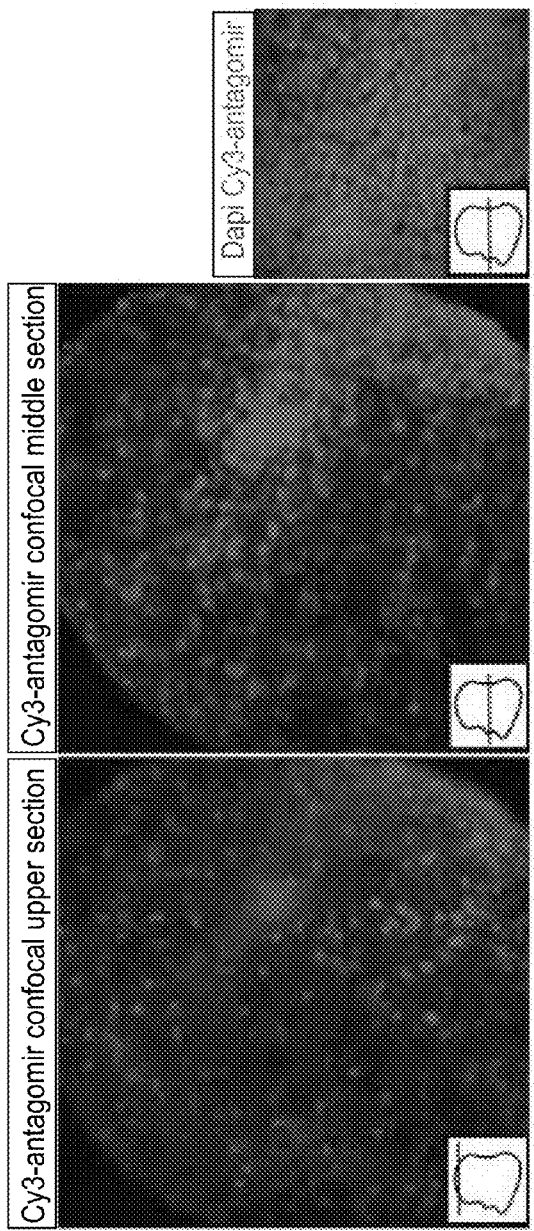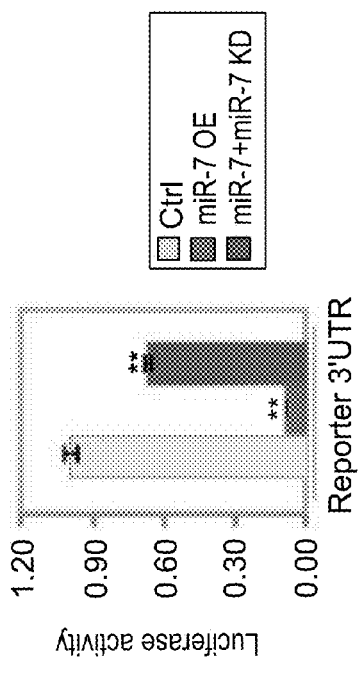

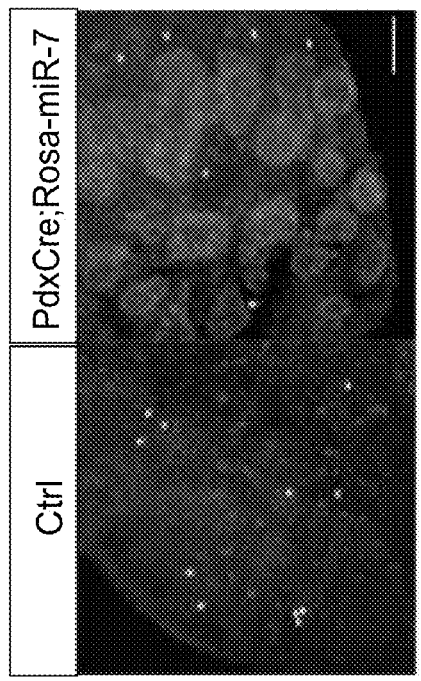
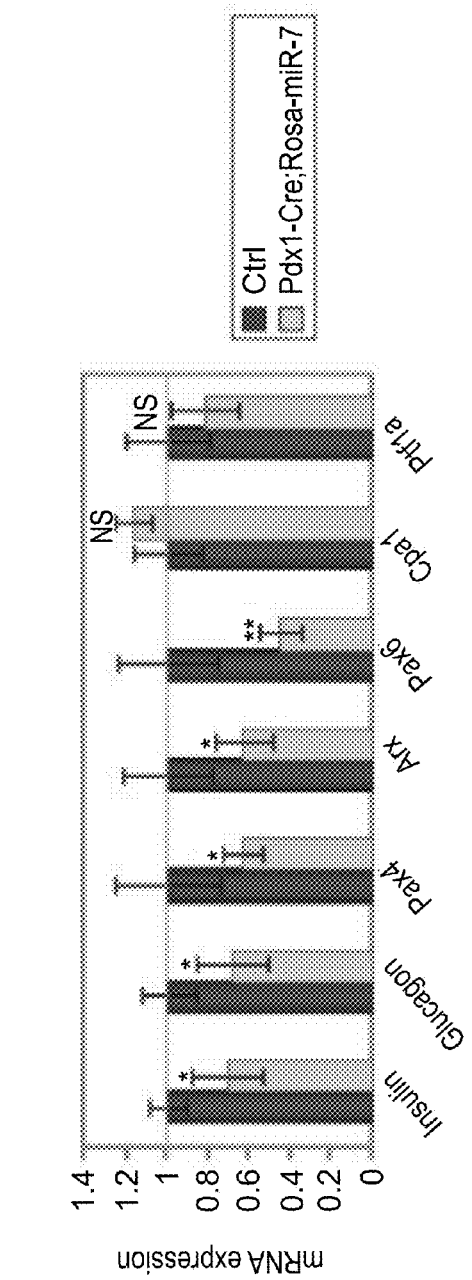
FIG. 5D    FIG. 5E
FIG. 5F

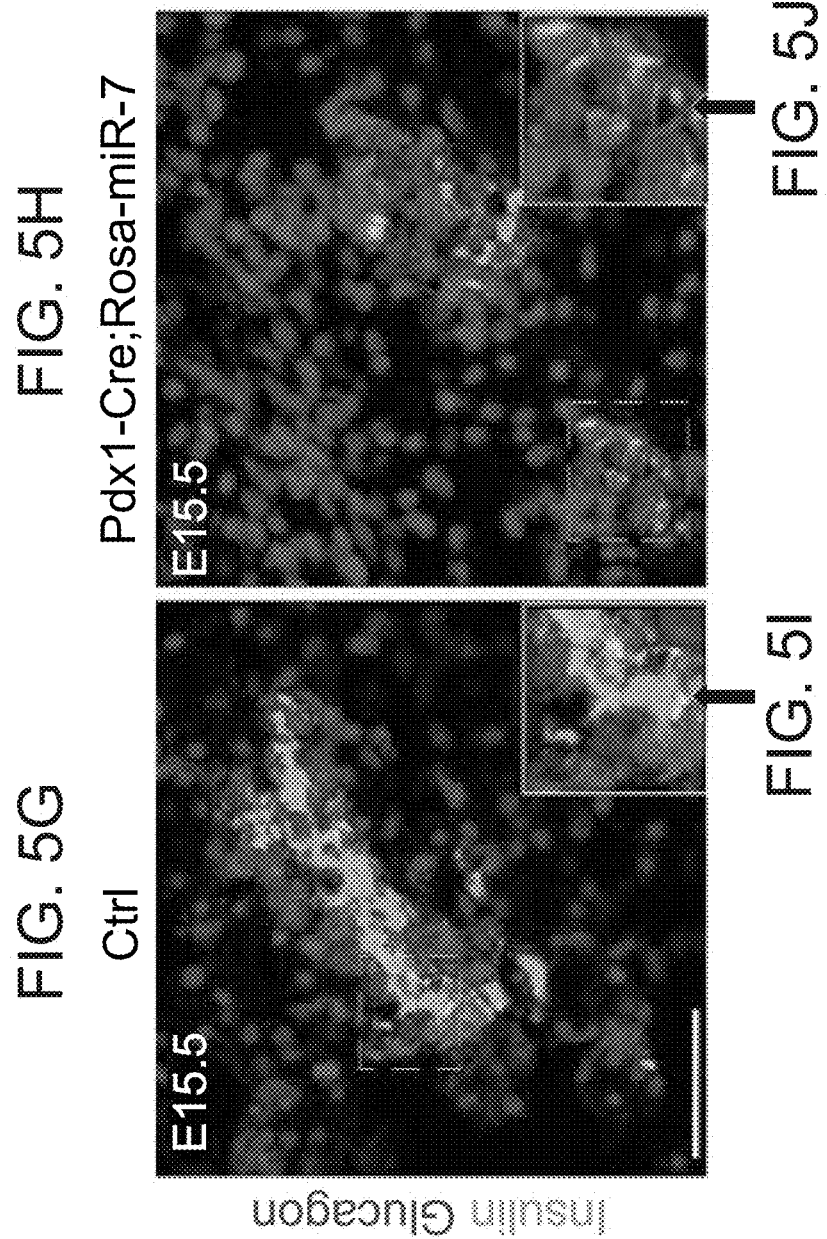

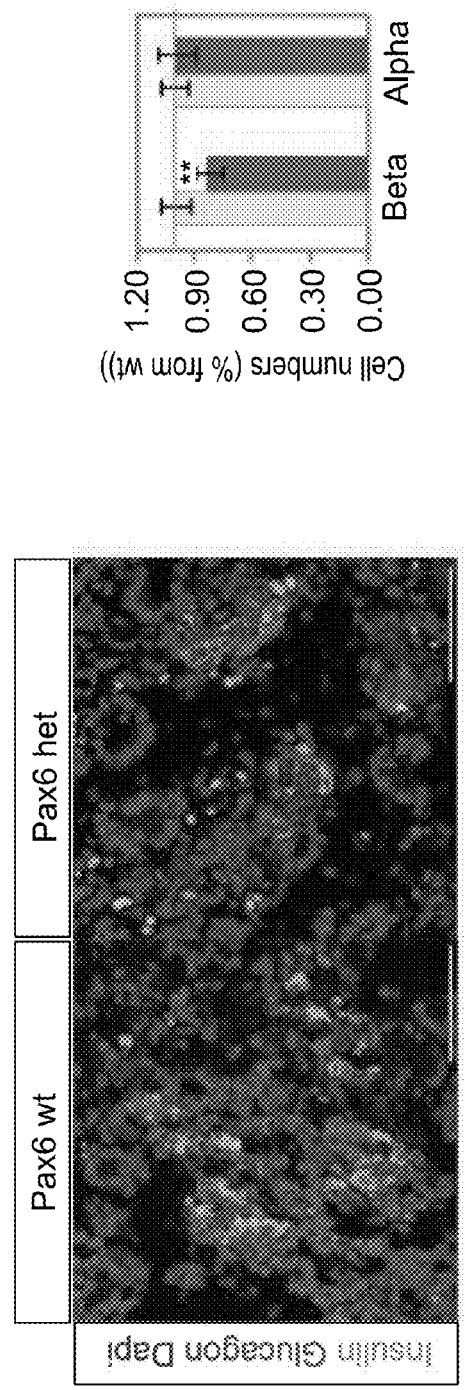
FIG. 6F, FIG. 6G, FIG. 6H, FIG. 6I, FIG. 6J

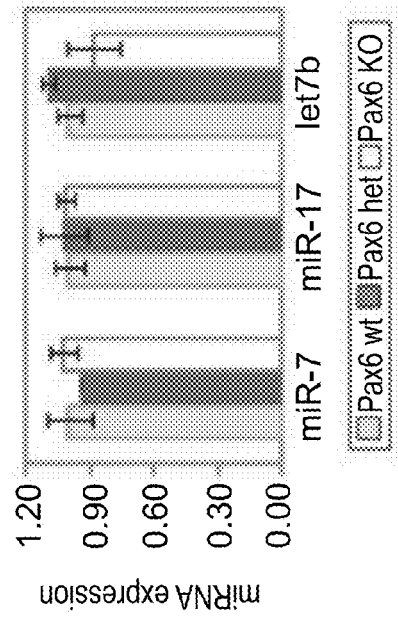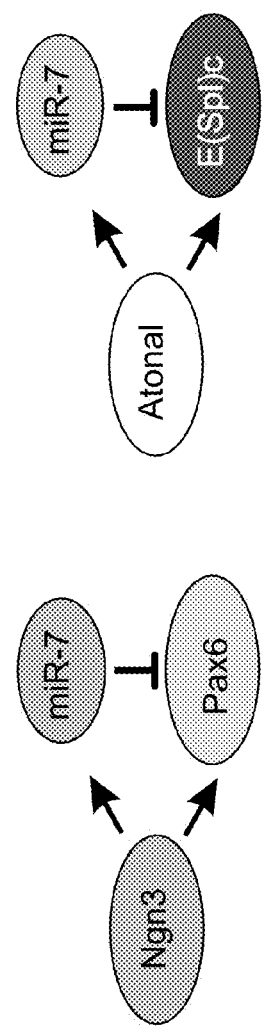
FIG. 7A  FIG. 7B  FIG. 7C

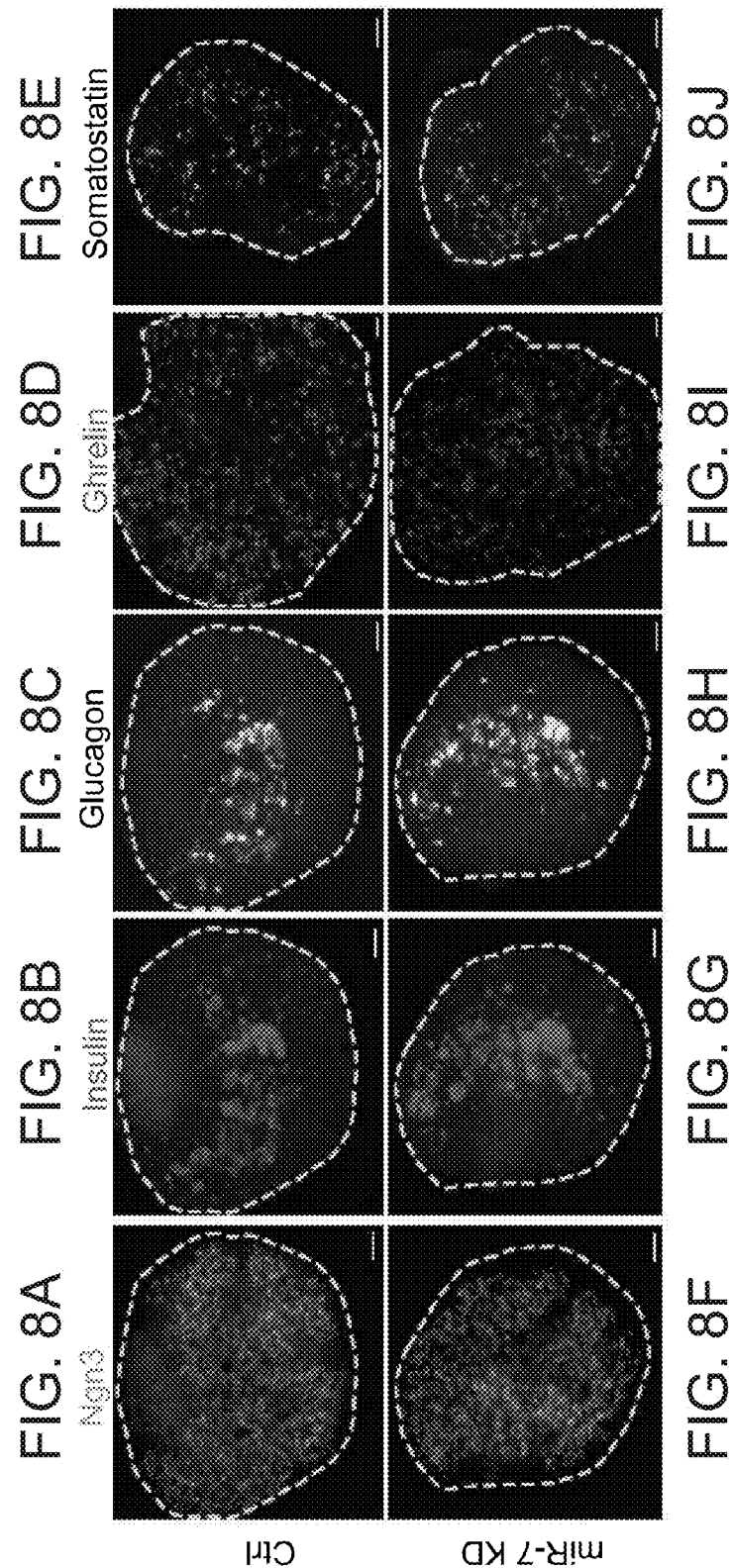

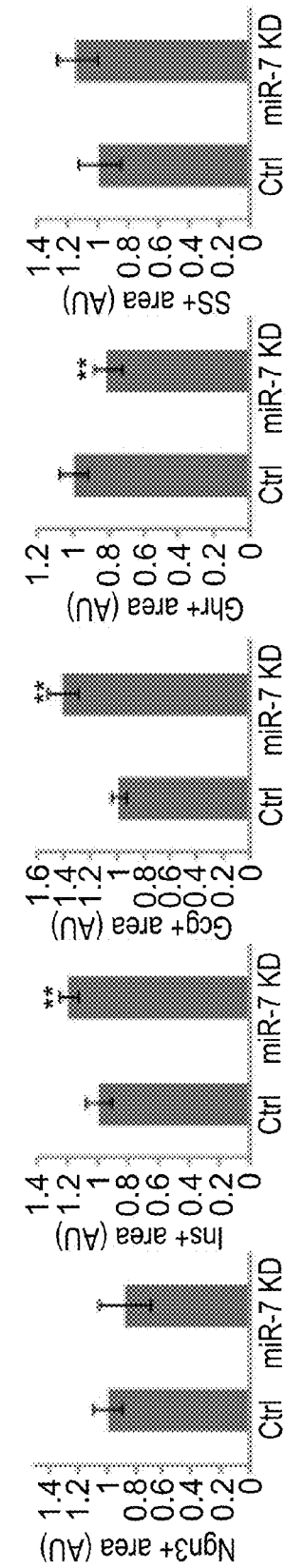
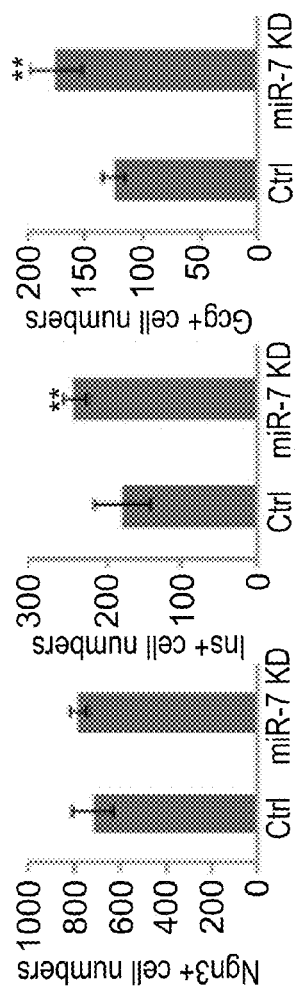
FIG. 8K FIG. 8L FIG. 8M FIG. 8N FIG. 8O
FIG. 8P FIG. 8Q FIG. 8R FIG. 8S

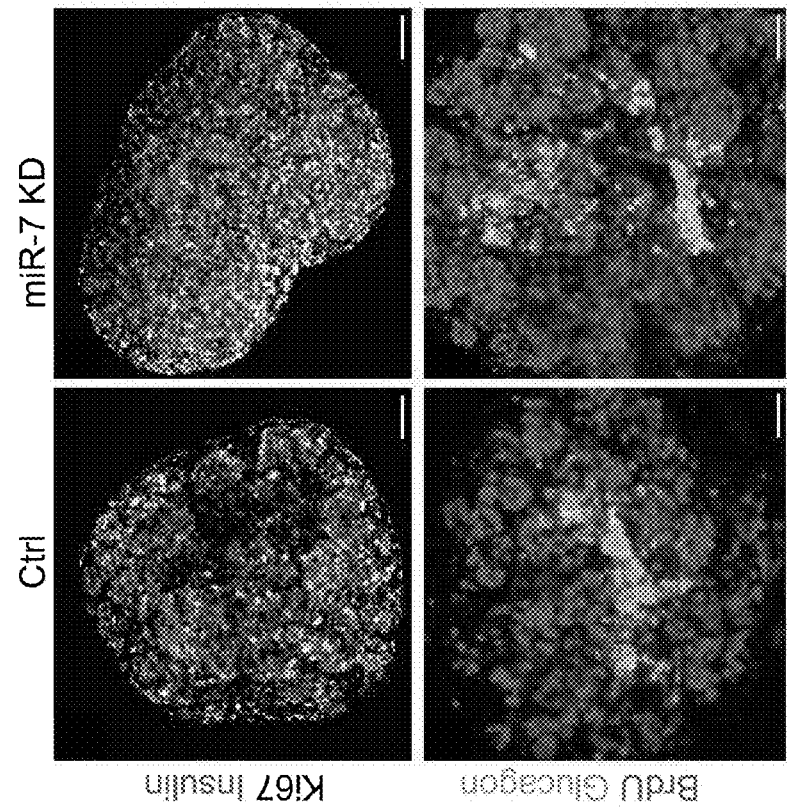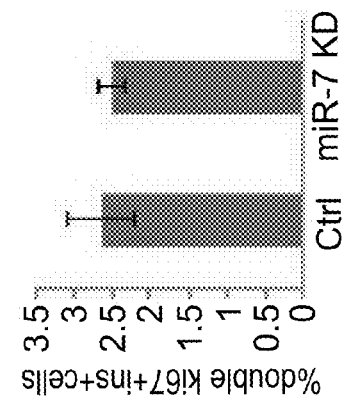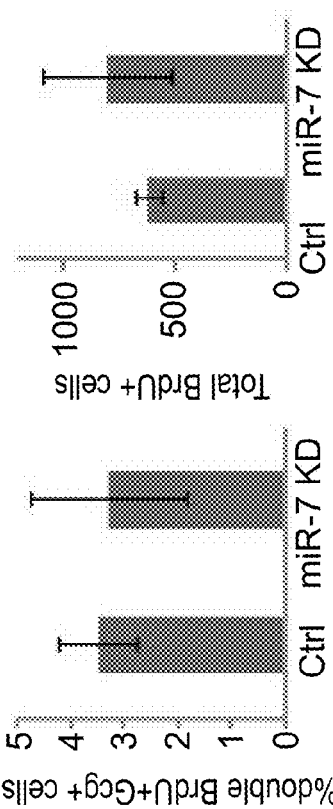

US 9,499,793 B2

DOWNREGULATION OF MIR-7 FOR PROMOTION OF BETA CELL DIFFERENTIATION AND INSULIN PRODUCTION

RELATED APPLICATIONS

This application is a National Phase of PCT Patent Application No. PCT/IL2012/050306 having International filing date of Aug. 9, 2012, which claims the benefit of priority under 35 USC §119(e) of U.S. Provisional Patent Application No. 61/521,411 filed on Aug. 9, 2011. The contents of the above applications are all incorporated by reference as if fully set forth herein in their entirety.

SEQUENCE LISTING STATEMENT

The ASCII file, entitled 58346SequenceListing.txt, created on Jan. 6, 2014, comprising 196,383 bytes, submitted concurrently with the filing of this application is incorporated herein by reference.

FIELD AND BACKGROUND OF THE INVENTION

The present invention, in some embodiments thereof, relates to downregulation of microRNA-7 and, more particularly, but not exclusively, to the use of same for promoting insulin production from pancreatic beta cells.

The development of the endocrine pancreas is governed by a network of transcription factors that specify the different endocrine cell types, including insulin-producing beta cells, glucagon-producing alpha cells, delta cells (somatostatin producing cells), PP cells (pancreatic peptide producing cells) and epsilon cells (ghrelin producing cells). The transcription factor Neurogenin3 (Ngn3) initiates the endocrine differentiation program and then a complex network of transcription factors is activated to differentially specify the endocrine lineages.

Pax6 is one such transcription factor acting downstream of Ngn3. Pax6 is pivotal in the differentiation of pancreatic beta-cells and alpha-cells, as islet morphogenesis has been shown to be disrupted when Pax6 expression is attenuated. In both humans and mice, two Pax6 alleles are required in order to maintain glucose homeostasis and loss of one allele results in glucose intolerance. The development of multiple other organs is sensitive to Pax6 haplo-insufficiency, including the iris and the lens. Normal embryonic development cannot tolerate high levels of Pax6. Thus, for example, Pax6 overexpression in mice causes eye abnormalities and induces apoptosis in the brain and the endocrine pancreas. Thus, it appears that Pax6 expression is tightly controlled to ensure appropriate levels of expression.

Genome-encoded miRNAs bind to specific sites on the 3' untranslated region (3'UTR) of their target mRNAs, to impart posttranscriptional silencing. This regulatory layer acts in concert with transcription factors to refine gene expression and confer robustness to developmental transitions. Total inactivation of miRNA maturation causes pancreas agenesis [Lynn et al. (2007) Diabetes 56(12): 2938-45], indicating that miRNAs are essential for early pancreas development. Melkman-Zehavi et al. disclosed that miRNAs control insulin content in pancreatic beta cells by downregulation of transcriptional repressors, thus allowing reactivation of insulin transcription [Melkman-Zehavi et al. (2011) EMBO Journal 1-11]. Furthermore, specific miRNAs were shown to control insulin synthesis and exocytosis in differentiated cells. For example, loss of function of miR-375 in mice disrupts islet morphogenesis and endocrine cell differentiation [Poy et al., (2009) Proc Natl Acad Sci USA (106) 5813-5818] while specific knockdown of miR-24, miR-26, miR-182 or miR-148 in beta cells downregulates insulin promoter activity and insulin mRNA levels [Melkman-Zehavi et al. (2011), supra].

miR-7 is another miRNA that is highly and specifically expressed in the endocrine pancreas in mice and humans [Bravo-Egana et al. (2008) Biochem Biophys Res Commun (366) 922-926; Correa-Medina et al. (2009) Gene Expr Patterns (9) 193-199]. miR-7 is an evolutionarily conserved miRNA, encoded by three different genomic loci in humans and mice (mouse: mmu-mir-7a-1 at Chr13, mmu-mir-7a-2 at Chr7 and mmu-mir-7b at Chr17). The duplication of the miR-7 gene in vertebrates hampers genetic loss-of-function analysis.

PCT Publication No. WO 2009/067644 (to Pastori Ricardo et al.) discloses that mir-7 is a marker of differentiated endocrine cells and plays a role in β-cell biogenesis. WO 2009/067644 further discloses that inhibition of mir-7 activity in the fetal pancreas results in inhibition of formation of insulin in the fetal pancreas.

SUMMARY OF THE INVENTION

According to an aspect of some embodiments of the present invention there is provided a method of ex-vivo increasing insulin content in beta cells or stem cells, the method comprising contacting the beta cells or stem cells with an agent for downregulating an activity or expression of miR-7, thereby increasing the insulin content in the beta cells or stem cells.

According to an aspect of some embodiments of the present invention there is provided an isolated population of cells generated according to the methods of the present invention.

According to an aspect of some embodiments of the present invention there is provided an isolated population of cells comprising an exogenous agent for downregulating an activity or expression of miR-7, wherein the cells secrete insulin.

According to an aspect of some embodiments of the present invention there is provided a pharmaceutical composition comprising the isolated population of cells and a pharmaceutically acceptable carrier or diluent.

According to an aspect of some embodiments of the present invention there is provided a use of the isolated population of cells for the manufacture of a medicament identified for treating a medical condition associated with an insulin deficiency.

According to an aspect of some embodiments of the present invention there is provided a method of treating a medical condition associated with an insulin deficiency in a subject in need thereof, the method comprising administering to the subject the isolated population of cells, thereby treating the medical condition associated with the insulin deficiency.

According to an aspect of some embodiments of the present invention there is provided a method of treating a medical condition associated with an insulin deficiency in a subject in need thereof, the method comprising administering to the subject an agent for downregulating an activity or expression of miR-7, thereby treating the medical condition associated with the insulin deficiency.

According to an aspect of some embodiments of the present invention there is provided a method of increasing insulin content in beta cells or stem cells, the method comprising expressing in the beta cells or stem cells a target gene of miR-7 selected from the group consisting of epidermal growth factor receptor (EGFR), insulin-degrading enzyme (IDE), Kruppel-like factor 4 (KLF4), GLI family zinc finger 3 (GLI3), insulin receptor substrate 1 (IRS1), Sp1 transcription factor (SP1), O-linked N-acetylglucosamine (GlcNAc) transferase (UDP-N-acetylglucosamine:polypeptide-N-acetylglucosaminyl transferase) (OGT), insulin-like growth factor 1 receptor (IGF1R) and one cut homeobox 2 (ONECUT2), thereby increasing the insulin content in the beta cells or stem cells.

According to an aspect of some embodiments of the present invention there is provided a nucleic acid construct comprising a nucleic acid sequence encoding a target gene of miR-7 selected from the group consisting of epidermal growth factor receptor (EGFR), insulin-degrading enzyme (IDE), Kruppel-like factor 4 (KLF4), GLI family zinc finger 3 (GLI3), insulin receptor substrate 1 (IRS1), Sp1 transcription factor (SP1), O-linked N-acetylglucosamine (GlcNAc) transferase (UDP-N-acetylglucosamine:polypeptide-N-acetylglucosaminyl transferase) (OGT), insulin-like growth factor 1 receptor (IGF1R) and one cut homeobox 2 (ONECUT2) wherein the target gene of miR-7 is under a transcriptional regulation of a cis-acting regulatory element.

According to an aspect of some embodiments of the present invention there is provided an isolated population of beta cells or stem cells exogenously expressing a target gene of miR-7 selected from the group consisting of epidermal growth factor receptor (EGFR), insulin-degrading enzyme (IDE), Kruppel-like factor 4 (KLF4), GLI family zinc finger 3 (GLI3), insulin receptor substrate 1 (IRS1), Sp1 transcription factor (SP1), O-linked N-acetylglucosamine (GlcNAc) transferase (UDP-N-acetylglucosamine:polypeptide-N-acetylglucosaminyl transferase) (OGT), insulin-like growth factor 1 receptor (IGF1R) and one cut homeobox 2 (ONECUT2).

According to some embodiments of the invention, the isolated population of cells is for treating a medical condition associated with an insulin deficiency.

According to some embodiments of the invention, the stem cells comprise embryonic stem cells.

According to some embodiments of the invention, the stem cells comprise human pluripotent stem cells.

According to some embodiments of the invention, the stem cells comprise mesenchymal stem cells.

According to some embodiments of the invention, the beta cells comprise precursor beta cells.

According to some embodiments of the invention, the precursor beta cells comprise de-differentiated beta cells.

According to some embodiments of the invention, the dedifferentiated beta cells comprise induced pluripotent stem cells generated from beta cells.

According to some embodiments of the invention, the precursor beta cells comprise transdifferentiated liver cells.

According to some embodiments of the invention, the beta cells comprise mature beta cells.

According to some embodiments of the invention, the agent is a polynucleotide agent.

According to some embodiments of the invention, the agent is an antagomir.

According to some embodiments of the invention, the medical condition associated with an insulin deficiency comprises diabetes mellitus.

According to some embodiments of the invention, the subject is a human subject.

According to some embodiments of the invention, the method being effected ex-vivo.

According to some embodiments of the invention, the method being effected in-vivo.

According to some embodiments of the invention, the cis-acting regulatory element is a beta cell or stem cell specific promoter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1U:
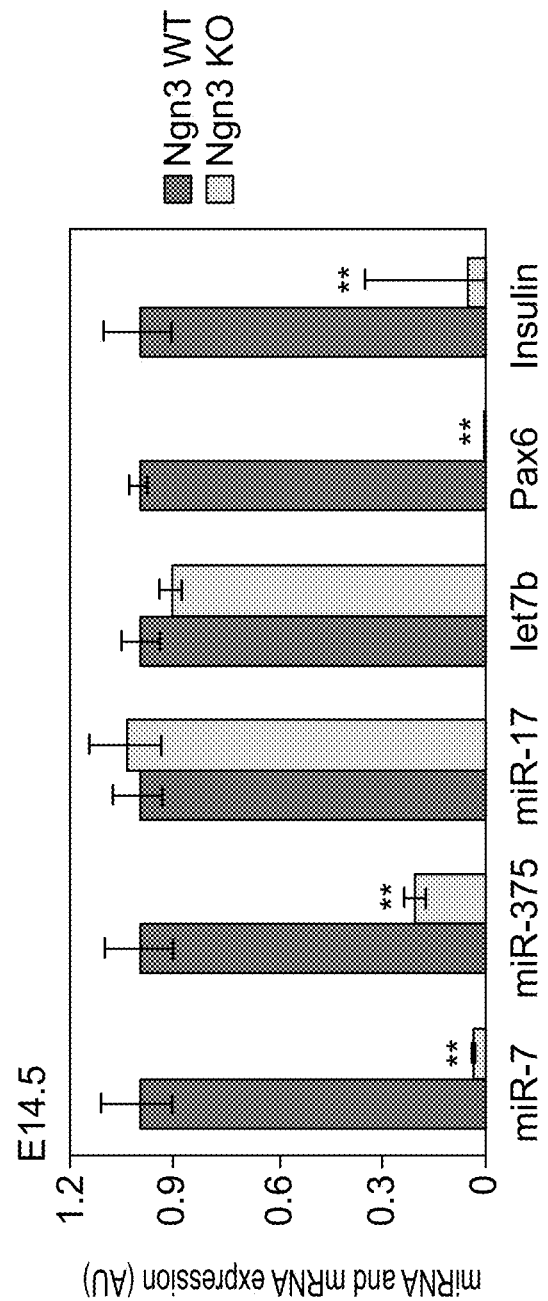

FIGS. 1A-Y depict miR-7 expression in endocrine cells of the pancreas. FIGS. 1A-T and 1V-Y illustrate miR-7 fluorescent in situ hybridization combined with protein immunofluorescence analysis of E13.5-E15.5 pancreas sections. FIG. 1A illustrates miR-7 in situ hybridization on E15.5 pancreas sections, insets (FIG. 1B) is higher magnifications of the field marked by the dashed square. FIG. 1C illustrates fluorescent miR-7 in situ hybridization; FIG. 1D illustrates U6 in situ hybridization (positive control); FIG. 1E illustrates scrambled probe in situ hybridization (negative control); FIGS. 1F-H illustrate fluorescent miRNA in situ hybridization combined with immunostaining. miR-7 (red) co-localization with insulin (Ins; green, FIG. 1G) or glucagon (Gcg; white, FIG. 1H). Blue, nuclei. Insets (FIGS. 1V-W) are higher magnifications of the field marked by the dashed square. FIGS. 1I-N illustrate that miR-7 (red) is not expressed in acinar cells marked by Cpa1 at E15.5 (green, FIGS. 1J-K) or in duct cells marked by HNF1b at E14.5 (green, FIG. 1M). FIG. 1N is a higher magnification of the field marked by the dashed square in 1M. FIGS. 1O-T illustrate expression of miR-7 in many Ngn3-positive cells at E13.5 (white, FIGS. 1P-Q) as well as at E14.5 (FIGS. 1S-T). Higher magnification insets with arrowheads indicating representative cells that co-express miR-7 and Ngn3 (FIGS. 1X-Y). Scale bars: 50 µm. FIG. 1U is a graph illustrating that miR-7 expression is dependent on Ngn3. qPCR analysis of miR-7, miR-375, miR-17, let-7b in E14.5 Ngn3 knockout (KO) pancreatic buds, relative to Ngn3 heterozygous controls (WT). Data were normalized to sno234. qPCR data of Pax6 and insulin expression in the same samples, normalized to Hprt and Gapdh, and then presented relative to control. Error bars represent ±SEM **$P<0.05$.

Figure 2A:
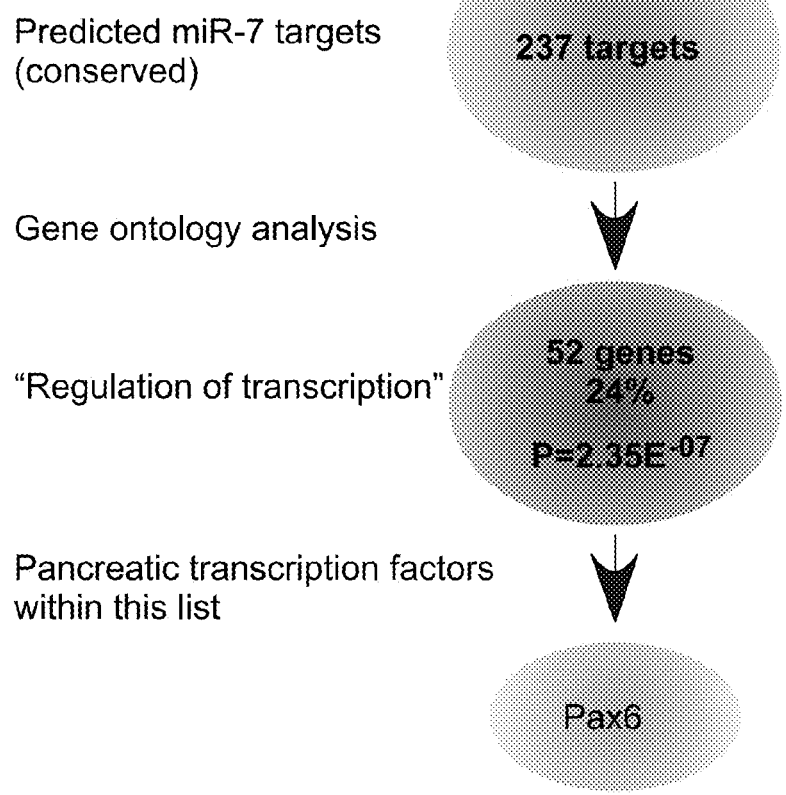

FIGS. 2A-K depict Pax6 as the target of miR-7. FIG. 2A is a schematic illustration of a gene ontology analysis of miR-7 predicted targets. Gene ontology analysis of miR-7 depicted 'Regulation of transcription" as significantly enriched ($P<2.35E^{-7}$). Within this list, Pax6 was the only characterized factor known to control pancreas development. FIG. 2B shows the predicted base pairing of mature miR-7 sequence (SEQ ID NO: 28) at the 3'UTRs of Pax6 (SEQ ID NO: 27). The seed sequence is marked with red; FIG. 2C is a histogram demonstrating the relative luciferase activity of a reporter that harbors the Pax6 3'UTR (742 bp). The expression of the luciferase reporter is repressed by miR-7 overexpression (miR-7 OE). Introduction of 'anti-miR' oligos (miR-7 KD) partially abrogates the repression. A reporter that harbors Pax6 3'UTR with deleted miR-7 seed sequence is completely insensitive to miR-7 OE ('mut UTR'). All data is normalized to the activity of firefly luciferase co-expressed from the dual reporter and to a negative control miRNA vector (Ctrl). n=3 independent experiments in triplicates, each; FIGS. 2D-E are representative western blots of PAX6 protein levels in MIN6 cells that were treated with miR-7 KD or miR-7 OE; FIGS. 2F-G are bar graph quantification of band densitometry of four independent experiments in duplicates (of FIGS. 2D-E), each (ANOVA test, $P<0.05$); FIGS. 2H-J are photographs depicting co-localization of miR-7 in situ hybridization (red), and Pax6 immunofluorescence (green) on E15.5 pancreas sections. Scale bar represent 50 µm; FIG. 2K is a qPCR analysis of miR-7 and Pax6 expression during pancreas development (E12.5-E15.5). A negative correlation between miR-7 expression (red, normalized to sno234 and then relative to E12.5) and Pax6 expression (black, normalized to Gapdh and then relative to E12.5). n=4, each pool of 3 pancreata from at least 2 litters. Error bars represent ±SEM ($P<0.05$).

Figures 3E, 3F, 3G, 3H, 3I, 3J:
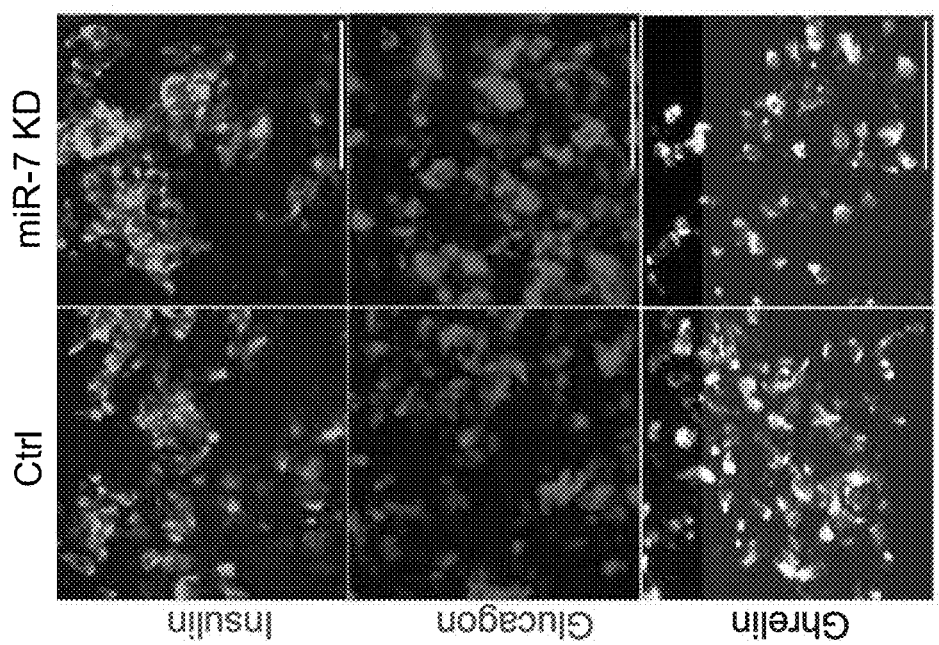
Figure 3K:
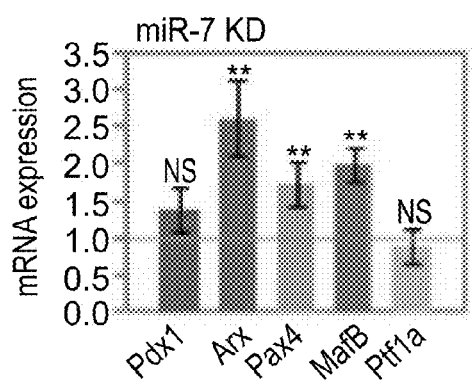
Figure 3L:
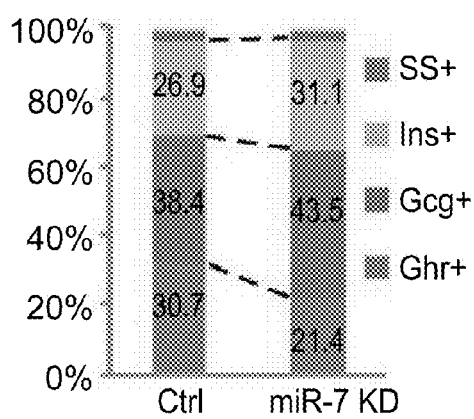
Figure 3M:
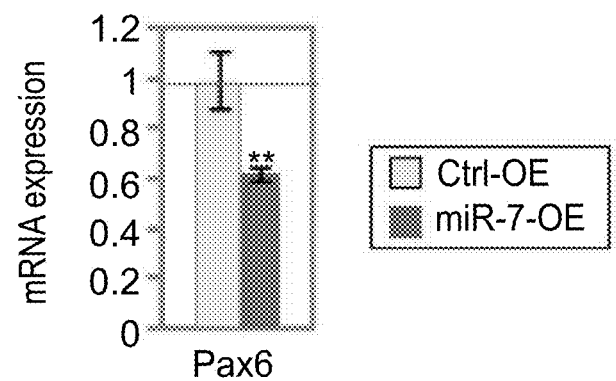
Figure 3N:
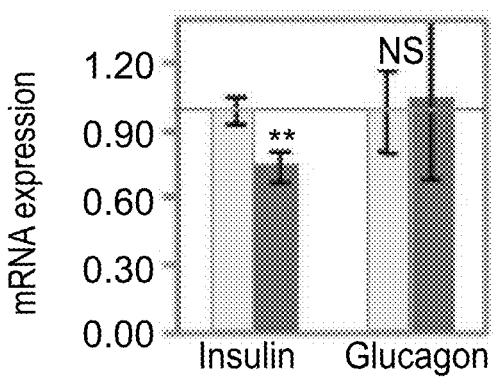
Figure 3O:
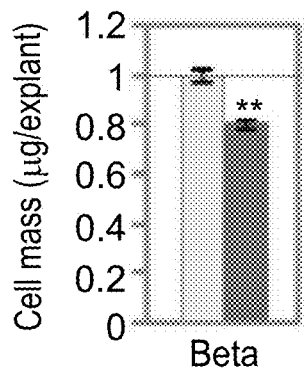
Figure 3R:
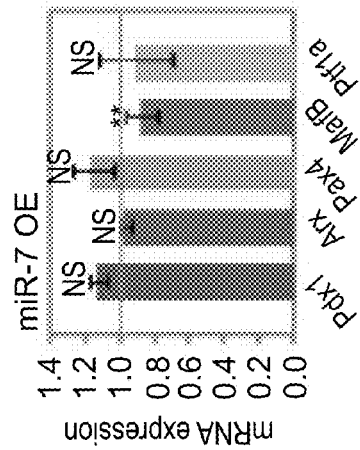
Figures 3P, 3Q:
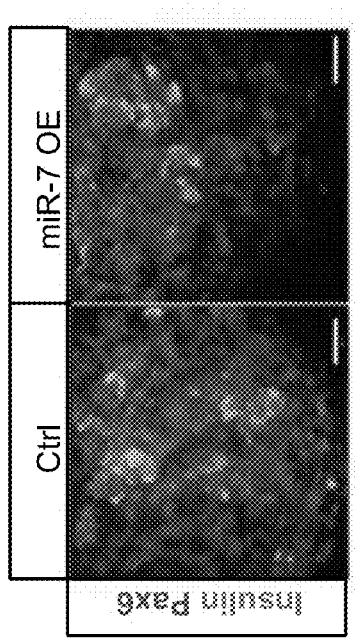
Figures 3S, 3T:
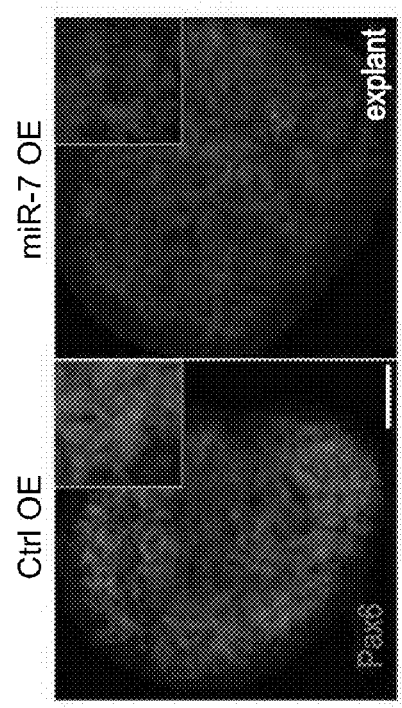

FIGS. 3A-T depict miR-7 knockdown and over expression in pancreatic explants. FIG. 3A is a scheme showing the experimental set up. Cholesterol-conjugated oligos introduced into the medium of E12.5 dorsal pancreatic buds that were grown in hanging drops for 48 hrs; FIGS. 3B-I illustrate miR-7 knockdown analysis (miR-7-KD, blue), relative to knockdown of control miRNA, miR-122 (Ctrl-KD, gray): FIG. 3B is a graph illustrating upregulated Pax6 mRNA expression upon miR-7 knockdown; FIG. 3C is a graph illustrating increased insulin and glucagon mRNA expression upon miR-7 knockdown; FIG. 3D is a graph illustrating that insulin protein levels are upregulated upon miR-7 KD, as measured by ELISA assay. Error bars represent ±s.e.m. $P<0.05$; FIGS. 3E-J are photographs representing immunostaining of insulin (green), glucagon (red) and ghrelin (white), taken for quantification. Scale bars represent 50 µm; FIG. 3K is a qPCR analysis of transcription factors expression. FIG. 3L is a graph illustrating the quantification of endocrine cell types (SS, somatostatin; Ghr, ghrelin; Gcg, glucagon; Ins, insulin). The percentage of cells in each individual population was calculated from the total number of counted cells in serial sections of the whole pancreas anlagen. At least three explants per treatment, average of three to eight independent experimental repeats. qPCR data are normalized to Hprt and Gapdh mRNA, and then to Ctrl KD treatment; FIGS. 3M-R illustrate analysis of miR-7 overexpression (miR-7-OE oligos, pink), relative to overexpression of control miRNA oligo, miR-67 (Ctrl-OE, gray): FIG. 3M is a graph illustrating repressed Pax6 mRNA expression in miR-7-OE explants; FIG. 3N is a graph illustrating decreased insulin mRNA expression in miR-7-OE explants, whereas glucagon levels remain similar; FIG. 3O reveals a significant reduction of beta cell mass in a morphometry of miR-7-OE explants; FIGS. 3P-Q are photographs representing immunostaining of insulin (green) and Pax6 (red), taken for quantification; FIG. 3R is a graph of a qPCR analysis of transcription factors expression. n=pools of 2-3 explants per treatment in the same litter, 3-6 independent experiments. All qPCR data normalized to Hprt and Gapdh mRNA and then to treatment with control oligos. Error bars represent ±SEM ( $P<0.05$); and FIGS. 3S-T are photographs illustrating Pax6 immunostaining in control and miR-7 OE.

FIGS. 4A-H depict explant differentiation in culture. FIGS. 4A-C are graphs illustrating qPCR analysis of Ngn3 mRNA, miR-7 and insulin mRNA expression in explants grown in culture. Of note, these results reveal the dynamics of endocrine gene expression under ex-vivo differentiation conditions. Data normalized to Gapdh or sno234 and to the expression at E12.5 (time-point 0). n=4 per time-point in two repeats; FIGS. 4D-E are photographs illustrating immunofluorescent detection of insulin (red) and glucagon (green) at 24 hrs or 70 hrs in culture. Of note, these results exemplify the propagation of endocrine differentiation ex-vivo; FIGS. 4F-H are photographs illustrating the efficiently taken up Cy3-bound-antagomir by pancreatic explants. Upper confocal optical section captures the periphery of the explants (FIG. 4F) and a central optical section reveals penetration of the Cy3-labeled antagomir deep into the explants (FIG. 4G). Cy3-labeled antagomir depicted in the cells in higher magnification. (FIG. 4H; nuclei, blue).

FIG. 4I is a graph depicting a Luciferase assay. HEK-293T cells were transfected with a luciferase reporter that harbors multiple miR-7 binding sites on its 3'UTR. The histogram demonstrates the ratio of firefly to *renilla* luciferase activity in negative control (Ctrl), cells overexpressing miR-7 (miR-7 OE) or cells overexpressing miR-7 and co-transfected with anti-miR-7 (miR-7 KD), normalized to control (3 experiments in triplicates).

Figure 5A:
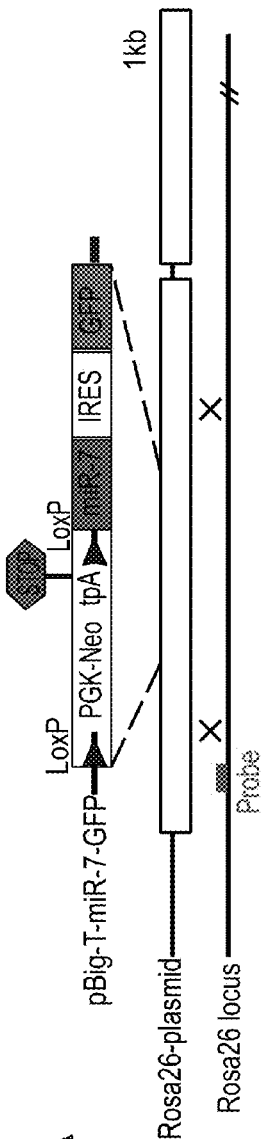
Figure 5B:
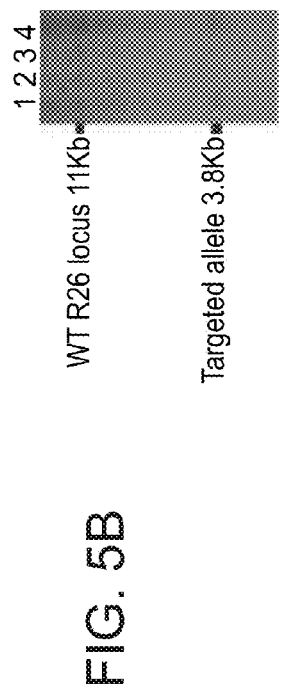
Figure 5C:
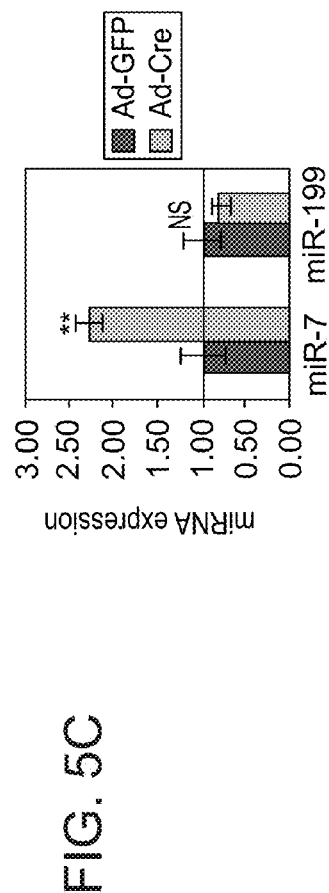
Figure 5K:
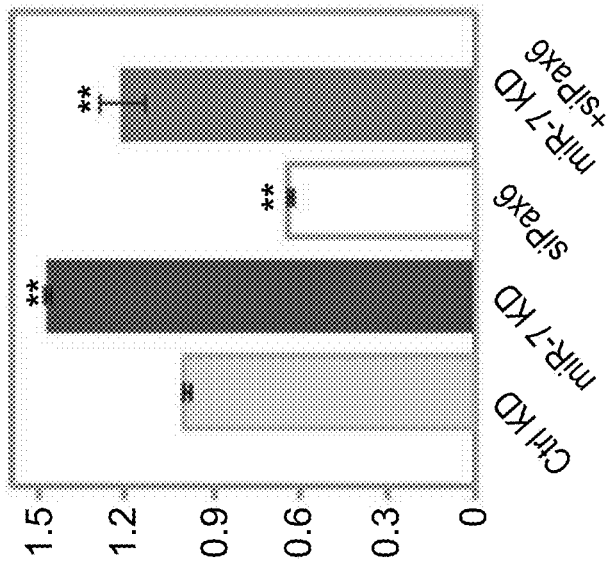
Figure 5L:
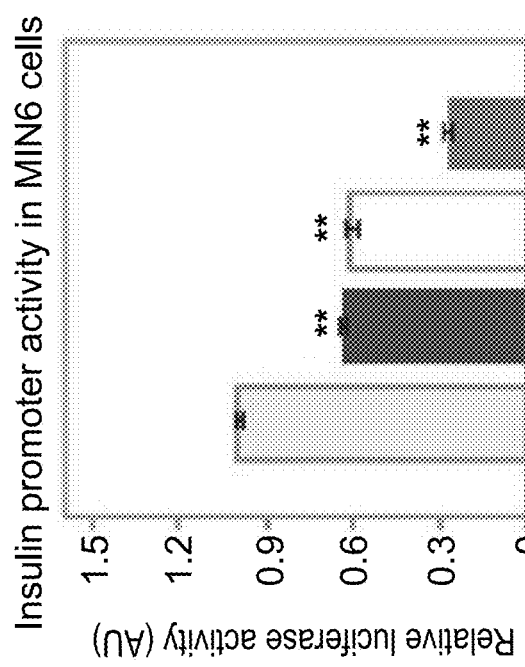

FIGS. 5A-L depict reduced expression of endocrine genes by in-vivo overexpression of miR-7. FIG. 5A is a schematic representation of the targeting construct for conditional miR-7-IRES-GFP misexpression; FIG. 5B shows a southern blot analyses of genomic DNA from wild-type (lanes 2,3) and targeted ES clone (lanes 1,4), using the probe denoted in red (see FIG. 5A); FIG. 5C is a graph showing that miR-7 up-regulation is Cre dependent. qPCR analysis of miR-7 and miR-199 levels in primary embryonic fibroblasts harvested from Rosa-miR-7 transgenic mice and infected with an adenovirus that expresses either Cre-GFP ('Ad-Cre') or GFP alone ('Ad-GFP'). Data normalized to sno234 (three independent MEF lines, each in triplicates); FIGS. 5D-E are photographs showing that GFP is specifically expressed in E13.5 Pdx1-Cre; Rosa-miR7 pancreatic epithelium but not in littermates that do not harbor the Cre recombinase ('Ctrl'). Asterisks depict erythrocyte autofluorescence; FIGS. 5F-J show that miR-7 mis-expression specifically repressed endocrine genes: FIG. 5F is a graph showing qPCR analysis of pancreatic genes in E15.5 Pdx1-Cre; Rosa-miR-7 samples, as indicated. Data normalized to Hprt and Gapdh mRNA and to the expression levels in littermate controls (n=6 each genotype, three litters). Error bars represent ±SEM (** $P<0.05$); FIGS. 5G-J are photographs showing immunostaining for insulin (green) and glucagon (red) in E15.5 sections of Pdx1-Cre; Rosa-miR-7 pancreas and control littermates [insets (FIGS. 5I-J) are higher magnifications of the field marked by the dashed squares]. Scale bar represents 50 µm; FIGS. 5K-L are graphs illustrating Pax6-miR-7 interaction upstream of insulin promoter activation in MIN6 cells. Of note, insulin promoter activity was downregulated by miR-7 overexpression, relative to control ('miR-7 OE', 'Ctrl OE', respectively) and was suppressed by siRNA against Pax6 siPax6). Combining miR-7 OE with siPax6 enhanced the suppressions of the insulin promoter (FIG. 5K). Insulin promoter activity was upregulated by miR-7 knockdown, relative to negative control scrambled oligo ('miR-7 KD', Ctrl KD', respectively). Concomitant introduction of miR-7 KD with siPax6 restored insulin promoter activity (FIG. 5L). All firefly luciferase data was normalized to the activity of *Renilla* luciferase co-transfected and presented relative to the control experiment. N=3 independent experiments. Error bars represent ±SEM **P<0.05.

Figure 6A:
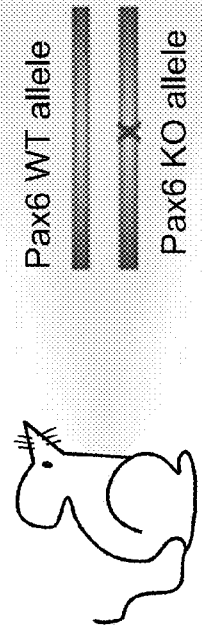
Figure 6B:
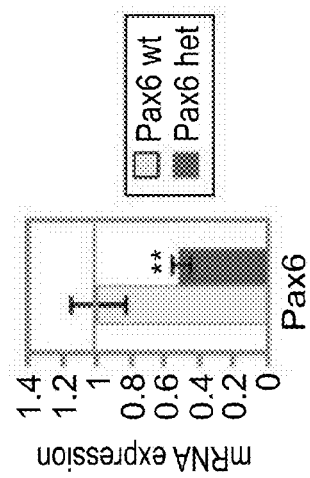
Figure 6E:
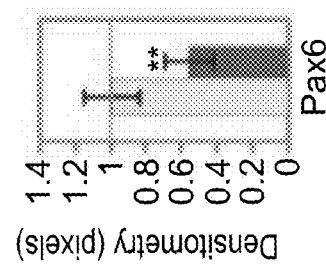
Figures 6C, 6D:
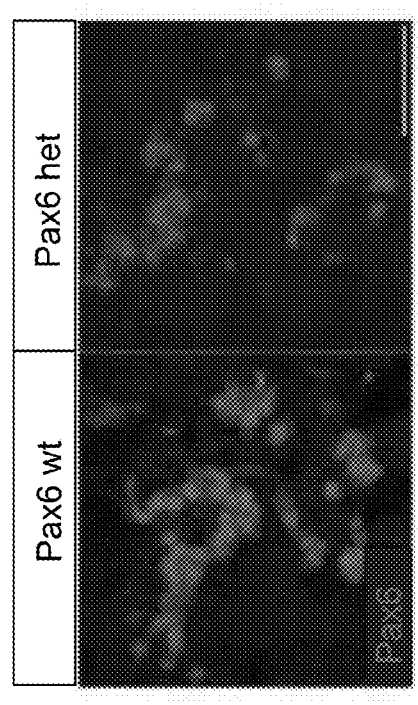

FIGS. 6A-J depict Pax6 haplo-insufficiency resembling miR-7 overexpression. FIG. 6A is a schematic illustration of a heterozygous (mono-allelic) mice model for expression of Pax6 in-vivo; FIG. 6B is a graph showing that Pax6 mRNA expression is reduced in E15.5 heterozygous pancreas ('het'), relative to wild-type littermates pancreas ('wt', two functional alleles); FIGS. 6C-E show reduced cellular expression of Pax6 in heterozygous pancreas, depicted by immunostaining (red). Scale bar represents 50 μm; FIG. 6F is a graph of a qPCR analysis showing reduced insulin and glucagon mRNA levels in Pax6 heterozygous pancreata, relative to wt littermates; FIG. 6G shows a qPCR analysis of transcription factors. All qPCR data were normalized to Hprt and Gapdh. n≥5 embryos per genotype, three independent litters. Error bars represent ±SEM (** P<0.05); FIGS. 6H-I are photographs of immunostaining for insulin (green) and glucagon (red) on E15.5 Pax6 heterozygous and wt littermates. Nuclei (blue); FIG. 6J is a graph showing a reduction in beta cell numbers. Hormone-positive cells were counted every eighth section throughout the pancreas and the average number of positive cells per organ, from several animals was normalized to wt controls (wt n=1912 cells; heterozygous n=1751 cells counted from 16 sections each).

FIGS. 7A-C depict miR-7 expression, upstream of Pax6 and dependent on Ngn3. FIG. 7A is a graph showing that miR-7 is upstream of Pax6. qPCR study of miR-7, miR-17 and let7b expression in E14.5 wild type (wt), Pax6 heterozygous (het) and knockout (KO) animals, normalized to sno234; FIG. 7B is schematic illustrations of Ngn3, Pax6 and miR-7 which are wired into an 'incoherent feed-forward-loop'. This is a conserved network, described in the differentiation of neurons in the retina of *Drosophila Melanogaster* (FIG. 7C).

FIGS. 8A-S depict that miR-7 KD controls endocrine differentiation. FIGS. 8A-J are photographs illustrating an analysis of endocrine-cell populations by whole mount immunostaining for Ngn3 (green), Insulin (red), Glucagon (white), Somatostatin (magenta) and Ghrelin (white) in control (FIGS. 8A-E) and miR-7 KD explants (FIGS. 8F-J); FIGS. 8K-0 are graphs illustrating quantification of positive area by analysis of the stained area, relative to the total explant area (done with Nis elements software, additional details are described in the 'materials and experimental procedures' section, hereinbelow); FIGS. 8P-S are graphs illustrating the cell number quantification of Ngn3-, Insulin- (Ins) Glucagon (Gcg)- and Ghrelin (Ghr) positive cells. Positive cells were manually counted in stacked confocal images of the entire explants. 3-5 explants per treatment. Error bars represent ±SEM (** P<0.05).

FIGS. 9A-G depict that proliferation is not affected by miR-7 KD. FIGS. 9A-C illustrate no change in proliferating of insulin-positive cells, upon miR-7 KD relative to Ctrl. Double positive Ki67-positive/insulin-positive cells were counted from the entire explant (>3 per genotype) and their percentage from the insulin positive population is presented in FIG. 9C; FIGS. 9D-F illustrate no change in proliferation of glucagon-positive cells, upon miR-7 KD. FIGS. 9D-E are photographs of double positive BrdU-positive/Glucagon-positive cell population was counted and quantified. FIG. 9G illustrates that the total numbers of BrdU-positive cells are comparable between mir-7 KD and Ctrl. Error bars represent ±SEM (** P<0.05).

Figure 10:
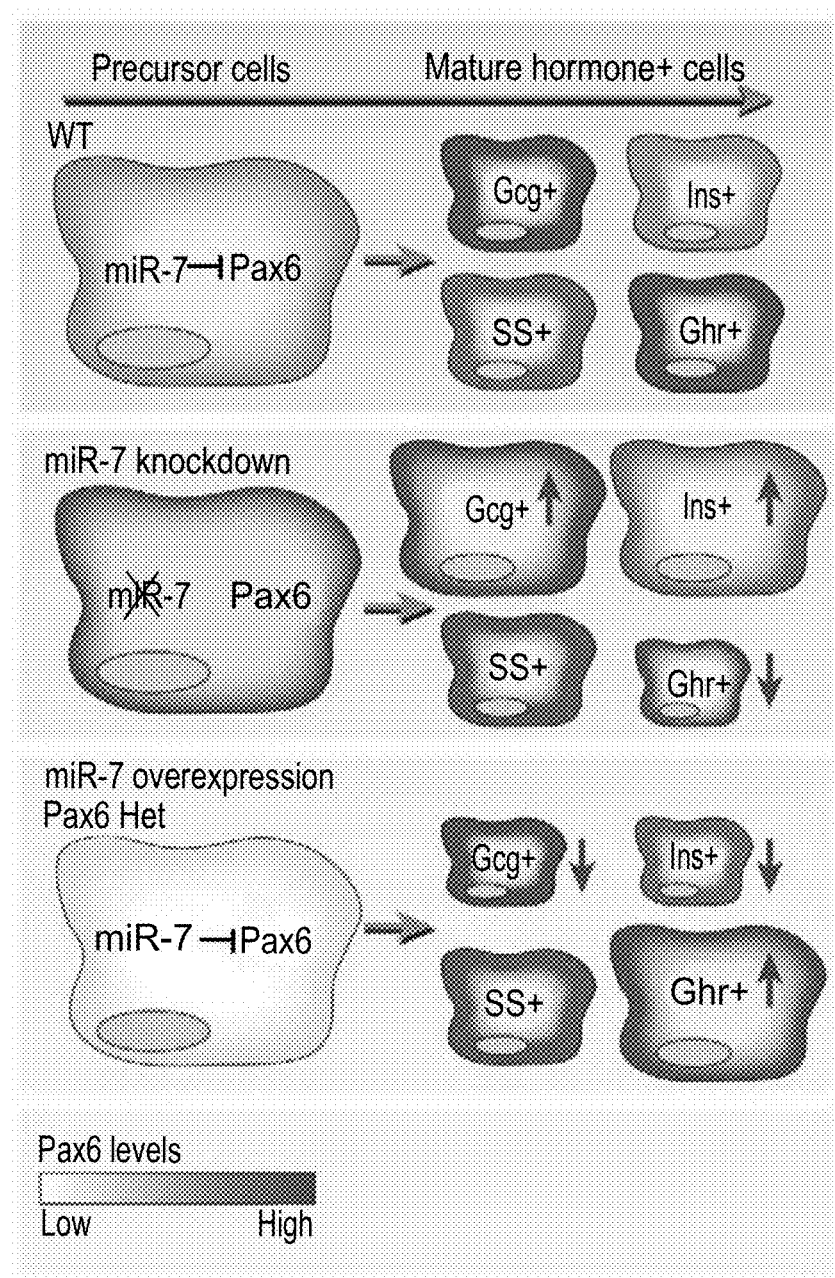

FIG. 10 is a schematic model depicting miR-7-Pax6 interactions in pancreas development. The regulation of Pax6 levels (blue) by miR-7, regulates the differentiation of hormone-expressing endocrine cells. miR-7 knockdown de-represses Pax6 and results in reduced ghrelin (Ghr) expression and preference towards insulin and glucagon-positive cells (Ins and Gcg). Similarly, miR-7 overexpression or heterozygous (Het) expression of Pax6 results in reduced Pax6 and reciprocal changes in the expression of hormones.

DESCRIPTION OF SPECIFIC EMBODIMENTS OF THE INVENTION

The present invention, in some embodiments thereof, relates to downregulation of microRNA-7 and, more particularly, but not exclusively, to the use of same for promoting insulin production from pancreatic beta cells.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Differentiation of endocrine pancreatic beta cells is controlled by a network of pancreatic transcription factors including Ngn3 acting upstream of Pax6. Pax6 is pivotal in the differentiation of pancreatic beta-cells and any deviation from normal Pax6 expression has severe developmental consequences (e.g. induction of cell apoptosis). Genome-encoded miRNAs bind to specific sites on the 3' untranslated region (3'UTR) of their target mRNAs and provide a post-transcriptional regulatory layer that along with transcription factors act to refine gene expression. Previous studies have shown that total inactivation of miRNA maturation causes pancreas agenesis [Lynn et al. (2007) Diabetes 56(12):2938-45], while Melkman-Zehavi et al. disclosed that specific knockdown of miR-24, miR-26, miR-182 or miR-148 in beta cells downregulates insulin promoter activity and insulin mRNA levels [Melkman-Zehavi et al. (2011) EMBO Journal 1-11].

While reducing the present invention to practice, the present inventors have uncovered that endocrine-specific microRNA-7 (miR-7) acts downstream of Ngn3 to directly repress Pax6 expression and to thereby modulate pancreatic beta cell differentiation and insulin production therefrom.

As is illustrated hereinbelow and in the Examples section which follows, the present inventors have shown that miR-7 knockdown resulted in Pax6 upregulation and further resulted in reduced ghrelin producing cells and preference towards insulin and glucagon-producing cells (see Example 3 of the Examples section which follows). Similarly, miR-7 overexpression in developing pancreas explants or in a new mouse transgene led to Pax6 downregulation and to preference towards ghrelin producing cells, while significantly reducing the number of insulin and glucagon-producing cells (e.g. beta and alpha cells, respectively, see Example 4 of the Examples section which follows). Taken together, these results substantiate the value of downregulation of miR-7 for promoting pancreatic beta cell regeneration and increasing insulin protein levels.

Thus, according to one aspect of the present invention there is provided a method of treating a medical condition associated with an insulin deficiency in a subject in need thereof, the method comprising administering to the subject an agent for downregulating an activity or expression of miR-7, thereby treating the medical condition associated with the insulin deficiency.

The term "treating" refers to inhibiting or arresting the development of a disease, disorder or condition and/or causing the reduction, remission, or regression of a disease, disorder or condition or keeping a disease, disorder or medical condition from occurring in a subject who may be at risk for the disease disorder or condition, but has not yet been diagnosed as having the disease disorder or condition. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "subject" refers to an animal, preferably a mammal, or a human being, of any age or sex, who suffers from or is predisposed to an insulin deficiency associated disorder.

Diseases or syndromes which are associated with an insulin deficiency include, but are not limited to, type 1 and type 2 diabetes mellitus, metabolic syndrome, type 1 and type 2 diabetes mellitus subtypes, insulin deficiency syndrome, maturity onset diabetes of the young (MODY 1-11), and permanent neonatal diabetes mellitus.

According to a specific embodiment of the present invention, the insulin deficiency comprises diabetes.

According to a specific embodiment of the present invention, the insulin deficiency comprises diabetes type 1.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

In order to treat the medical condition, pancreatic beta cells may be generated ex-vivo and then used for therapy.

Thus, according to one aspect of the present invention there is provided a method of ex-vivo increasing insulin content in beta cells or stem cells, the method comprising contacting the beta cells or stem cells with an agent for downregulating an activity or expression of miR-7, thereby increasing the insulin content in the beta cells or stem cells.

As used herein the phrase "ex-vivo" refers to a process in which cells, which are removed from a living organism, are subjected to a treatment and alternatively or additionally culturing outside the organism (e.g., in a cell culture plate or test tube). According to an embodiment ex-vivo includes in vitro, especially in the case cell-lines.

As used herein, the phrase "insulin content" refers to the amount of insulin polypeptides or peptides derived therefrom (e.g. mature insulin) inside an insulin producing cell (e.g. pancreatic beta cell) or secreted therefrom.

Measurement of insulin content is well known in the art. An exemplary method is extraction of cellular insulin with 3 M acetic acid. The amount of mature insulin extracted from the pancreatic beta cell may be determined using, for example, an enzyme-linked immunosorbent assay (ELISA) kit commercially available from e.g. Mercodia, Uppsala, Sweden. Alternatively Western Blot analysis, Immunofluorescence or Immunohistochemistry may be carried out using specific antibodies available, from e.g. Cell Signaling Technology, Thermo Scientific Pierce Antibodies or GeneTex.

According to one embodiment, the beta cells comprise isolated cells. The isolated beta cells may be of homogeneous or heterogeneous nature.

The term "isolated" refers to at least partially separated from the natural environment e.g., from a body.

The phrase "beta cells" as used herein refers to pancreatic islet endocrine cells capable of producing and secreting insulin (e.g. in response to physiological signals such as elevated glucose concentrations) and expressing typical beta cell markers including, but not limited to, insulin, pdx, Hnf3β, PC1/3, Beta2, Nkx2.2, GLUT2 and PC2.

According to one embodiment, the beta cells are mature beta cells.

The phrase "mature beta cells" as used herein refers to fully differentiated and functional pancreatic islet endocrine cells. Typically such cells secrete insulin in response to glucose stimulation. Furthermore, mature beta cells typically express typical beta cell markers including, but not limited to, insulin, pdx, Hnf3β, PC1/3, Beta2, Nkx2.2, GLUT2 and PC2.

According to one embodiment, the beta cells are precursor beta cells.

The phrase "precursor beta cells" as used herein refers to cells that have the capacity to develop/differentiate into pancreatic islet endocrine cells capable of producing and secreting insulin (e.g. in response to physiological signals such as elevated glucose concentrations) and expressing typical beta cell markers including, but not limited to, insulin, pdx, Hnf3β, PC1/3, Beta2, Nkx2.2, GLUT2 and PC2.

The precursor beta cells of the present invention may comprise pancreatic progenitor cells, somatic cells (capable of transdifferentiation into insulin producing beta cells) and beta cell lines.

According to a specific embodiment, the precursor beta cells are pancreatic progenitor cells of an adult or fetal pancreas (i.e., of any gestational age). Such pancreatic progenitor cells may be obtained from the pancreatic islets, ducts or acini of an adult or fetal pancreas.

Thus, for example, the pancreatic progenitor cells may be comprised in isolated pancreatic islets. Islet cells are typically comprised of the following: 1) beta cells that produce insulin; 2) alpha cells that produce glucagon; 3) delta cells (or D cells) that produce somatostatin; and/or F cells that produce pancreatic polypeptide. The polypeptide hormones (insulin, glucagon, somatostatin and pancreatic polypeptide) inside these cells are stored in secretary vesicles in the form of secretory granules.

Methods of isolating pancreatic progenitor cells are well known in the art. For example, pancreatic tissue may be obtained from a human subject or donor by any method known in the art (e.g. using a biopsy guided by ultrasound or CT, by laparoscopy or by laparotomy). Islets may then be isolated from pancreatic tissue using collagenase and ficoll gradients. An exemplary method is described in U.S. Patent Application No. 20080014182, incorporated herein by reference. It will be appreciated that the pancreatic progenitor cells may be further isolated from the islets (or from ducts or acini as needed) e.g. by FACS sorting or clonal analysis using identification of specific progenitor markers, such as, but not limited to, expression of nestin, Ngn-3, c-met Arx, Pax4, Pax6, insulin, glucagon, glut2, Nkx2.2, Nkx6.1, Gck, Sur1, Kir6.2 and/or NeuroD/Beta2.

According to another specific embodiment, the precursor beta cells comprise somatic cells capable of transdifferentiation into insulin producing beta cells. Somatic cells as of the present teachings comprise both fetal and adult cells including, for example, liver cells, neuroendocrine cells, intestinal cells, fibroblasts, myoblasts and monocytes.

According to a specific embodiment, the precursor beta cells comprise transdifferentiated liver cells (i.e. liver cells which underwent differentiation into pancreatic cells), as taught e.g. by Sapir T. et al., Proc. Natl. Acad. Sci. USA (2005) 102 (22) 7964-7969 and by Zalzman M. et al., Diabetes (2005) 54(9):2568-2575.

It will be appreciated that somatic cells may be isolated by any cell isolation method known in the art [e.g. for liver cell isolation see for example Alpini G. et al., Recent advances in the isolation of liver cells. Hepatology (1994) August; 20(2):494-514]. Furthermore, the isolated somatic cells (e.g. liver cells) may undergo any molecular manipulation (e.g. genetic modification) or culturing with specific agents [e.g. specific soluble factors (SSF) such as activin-A, nicotinamide or HGF] in order to induce transdifferentiation thereof into insulin producing beta-like cells.

As used herein, the phrase "stem cells" refers to cells which are capable of remaining in an undifferentiated state (i.e. "pluripotent stem cells") for extended periods of time in culture until induced to differentiate into other cell types having a particular, specialized function (i.e., "fully differentiated" cells).

Preferably, the phrase "stem cells" encompasses embryonic stem cells (ESCs), induced pluripotent stem cells (iPS), adult stem cells and hematopoietic stem cells. According to a specific embodiment, the stem cells are of a human origin. Alternatively, the stem cells may be any mammalian stem cells, such as for example from a human, porcine, rodent (e.g. mouse or rat) or primate (e.g. monkey) origin.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

The embryonic stem cells of the present invention can be obtained using well-known cell-culture methods. For example, human embryonic stem cells can be isolated from human blastocysts. Human blastocysts are typically obtained from human in-vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used with this aspect of the present invention. Human ES cells can be purchased from the NIH human embryonic stem cells registry [www(dot)escr(dot)nih(dot)gov]. Non-limiting examples of commercially available embryonic stem cell lines are BG01, BG02, BG03, BG04, CY12, CY30, CY92, CY10, TE03 and TE32.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-programs the cell to acquire embryonic stem cells characteristics. According to some embodiments of the invention, the induced pluripotent stem cells are formed by inducing the expression of Oct-4, Sox2, Kfl4 and c-Myc in a somatic stem cell. Lineage specification of human iPS cells into functional glucose-responsive, insulin-producing progeny have been previously taught e.g. by Thatava T. et al., Indolactam V|[sol]|GLP-1-mediated differentiation of human iPS cells into glucose-responsive insulin-secreting progeny, Gene Therapy (2011) 18, 283-293.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

According to a specific embodiment, the precursor beta cells comprise de-differentiated beta cells.

The phrase "de-differentiated beta cells" refers to a partially or terminally differentiated beta cells which revert to an earlier developmental stage (e.g. non-insulin secreting cells) capable of re-differentiating into beta cells.

According to another specific embodiment, the de-differentiated beta cells comprise induced pluripotent stem cells generated from beta cells.

According to another specific embodiment, the precursor beta cells comprise de-differentiated beta cell lines.

The phrase "adult stem cells" (also called "tissue stem cells" or a stem cell from a somatic tissue) refers to any stem cell derived from a somatic tissue [of either a postnatal or prenatal animal (especially the human)] which is capable of differentiating into beta cells. The adult stem cell is generally thought to be a multipotent stem cell, capable of differentiation into multiple cell types. Adult stem cells can be derived from any adult, neonatal or fetal tissue such as adipose tissue, skin, kidney, liver, prostate, pancreas, intestine, bone marrow and placenta.

Hematopoietic stem cells, which may also referred to as adult tissue stem cells, include stem cells obtained from blood or bone marrow tissue of an individual at any age or from cord blood of a newborn individual.

Methods of isolating adult tissue stem cells are known in the arts and include, for example, those disclosed by Alison, M. R. [Tissue-based stem cells: ABC transporter proteins take center stage. J Pathol. (2003) 200(5): 547-50], Cal, J. et al., [Identifying and tracking neural stem cells. Blood Cells Mol Dis. (2003) 31(1): 18-27] and Collins, A. T. et al., [Identification and isolation of human prostate epithelial stem cells based on alpha(2)beta(1)-integrin expression. J Cell Sci. (2001) 114(Pt 21): 3865-72].

Generally, isolation of adult tissue stem cells is based on the discrete location (or niche) of each cell type included in the adult tissue, i.e., the stem cells, the transit amplifying cells and the terminally differentiated cells [Potten, C. S. and Morris, R. J. (1988) Epithelial stem cells in-vivo. J. Cell Sci. Suppl. 10, 45-62]. Thus, an adult tissue such as, for example, prostate tissue is digested with Collagenase and subjected to repeated unit gravity centrifugation to separate the epithelial structures of the prostate (e.g., organoids, acini and ducts) from the stromal cells. Organoids are then disaggregated into single cell suspensions by incubation with Trypsin/EDTA (Life Technologies, Paisley, UK) and the basal, CD44-positive, stem cells are isolated from the luminal, CD57-positive, terminally differentiated secretory cells, using anti-human CD44 antibody (clone G4426; Pharmingen, Becton Dickinson, Oxford, UK) labeling and incubation with MACS (Miltenyi Biotec Ltd, Surrey, UK) goat anti-mouse IgG microbeads. The cell suspension is then applied to a MACS column and the basal cells are eluted and re-suspended in WAJC 404 complete medium [Robinson, E. J. et al. (1998) Basal cells are progenitors of luminal cells in primary cultures of differentiating human prostatic epithelium Prostate 37, 149-160].

Since basal stem cells can adhere to basement membrane proteins more rapidly than other basal cells [Jones, P. H. et al. (1995) Stem cell patterning and fate in human epidermis. Cell 60: 83-93; Shinohara, T., et al. (1999) beta1- and alpha6-integrin are surface markers on mouse spermatogonial stem cells. Proc. Natl. Acad. Sci. USA 96: 5504-5509] the CD44 positive basal cells are plated onto tissue culture dishes coated with either type I collagen (52 µg/ml), type IV collagen (88 µg/ml) or laminin 1 (100 µg/ml; Biocoat®, Becton Dickinson) previously blocked with 0.3% bovine serum albumin (fraction V, Sigma-Aldrich, Poole, UK) in Dulbecco's phosphate buffered saline (PBS; Oxoid Ltd, Basingstoke, UK). Following 5 minutes, the tissue culture dishes are washed with PBS and adherent cells, containing the prostate tissue basal stem cells are harvested with trypsin-EDTA.

According to one embodiment, the stem cells utilized by the present invention are bone marrow (BM)-derived stem cells including hematopoietic, stromal or mesenchymal stem cells (Dominici, M et al., 2001. Bone marrow mesenchymal cells: biological properties and clinical applications. J. Biol. Regul. Homeost. Agents. 15: 28-37). BM-derived stem cells may be obtained from iliac crest, femora, tibiae, spine, rib or other medullar spaces.

Of the above described BM-derived stem cells, mesenchymal stem cells are the formative pluripotent blast cells, and as such are preferred for use with the present invention. Mesenchymal stem cells give rise to one or more mesenchymal tissues (e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Although such cells can be isolated from embryonic yolk sac, placenta, umbilical cord, fetal and adolescent skin, blood and other tissues (e.g. liver, intestine, brain), their abundance in the BM far exceeds their abundance in other tissues and as such isolation from BM is presently preferred.

According to another embodiment, the stem cells comprise mesenchymal stem cells.

Methods of isolating, purifying and expanding adult stem cells including mesenchymal stem cells (MSCs) are known in the arts and include, for example, those disclosed by Caplan and Haynesworth in U.S. Pat. No. 5,486,359 and Jones E. A. et al. [Jones E. A. et al. (2002) Isolation and characterization of bone marrow multipotential mesenchymal progenitor cells, Arthritis Rheum. 46(12): 3349-60].

Once the precursor beta cells or stem cells are obtained, the cells may be dispersed into a single cell suspension (e.g. by the addition of trypsin or by trituration) and are typically cultured (e.g. in cell medium such as CMRL-1066, available from e.g. Cellgro, Mediatech, Inc.). It will be appreciated that the cells may be grown in a serum free medium or on a matrix overlay with Matrigel. Additionally or alternatively, additional factors may be added to the cell culture medium which support expansion/differentiation of beta cells or which inhibit apoptosis of beta cells, such factors include but are not limited to, growth factors [e.g. fibroblast growth factor (FGF), hepatocyte growth factor (HGF)], hormones [e.g. gastrin, glucagon-like peptide-1 (GLP-1)] and/or insulinotropic agents (e.g. nicotinamide).

Furthermore, the precursor beta cells of the present invention express elevated levels of miR-7 which are higher than that of mature functioning beta cells which secret insulin in response to glucose.

The level is preferably determined in reference to a control cell (being a fully differentiated and functioning beta cell, which secretes insulin in response to glucose stimulation e.g. for normal glucose homeostasis).

According to a specific embodiment a de-differentiated state is when the level of miR-7 in the tested cell is at least 50%, 40%, 30%, 20%, 10% or lower than that of the control cell.

As is mentioned hereinabove, following isolation and culturing, the beta cells (e.g. precursor beta cells) or stem cells of the present invention are contacted with an agent for downregulating (i.e. decreasing) an activity or expression of miR-7 in such cells.

According to the present teachings, downregulation of the activity or expression microRNA-7 (miR-7) in pancreatic beta cells results in cell differentiation and in an increase in insulin content in these cells (see Example 3 of the Examples section which follows). The increase in insulin levels can be a result of an increase in insulin transcription and/or post transcriptional control and/or increase in insulin translation and/or post-translational control. The increase in insulin content in the pancreatic beta cells according to the present teachings may also result from enhanced insulin storage and/or retarding insulin breakdown.

As used herein, the term "miR-7" refers to the microRNA (miRNA) molecule acting as post-transcriptional regulator. Exemplary miR-7 polynucleotide sequences are set forth in SEQ ID NOs: 21-26 and by GenBank accession nos. NR_029605.1, NR_029606.1 or NR_029607.1.

MicroRNAs are typically processed from pre-miR (pre-microRNA precursors). Pre-miRs are a set of precursor miRNA molecules transcribed by RNA polymerase III that are efficiently processed into functional miRNAs, e.g., upon transfection into cultured cells. A Pre-miR can be used to elicit specific miRNA activity in cell types that do not normally express this miRNA, thus addressing the function of its target by down regulating its expression in a "gain of (miRNA) function" experiment. Pre-miR designs exist to all of the known miRNAs listed in the miRNA registry (see below) and can be readily designed for any research.

Thus, the miR-7 of the present teachings may bind, attach, regulate, process, interfere, augment, stabilize and/or destabilize any target thereof. Such a target can be any molecule, including, but not limited to, DNA molecules, RNA molecules and polypeptides, such as but not limited to, transcription factors such as Pax6.

It will be appreciated that the miR-7 of the present invention is part of, involved in and/or is associated with an insulin transcription pathway. MiR-7 can thus be identified via various databases including for example the micro-RNA registry (http://wwwdotsangerdotacdotuk/Software/Rfam/mirna/indexdotshtml).

Downregulation of miR-7 can be effected on the genomic and/or the transcript level using a variety of molecules which interfere with transcription (e.g., RNA silencing agents, Ribozyme, DNAzyme and antisense).

Following is a list of agents capable of downregulating expression level and/or activity of miR-7.

Nucleic acid agents that downregulate miR-7 activity include, but are not limited to, a target mimic, a micro-RNA resistant gene and a miRNA inhibitor.

The target mimic or micro-RNA resistant target is essentially complementary to the microRNA provided that one or more of following mismatches are allowed:

(a) a mismatch between the nucleotide at the 5' end of the microRNA and the corresponding nucleotide sequence in the target mimic or micro-RNA resistant target;

(b) a mismatch between any one of the nucleotides in position 1 to position 9 of the microRNA and the corresponding nucleotide sequence in the target mimic or micro-RNA resistant target; or (c) three mismatches between any one of the nucleotides in position 12 to position 21 of the microRNA and the corresponding nucleotide sequence in the target mimic or micro-RNA resistant target provided that there are no more than two consecutive mismatches.

The target mimic RNA is essentially similar to the target RNA modified to render it resistant to miRNA induced cleavage, e.g. by modifying the sequence thereof such that a variation is introduced in the nucleotide of the target sequence complementary to the nucleotides 10 or 11 of the miRNA resulting in a mismatch.

Alternatively, a microRNA-resistant target may be implemented. Thus, a silent mutation may be introduced in the microRNA binding site of the target gene so that the DNA and resulting RNA sequences are changed in a way that prevents microRNA binding, but the amino acid sequence of the protein is unchanged. Thus, a new sequence can be synthesized instead of the existing binding site, in which the DNA sequence is changed, resulting in lack of miRNA binding to its target.

According to a specific embodiment, the target mimic or micro-RNA resistant target is linked to the promoter naturally associated with the pre-miRNA recognizing the target gene and introduced into the cell. In this way, the miRNA target mimic or micro-RNA resistant target RNA will be expressed under the same circumstances as the miRNA and the target mimic or micro-RNA resistant target RNA will substitute for the non-target mimic/micro-RNA resistant target RNA degraded by the miRNA induced cleavage.

Non-functional miRNA alleles or miRNA resistant target genes may also be introduced by homologous recombination to substitute the miRNA encoding alleles or miRNA sensitive target genes.

Recombinant expression is effected by cloning the nucleic acid of interest (e.g., miRNA, target gene, silencing agent, etc.) into a nucleic acid expression construct under the expression of a promoter.

In other embodiments of the invention, synthetic single stranded nucleic acids are used as miRNA inhibitors. A miRNA inhibitor is typically between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, a miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA.

According to an embodiment, peptide nucleic acids oligonucleotide analogues (PNA ON) are used as miRNA inhibitors. Such miRNA inhibitors have been described in detail in Torres et al., *Nucleic Acids Research* (2011) 1-16, incorporated herein by reference.

The miRNA inhibitors may be contacted with the cells using transient or stable transfection techniques. Thus, the miRNA inhibitors may be part of an expression vector, as described hereinbelow.

According to one embodiment, downregulating the expression of a microRNA is effected by the use of a nucleic acid sequence which specifically binds and downregulates the expression of the microRNA. A nucleic acid sequence which may be used in accordance with the present invention may be purchased from any manufacturer, as for example, from Genecopoeia (miArrest, microRNA vector based inhibitors).

According to another embodiment, there is provide an isolated polynucleotide comprising a nucleic acid sequence for downregulating an expression of miR-7 or a precursor thereof.

Exemplary polynucleotides which may be used in accordance with the present invention to downregulate the expression of miR-7 include, but are not limited to, those set in SEQ ID NOs: 36-41.

Downregulation of miR-7 can also be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

Downregulation of miR-7 can be effected by using an antisense polynucleotide capable of specifically hybridizing with an mRNA transcript encoding miR-7.

Design of antisense molecules which can be used to efficiently downregulate miR-7 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published [Matveeva et al., Nature Biotechnology 16: 1374-1375 (1998)].

MiR-7 antisense agents include, but are not limited to, antisense molecules which target and inhibit miR-7 described in detail in Cheng A. M. et al., *Nucleic Acids Research* 2005 33(4):1290-1297, incorporated herein by reference, and anti-miRNA oligos available from e.g. IDT (Integrated DNA Technologies, Inc, Israel) and also available from Exicon (miRCURY LNA™ microRNA Inhibitors, for more details see http://wwwdotexiqondotcom/microrna-knockdown).

It will be appreciated that the microRNA antisense agents (e.g. anti-miRNA oligos) of the present invention may also comprise chemical modifications, molecular modifications and/or the addition of moieties, e.g. a cholesterol moiety (e.g. antagomirs). Such molecules have been previously described in e.g. Kriitzfeldt J. et al., Nature (2005) 438: 685-9 and Lennox and Behlke: Gene Therapy (2011) REVIEW: Chemical modification and design of anti-miRNA oligonucleotides, pg. 1-10.

According to a specific embodiment, the agent for downregulating an activity or expression of miR-7 is an antagomir. An exemplary antagomir which may be used according to the present teachings include Anti-miR-7 antagomir (2'OH)-chl (SEQ ID NO: 19).

Downregulation of miR-7 can also be effected by RNA interference. RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target), The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with the present invention can be effected as follows. First, the miR-7 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, mouse, rat etc.) using any sequence alignment software, such as the BLAST software available from the NCBI server (wwwdotncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIsl, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of the present invention may be targeted to a bridging region on either side of the deletion. Introduction of such RNA silencing agents into a cell would cause a down-regulation of the mutated protein while leaving the non-mutated protein unaffected.

Exemplary miR-7 silencing agents include, but are not limited to, Anti-miR™ miRNA Inhibitors available from Ambion Inc. for inhibition of miR-7 (for more details see https://productsdotappliedbiosystemsdotcom/ab/en/US/adirect/ab?cmd=ABAntiPremiR NAKeywordSearch).

Another agent capable of downregulating miR-7 is a DNAzyme molecule capable of specifically cleaving an mRNA transcript or DNA sequence of miR-7. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, LM [Curr Opin Mol Ther 4:119-21 (2002)]).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in-vivo (Itoh et al, 20002, Abstract 409, Ann Meeting Am Soc Gen Ther wwwdotasgtdotorg). In another application, DNAzymes complementary to bcr-ab1 oncogenes were successful in inhibiting the oncogenes expression in leukemia cells, and lessening relapse rates in autologous bone marrow transplant in cases of CML and ALL.

Another agent capable of downregulating miR-7 is a ribozyme molecule capable of specifically cleaving an mRNA transcript encoding miR-7. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Ribozymes specific for targeting miR-7 can be designed as was previously described by Suryawanshi, H. et al. [Supplementary Material (ESI) for Molecular BioSystems, The Royal Society of Chemistry 2010, incorporated herein by reference].

An additional method of regulating the expression of a miR-7 gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the miR-7 regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Expressing the miR-7 downregulating agents of the present invention in beta cells (e.g. precursor beta cells) or stem cells may be effected using expression constructs encoding the miR-7 downregulating agents and capable of expressing same in the beta cells or stem cells.

The nucleic acid construct (also referred to herein as an "expression vector") of the present invention typically includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, and Bell M P et al., J Immunol. (2007) 179(3):1893-900, both of which are incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of the miR-7 downregulating agents' mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., (Arch Virol. 2004; 149:51-60).

Various methods can be used to introduce the expression vector of the present invention into the beta cells or stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 1986; 4:504-512] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

As illustrated in Example 2 and Table 4, hereinbelow, miR-7 has multiple target genes. Thus, insulin content may be increased by upregulating in beta cells or stem cells expression of a miR-7 target gene.

Thus, there is provided a method of increasing insulin content in beta cells or stem cells, the method comprising expressing in the beta cells or stem cells a target gene of miR-7.

According to an embodiment, the target gene of miR-7 comprises epidermal growth factor receptor (EGFR), insulin-degrading enzyme (IDE), insulin receptor substrate 2 (IRK), Kruppel-like factor 4 (KLF4), GLI family zinc finger 3 (GLI3), insulin receptor substrate 1 (IRS1), Sp1 transcription factor (SP1), O-linked N-acetylglucosamine (GlcNAc) transferase (UDP-N-acetylglucosamine:polypeptide-N-acetylglucosaminyl transferase) (OGT), insulin-like growth factor 1 receptor (IGF1R) and one cut homeobox 2 (ONECUT2).

As used herein, the term "epidermal growth factor receptor (EGFR)" refers to the cell surface protein that binds to specific ligands [e.g. epidermal growth factor (EGF) and transforming growth factor α (TGFα)]. An exemplary EGFR is set forth in NP_005219.2, NP_958439.1, NP_958440.1, NP_958441.1 and in SEQ ID NO: 43 or SEQ ID NO: 42 encoding same.

As used herein, the term "insulin-degrading enzyme (IDE)" refers to the zinc-binding protease which cleaves multiple short polypeptides (e.g. insulin, glucagon, amylin, bradykinin, and kallidin). An exemplary IDE is set forth in NP_001159418.1, NP_004960.2 and in SEQ ID NO: 45 or SEQ ID NO: 44 encoding same.

As used herein, the term "insulin receptor substrate 1 (IRS1)" refers to the protein which is phosphorylated by insulin receptor tyrosine kinase and is involved in transmitting signals from the insulin and insulin-like growth factor-1 (IGF-1) receptors to intracellular pathways. An exemplary IRS1 is set forth in NP_005535.1 and in SEQ ID NO: 53 or SEQ ID NO: 52 encoding same.

As used herein, the term "insulin receptor substrate 2 (IRS2)" refers to the cytoplasmic signaling molecule that mediates effects of polypeptides (e.g. insulin, insulin-like growth factor 1, cytokines) by acting as a molecular adaptor between diverse receptor tyrosine kinases and downstream effectors. An exemplary IRS2 is set forth in NP_003740.2 and in SEQ ID NO: 47 or SEQ ID NO: 46 encoding same.

As used herein, the term "Kruppel-like factor 4 (KLF4)" refers to transcriptional activator or repressor [also known as gut-enriched Krüppel-like factor (GKLF)]. An exemplary KLF4 is set forth in NP_004226.3 and in SEQ ID NO: 49 or SEQ ID NO: 48 encoding same.

As used herein, the term "GLI family zinc finger 3 (GLI3)" refers to the zinc finger protein typically characterized as a DNA-binding transcription factor. An exemplary GLI3 is set forth in NP_000159.3 and in SEQ ID NO: 51 or SEQ ID NO: 50 encoding same.

As used herein, the term "Sp1 transcription factor (SP1)" refers to the zinc finger transcription factor that binds to GC-rich motifs of many promoters. An exemplary SP1 is set forth in NP_001238754.1, NP_003100.1, NP_612482.2 and in SEQ ID NO: 55 or SEQ ID NO: 54 encoding same.

As used herein, the term "O-linked N-acetylglucosamine (GlcNAc) transferase (UDP-N-acetylglucosamine:polypeptide-N-acetylglucosaminyl transferase) (OGT)" refers to the glycosyltransferase that catalyzes the addition of a single N-acetylglucosamine in O-glycosidic linkage to serine or threonine residues. An exemplary OGT is set forth in NP_858058.1, NP_858059.1 and in SEQ ID NO: 57 or SEQ ID NO: 56 encoding same.

As used herein, the term "insulin-like growth factor 1 receptor (IGF1R)" refers to the receptor which binds insulin-like growth factor. An exemplary IGF1R is set forth in NP_000866.1 and in SEQ ID NO: 59 or SEQ ID NO: 58 encoding same.

As used herein, the term "one cut homeobox 2 (ONECUT2)" refers to the transcription factors, which are typically characterized by a cut domain and an atypical homeodomain. An exemplary ONECUT2 is set forth in NP_004843.2 and in SEQ ID NO: 61 or SEQ ID NO: 60 encoding same.

Upregulation of a protein of a target gene of miR-7 of the present invention [e.g. epidermal growth factor receptor (EGFR), insulin-degrading enzyme (IDE), insulin receptor substrate 2 (IRK), Kruppel-like factor 4 (KLF4), GLI family zinc finger 3 (GLI3), insulin receptor substrate 1 (IRS1), Sp1 transcription factor (SP1), O-linked N-acetylglucosamine (GlcNAc) transferase (UDP-N-acetylglucosamine:polypeptide-N-acetylglucosaminyl transferase) (OGT), insulin-like growth factor 1 receptor (IGF1R) and one cut homeobox 2 (ONECUT2)] can be effected at the genomic level (i.e., activation of transcription via promoters, enhancers, regulatory elements), at the transcript level (i.e., correct splicing, polyadenylation, activation of translation) or at the protein level (i.e., post-translational modifications, interaction with substrates and the like).

Following is a list of agents capable of upregulating the expression level and/or activity of a protein of a target gene of miR-7 (e.g. EGFR, IDE, IRS2, KLF4, GLI3, IRS1, SP1, OGT, IGF1R and ONECUT2).

Upregulating expression of a polypeptide encoded by the target gene of miR-7 may be an exogenous polynucleotide sequence designed and constructed to express at least a functional portion of the protein of a target gene of miR-7. Accordingly, the exogenous polynucleotide sequence may be a DNA or RNA sequence encoding a target gene molecule, capable of increasing insulin content in a beta cell or stem cell.

As used herein, the phrase "polypeptide" encompasses a naturally occurring polypeptide which is comprised solely of natural amino acid residues or synthetically prepared polypeptides, comprised of a mixture of natural and modified (non-natural) amino acid residues as described hereinabove.

The phrase "functional portion" as used herein refers to part of the target gene protein (i.e., a polypeptide) which exhibits functional properties of the enzyme such as binding to a substrate. Thus, for example, a functional portion of EGFR comprises the kinase domain and C-terminal sequence for docking of signaling molecules and the functional portion of IGF1R comprises the tyrosin kinase domain.

To express exogenous target genes of miR-7 (e.g. EGFR, IDE, IRS2, KLF4, GLI3, IRS1, SP1, OGT, IGF1R or ONECUT2) in mammalian cells, a polynucleotide sequence encoding a target genes of miR-7 (e.g. EGFR, IDE, IRS2, KLF4, GLI3, IRS1, SP1, OGT, IGF1R or ONECUT2) is preferably ligated into a nucleic acid construct suitable for mammalian cell expression. Such a nucleic acid construct includes a promoter sequence for directing transcription of the polynucleotide sequence in the cell e.g., beta cell or stem cell-specific promoter in a constitutive or inducible manner.

It will be appreciated that the nucleic acid construct of some embodiments of the invention can also utilize homologues of target genes of miR-7 (e.g. EGFR, IDE, IRS2, KLF4, GLI3, IRS1, SP1, OGT, IGF1R or ONECUT2) which exhibit the desired activity (i.e., increase in insulin content). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 42 (EGFR); SEQ ID NO: 44 (IDE); SEQ ID NO: 46 (IRS2); SEQ ID NO: 48 (KLF4); SEQ ID NO: 50 (GLI3); SEQ ID NO: 52 (IRS1); SEQ ID NO: 54 (SP1); SEQ ID NO: 56 (OGT); SEQ ID NO: 58 (IGF1R); and SEQ ID NO: 60 (ONECUT2), as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV).

Nucleic acid construct suitable for use according to the present teachings are described in further detail hereinabove.

An agent capable of upregulating a protein of a target gene of miR-7 (e.g. EGFR, IDE, IRS2, KLF4, GLI3, IRS1, SP1, OGT, IGF1R and ONECUT2) may also be any compound which is capable of increasing the transcription and/or translation of an endogenous DNA or mRNA encoding the protein of a target gene of miR-7 (e.g. EGFR, IDE, IRS2, KLF4, GLI3, IRS1, SP1, OGT, IGF1R and ONECUT2) and thus increasing endogenous activity thereof. Thus, for example, Glucagon-like peptide-1 (GLP-1, e.g. as set forth in NP_002045.1) or Gastric inhibitory polypeptide (GIP, e.g. as set forth in NP_004114.1) may be used to upregulate expression of IRS1 and IRS2.

Measuring insulin content following expression of the target gene of miR-7 may be carried out using any method known in the art and as described in further detail hereinabove.

It will be appreciated that downregulation of miR-7 or expression of a target gene of miR-7 in pancreatic beta cells (e.g. precursor beta cells) or stem cells may further lead to proliferation or differentiation of these cells. Alternatively, downregulation of miR-7 (or expression of a target gene of miR-7) may be used to enhance differentiation or proliferation of pancreatic alpha cells. Such cells may be used as experimental models for further investigation of these cell types.

According to one embodiment, there is provided an isolated population of cells generated according to the above described methods.

According to another embodiment, there is provided an isolated population of cells comprising an exogenous agent for downregulating an activity or expression of mirR-7, wherein the cells secrete insulin.

For ex-vivo therapy, beta cells (e.g. precursor beta cells) or stem cells are preferably treated with the agent of the present invention (as detailed in further detail hereinabove), following which they are administered to the subject in need thereof.

Administration of the ex-vivo treated cells of the present invention (e.g. mature beta cells, precursor beta cells or stem cells) can be effected using any suitable route of introduction, such as intravenous, intraperitoneal, intra-kidney, intra-gastrointestinal track, subcutaneous, transcutaneous, intramuscular, intracutaneous, intrathecal, epidural, and rectal. According to presently preferred embodiments, the ex-vivo treated cells of the present invention may be introduced to the individual using intravenous, intra-kidney, intra-gastrointestinal track, and/or intraperitoneal administration.

The beta cells or stem cells may be obtained from any autologous or non-autologous (i.e., allogeneic or xenogeneic) donor. For example, cells may be isolated from a human cadaver or from a human pancreatic cell donor. Alternatively, cells may be obtained from any xenogeneic donor (e.g. porcine origin).

Beta cells or stem cells of xenogeneic origing (e.g. porcine) are preferably obtained from a source which is known to be free of zoonoses, such as porcine endogenous retroviruses. Similarly, human-derived beta cells or stem cells are preferably obtained from substantially pathogen-free sources.

Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation. Alternatively, cells may be uses which do not express xenogenic surface antigens, such as those developed in transgenic pigs.

Encapsulation techniques are generally classified as microencapsulation, involving small spherical vehicles, and macroencapsulation, involving larger flat-sheet and hollow-fiber membranes (Uludag, H. et al. (2000). Technology of mammalian cell encapsulation. Adv Drug Deliv Rev 42, 29-64).

Methods of preparing microcapsules are known in the art and include for example those disclosed in: Lu, M. Z. et al. (2000). Cell encapsulation with alginate and alpha-phenoxy-cinnamylidene-acetylated poly(allylamine). Biotechnol Bioeng 70, 479-483; Chang, T. M. and Prakash, S. (2001) Procedures for microencapsulation of enzymes, cells and genetically engineered microorganisms. Mol Biotechnol 17, 249-260; and Lu, M. Z., et al. (2000). A novel cell encapsulation method using photosensitive poly(allylamine alpha-cyanocinnamylideneacetate). J Microencapsul 17, 245-521.

For example, microcapsules are prepared using modified collagen in a complex with a ter-polymer shell of 2-hydroxyethyl methylacrylate (HEMA), methacrylic acid (MAA), and methyl methacrylate (MMA), resulting in a capsule thickness of 2-5 μm. Such microcapsules can be further encapsulated with an additional 2-5 μm of ter-polymer shells in order to impart a negatively charged smooth surface and to minimize plasma protein absorption (Chia, S. M. et al. (2002). Multi-layered microcapsules for cell encapsulation. Biomaterials 23, 849-856).

Other microcapsules are based on alginate, a marine polysaccharide (Sambanis, A. (2003). Encapsulated islets in diabetes treatment. Diabetes Thechnol Ther 5, 665-668), or its derivatives. For example, microcapsules can be prepared by the polyelectrolyte complexation between the polyanions sodium alginate and sodium cellulose sulphate and the polycation poly(methylene-co-guanidine) hydrochloride in the presence of calcium chloride.

It will be appreciated that cell encapsulation is improved when smaller capsules are used. Thus, for instance, the quality control, mechanical stability, diffusion properties, and in vitro activities of encapsulated cells improved when the capsule size was reduced from 1 mm to 400 µm (Canaple, L. et al. (2002). Improving cell encapsulation through size control. J Biomater Sci Polym Ed 13, 783-96). Moreover, nanoporous biocapsules with well-controlled pore size as small as 7 nm, tailored surface chemistries, and precise microarchitectures were found to successfully immunoisolate microenvironments for cells (See: Williams, D. (1999). Small is beautiful: microparticle and nanoparticle technology in medical devices. Med Device Technol 10, 6-9; and Desai, T. A. (2002). Microfabrication technology for pancreatic cell encapsulation. Expert Opin Biol Ther 2, 633-646).

Examples of immunosuppressive agents which may be used in conjunction with the ex-vivo treatment include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

According to another embodiment of the present invention, treating a medical condition associated with an insulin deficiency is effected by administering to the subject the agent per se for downregulating an activity or expression of miR-7.

For in-vivo therapy, the agent (as detailed in further detail hereinabove) is administered to the subject as is or as part of a pharmaceutical composition.

According to one embodiment, expression vectors are used for in-vivo expression of the miR-7 downregulating agents (i.e. in-vivo therapy).

As specified in further detail above, any mammalian expression vectors may be used for in-vivo therapy. Moreover, the expression vectors may comprise any additional sequences which render the vectors suitable for in-vivo expression agents in pancreatic beta cells (e.g. promoters, enhancers etc.).

Typically, recombinant viral vectors are useful for in-vivo expression of miR-7 downregulating agents since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Thus, the ex-vivo treated beta cells or stem cells or the miR-7 downregulating agent of the present invention can be administered to the individual per se or as part of a pharmaceutical composition which also includes a physiologically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (miR-7 downregulating agent) effective to prevent, alleviate or ameliorate symptoms of a disorder (e.g., insulin related disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide ample levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc. The dosage and timing of administration will be responsive to a careful and continuous monitoring of the individual changing condition.

It will be appreciated that animal models exist by which the agents of the present invention may be tested prior to human treatment. For example, Type I diabetes models include, pancreatectomy in dogs, spontaneous rodent models (e.g. BBDP rats and the NOD mice). Type II diabetes models and obese animal models include, db/db (diabetic)

mice, Zucker diabetic fatty (ZDF) rats, sand rats (Psammomys obesus) and obese rhesus monkeys.

Regardless of the above, the ex-vivo treated beta cells or stem cells or the miR-7 downregulating agent of the present invention are administered at an amount selected to avoid unwanted side-effects associated with elevated concentrations thereof.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The agents of the invention can be suitably formulated as pharmaceutical compositions which can be suitably packaged as an article of manufacture. Such an article of manufacture comprises a label for use in treating an insulin related disease (e.g. diabetes), the packaging material packaging a pharmaceutically effective amount of the beta cells or stem cells or the miR-7 downregulating agent.

It will be appreciated that each of the agents or compositions of the present invention may be administered in combination with other known treatments, including but not limited to, insulin including short-acting insulin [e.g. lispro (Humalog) or aspart (NovoLog)] and longer acting insulin [e.g. Neutral Protamine Hagedorn (NPH), Lente, glargine (Lantus), detemir, or ultralente] and oral medication for control of blood sugar levels e.g. sulfonylurea or biguanide [metformin (Glucophage)].

The agents or compositions of the present invention may be administered prior to, concomitantly with or following administration of the latter.

In order to test treatment efficacy, the subject may be evaluated by physical examination as well as using any method known in the art, as for example, by finger stick blood glucose test, fasting plasma glucose test, oral glucose tolerance test, glycosylated hemoglobin or hemoglobin A1c, body mass index (BMI) and the like.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Animals

Mice were housed and handled in accordance with protocols approved by the Institutional Animal Care of Weizmann Institute of Science Ethics Committee. Conditional miR-7 transgenic mice were generated as previously described [Srinivas et al. (2001) BMC Dev Biol (1) 4]. Briefly, a 500 bp fragment flanking the miR-7-1a gene was cloned into the Rosa26 locus downstream of the PGK promoter and a transcriptional STOP cassette and upstream of IRES-EGFP-polyadenylation signal. Correct homologous recombination onto the ROSA26 locus was identified by southern blot analysis to embryonic stem cell colonies (129/SvEv). Scanning 209 colonies identified 29 positive colonies and the mouse line was derived through blastocyst injection (C57BL6/J background). Rosa-miR-7 mice were crossed to a Pdx1-Cre transgene and mated to homozygousity. Other mouse strains used in this study were Ngn3-CreER, serving as Ngn3 nulls [previously described by Wang et al., *Dev. Biol.* (2010) 339: 26-37] and a Pax6 null allele [previously described by St-Onge et al., *Nature* (1997) 387: 406-409].

Organ Culture

Dorsal pancreatic rudiments of E12.5 ICR mouse embryos were dissected from the adjacent mesenchyme, using a tungsten needle. The explants were cultured in M199 medium supplemented with 10% fetal bovine serum (GIBCO), 2 mM L-glutamine, 100 U/mL penicillin/streptomycin. Individual explants were plated in 30 µl inverted 'hanging drops' on a 35-mm Petri dish cover (NUNC), with medium containing either antagomirs (Dharmacon) or cholesterol conjugated miRNA mimics (IDT) at 1 µM. The exact sequences of the oligos are depicted in Table 1, below. Explants were further grown for up to 48 hr at 37° C. with a 5% $CO_2$ in a humidified incubator. BrdU (3 µg/ml) was added to the medium 1 hour before harvest for analysis of proliferation.

TABLE 1

Sequences of primers and oligos

| Gene name | Forward Primer | Reverse Primer |
|---|---|---|
| Pax6 | AACAACCTGCCTATGCAA CC (SEQ ID NO: 1) | ACTTGGACGGGAACTGACAC (SEQ ID NO: 2) |
| Insulin | CCTGTTGGTGCACTTCCTAC (SEQ ID NO: 3) | TGCAGTAGTTCTCCAGCTGG (SEQ ID NO: 4) |
| Glucagon | AAACCAAGATCACTGACAAGA AATAGGT (SEQ ID NO: 5) | TTTGAAATTGTACATCCCAA GTGAC (SEQ ID NO: 6) |
| Ghrelin | CAGGCTCCAGCTTCCTGA (SEQ ID NO: 29) | GTGGCTGCAGTTTAGCTGGT (SEQ ID NO: 30) |
| Pdx1 | TTCCCGAATGGAACCGAGC (SEQ ID NO: 7) | GTAGGCAGTACGGGTCCTCT (SEQ ID NO: 8) |
| Pax4 | ACCTCATCCCAGGCCTATCTC (SEQ ID NO: 9) | TGAGGAGGAAGCCACAGGA A (SEQ ID NO: 10) |
| Cpa1 | CAGATCGGCAGCACCTTTGAA (SEQ ID NO: 11) | GACCCACTCCCTGGAATGGA (SEQ ID NO: 12) |
| Ptf1a | TCCCATCCCCTTACTTTGATGA (SEQ ID NO: 13) | GTAGCAGTATTCGTGTAGCT GG (SEQ ID NO: 14) |
| Gapdh | TGGCAAAGTGGAGATTGTTGCC (SEQ ID NO: 15) | AAGATGGTGATGGGCTTCCC G (SEQ ID NO: 16) |
| Hprt | CTGGTTAAGCAGTACAGCCCCA AA (SEQ ID NO: 17) | TGGCCTGTATCCAACACTTC GAGA (SEQ ID NO: 18) |

TABLE 1-continued

Sequences of primers and oligos

| Gene name | Forward Primer | Reverse Primer |
|---|---|---|
| Anti-miR-7 antagomir (2'OH)-chl | ApsCpsAACAAAAUCACUAGUC UUpsCpsCpsAps-Chol (SEQ ID NO: 19) | |
| Anti-miR-122 antagomir (2'OH)-chl | ApsCpsAAACACCAUUGUCACAC UpsCpsCpsAps-Chol (SEQ ID NO: 20) | |
| MafB | CGTCCTTCCTCCCTCTAGCTC (SEQ ID NO: 31) | ACTCCCTGTCCCTGCCATG (SEQ ID NO: 32) |
| Arx | CAGCATTTGGCAGGCTCT (SEQ ID NO: 33) | AGGATGTTGAGCTGCGTGAG (SEQ ID NO: 34) |
| siPAx6 | ACCAUGAUCGACAAGAUUUGCCAT (SEQ ID NO: 35) | |

Pancreas Histology and Quantification Analysis

Immunofluorescence of paraffin sections was carried out as previously described [Melkman-Zehavi et al. EMBO J. (2011) 30(5):835-45]. Whole-explants staining was carried out as previously described [Kredo-Russo, S. and Hornstein, E. (2011) Methods Mol Biol, 732, 89-97]. The primary antibodies used were: rabbit anti-Pax6 (1:300, Covanc), guinea pig anti-insulin (1:200, Dako), rabbit anti-glucagon (1:200, Dako). Secondary antibodies used were: Cy2-Cy3- or Cy5-conjugated donkey anti-guinea pig, anti-mouse, and anti-rabbit IgG (1:200, Jackson ImmunoResearch). Nuclei were stained with Dapi (1: 10,000, Molecular Probes). Whole-mount BrdU analysis that included a 2 hour DNase I treatment was carried out as previously described [Tkatchenko A. V., Biotechniques (2006) 40: 29-30, 32].

Fluorescent confocal images were captured with a Zeiss LSM 510 microscope, using an optical depth of 1 μm, with at least 6-8 optical sections at 5 μm intervals throughout the whole organ.

Morphometry of the explants was performed by quantification of the immunostained area from the entire explant sections from a minimum of three mutants and three wild-type matched littermates. Total tissue area and total hormone-positive area, were calculated using Niss-elements' software (Nikon) [Garofano et al. (1998) Diabetologia, 41, 1114-1120].

For cell number quantification at E15.5, hormone-positive cells were manually counted every fifth section throughout the whole pancreas anlagen. Data were the average number of cells/section in multiple sections and were analyzed for four or more individual animals per genotype. Cell number analysis of total hormone-positive cells in whole E12.5 explants was performed manually, by counting cells in six stacked z-section confocal images, spanning the whole explants.

Quantitative PCR for miRNA and mRNA

Extraction of total RNA was carried out by the miRNeasy Mini Kit (QIAGEN). Synthesis of mRNA cDNA was created using an oligo d(T) primer (Promega) and SuperScript II reverse transcriptase (Invitrogen). Synthesis of miRNA cDNA was created using Taqman MicroRNA qPCR Assays (Applied Biosystems). qPCR analysis was performed on LightCycler® 480 System (Roche) using Kapa™ SYBR® Green qPCR kit (Finnzymes). miRNA and mRNA levels were normalized to the expression of small RNAs (sno234 and U6) or mRNA (Gapdh and Hprt), respectively. Primer sequences are described in Table 1, above.

miRNA In Situ Hybridization

Paraffin sections of E15.5 pancreata were hybridized with DIG-labeled LNA probes (Exiqon) overnight at 48° C. (miR-7) or 54° C. (U6, control) as previously described [Pena et al. (2009) Nat Methods (6) 139-141] and developed with TSA kit (PerkinElmer) as previously described [Silahtaroglu et al. (2007) Nat Protoc (2) 2520-2528]. When in situ hybridization was combined with immunoflourescence, primary antibody was added to the Anti-Dig-POD incubation (1:500 Roche).

Cell Culture, Luciferase Reporter Assay and Western Blotting

HEK-293T cells (American Type Culture Collection) and MIN6 cells were grown in Dullbecco's modified Eagle medium (DMEM) with 10% FBS, 2 mM L-glutamine, 100 U/mL penicillin/streptomycin at 37° C.; 5% CO2 in a humidified incubator. Experiments on MIN6 cells were performed between passages 18 to 28.

A 742 bp fragment of the mouse Pax6 3'UTR sequence (chr2 105536551-105537201) was subcloned into psi-CHECK-2 Vector (Promega) and transfected into HEK-293T cells. Dual-Reporter luciferase assay was performed 48 hr later, according to the manufacturers' instructions (Promega).

miR-7 overexpression was achieved using expression vectors miRVec-miR-7 or miRVec control. miR-7 knock-down was carried out using oligos against miR-7 or against scrambled sequence, as negative control oligos (50 nM, Ambion), using Lipofectamine 2000 Reagent (Invitrogen).

For western blots, cellular lysate was subject to 10% SDS-PAGE and immunoblotted with rabbit anti-Pax6 (1:5,000 Chemicon), mouse anti-GAPDH (1:10000, Ambion) and quantified with ImageJ software.

For analysis of insulin transcription, firefly luciferase reporter driven by the rat insulin promoter and an A20-*Renilla* luciferase construct were transfected using Lipofectamine 2000 Reagent Invitrogen) to MIN6 cells. Anti miR-7 oligo (100 nM) and Pax6 siRNA 10 nM) were from IDT;

Statistical Analysis

Analysis was performed using either Student's t-test or two-way ANOVA by the JMP software. Results were provided as mean±SEM. The null hypothesis was rejected at the 0.05 level (**) or 0.01 (*). Gene Ontology analysis was performed using DAVID (as previously described by Dennis et al. *Genome Biol*. (2003) 4, P3].

Example 1 miR-7 is Expressed in the Endocrine Cells of the Pancreas

To determine the spatial expression pattern of miR-7, the present inventors carried out in situ hybridization combined with immunofluorescent protein detection on E12.5-E15.5 pancreatic sections, using a digoxigenin (DIG)-labeled LNA probe. At this time point, called 'secondary transition', many endocrine cells are generated within the pancreatic epithelium. Bright field analysis revealed that miR-7 expression was restricted to a subset of clustered epithelial cells at the "trunk" compartment of the branching pancreatic epithelium (FIGS. 1A-B). To identify in higher resolution what cell types expressed miR-7, the present inventors carried out fluorescence in situ hybridization. This experiment revealed clusters of miR-7 expressing cells (FIG. 1C). The hybridization pattern was specific to miR-7 and could not be detected with a probe against the ubiquitously-expressed small RNA U6 or a scrambled miRNA sequence (FIGS. 1D-E). Fluorescence in situ hybridization combined with immunostaining of endocrine proteins demonstrated co-localization of miR-7 with insulin and glucagon in differentiating β- and α-cells, respectively (E13.5-E15.5; FIGS. 1F-H). miR-7 and Cpa1 expression domains were mutually exclusive at E15.5 (FIGS. 1I-K), as were miR-7 and Hnf1β at E14.5 (FIGS. 1L-N). These data indicate that miR-7 was not expressed in differentiated acinar or duct cells. To examine miR-7 expression in endocrine precursor cells, immunostaining of Ngn3 was performed. At E12.5, E13.5 and E14.5, miR-7 was colocalized with many Ngn3-positive cells (FIGS. 1O-T), suggesting that miR-7 was induced in newly born endocrine cells. Independent genetic support to this study came from the analysis of Ngn3-null pancreata. It was previously shown that Ngn3-deficient embryos completely lack endocrine hormone-producing cells [Gradwohl G. et al., *Proc. Natl. Acad. Sci. USA* (2000) 97: 1607-1611]. Consistent with this, the expression of endocrine markers, such as Pax6 and insulin, was downregulated in Ngn3-null pancreata (FIG. 1U). As miR-7 expression was also abrogated in E14.5 Ngn3-null pancreas, the present inventors concluded that this miRNA is specifically expressed within the endocrine lineage. Furthermore, this regulation was specific to miR-7, as the expression of miR-17 and Let-7b was not changed (FIG. 1U). Notably, miR-375, another pancreatic miRNA, was also downregulated in Ngn3-null pancreata, yet some residual expression was maintained, unlike miR-7 (FIG. 1U). Altogether, this analysis revealed the endocrine-specific expression pattern of miR-7, wherein miR-7 is induced in Ngn3+ precursors and is maintained in the differentiated endocrine cells.

Example 2

Pax6 is a miR-7 Target

To identify potential miR-7 targets that play a role in pancreas development, two unbiased bioinformatic approaches were employed. First, 'gene ontology' (GO) was analyzed in terms related to miR-7 targets [DAVID, as previously described in Dennis G. et al., *Genome Biol*. (2003)4, P3]. Among the 237 predicted miR-7 targets [TargetScan as described in Lewis et al. (2005) *Cell*, 120, 15-20], the GO term 'Regulation of transcription' was found to be the most significantly enriched (52 genes, $P<2.35E^{-7}$). Intriguingly, within this list, Pax6 was the only established pancreatic transcription factor (see Tables 2-4, below, and FIG. 2A). Furthermore, the binding site for miR-7 at the Pax6 mRNA 3' untranslated region (3' UTR) is predicted to be strong and conserved (FIG. 2B), Independently, an interaction map was built of miRNAs with the 3' UTRs of transcription factors that are known to control pancreas development, including Pdx1, Ngn3, Nkx2.2, Nkx6.1, MafB, Pax4, Pax6, Arx, Hnf1b and Hnf6 (for a comprehensive list see Tables 2-4, below). This approach provided a wealth of potential interactions, however, Pax6 was the only miR-7 predicted target. As Pax6 expression is known to be tightly regulated in many organs, the present inventors hypothesized that miR-7 may be a new endocrine regulatory gene upstream of Pax6.

TABLE 2

Genes related to pancreas differentiation and their predicted targets

| Predicted targeting miRNAs | | |
|---|---|---|
| PicTar | TargetScan-mouse | Gene name |
| none conserved sites | none conserved sites | Pdx1/IPF1 |
| miR-106b<br>miR-106a<br>miR-294<br>miR-124a<br>miR-20b<br>miR-20a<br>miR-291b-3p<br>miR-291a-3p<br>miR-17-5p<br>miR-295<br>miR-93 | none conserved sites | Ngn3 (neurogenin 3) |
| mmu-miR-452 | miR-133<br>miR-30a/30a-5p<br>miR-182<br>miR-17-5p/20/93/106/519<br>miR-26ab<br>miR-96<br>miR-374<br>miR-342<br>miR-377 | NKX2-2 |
| none conserved sites | No predictions (short 3'UTR) | NKX6-1 |
| mmu-miR-130a<br>mmu-miR-130b<br>mmu-miR-188<br>mmu-miR-29a<br>mmu-miR-29b<br>mmu-miR-301<br>mmu-miR-29c<br>mmu-miR-338<br>mmu-miR-148b<br>mmu-miR-152<br>mmu-miR-148a<br>mmu-miR-199b<br>mmu-miR-199a<br>mmu-miR-485-3p<br>mmu-miR-155<br>mmu-miR-126-5p<br>mmu-miR-223<br>mmu-miR-192<br>mmu-miR-186 | miR-148/152<br>miR-338/338-3p<br>miR-29abc<br>miR-130/301<br>miR-223<br>miR-155<br>miR-203 | MafB |
| mmu-miR-365<br>mmu-miR-7<br>mmu-miR-7b<br>mmu-miR-129-5p<br>mmu-miR-300<br>mmu-miR-450<br>mmu-miR-375 | miR-365<br>miR-7<br>miR-129/129-5p<br>miR-375<br>miR-196<br>miR-96<br>miR182 | Pax6 |

TABLE 2-continued

Genes related to pancreas differentiation and their predicted targets

| Predicted targeting miRNAs | | |
|---|---|---|
| PicTar | TargetScan-mouse | Gene name |
| none conserved sites | none conserved sites | Pax4 |
| none conserved sites | miR-204 miR-96 miR-132/212 miR-27ab miR-300 miR-130/301 miR-139-5p | Arx |
| none conserved sites | miR-200bc/429 miR-375 miR-194 miR-24 miR-25/32/92/363/367 | HNF1b |
| none conserved sites | mmu-miR-320 | Onecut1 (HNF6) |

TABLE 3

Gene Ontology analysis of predicted miR-7 targets

| calculated Pvalue for term and corrected P values | | | | | | | % of total predicted miR-7 targets | Count (nos. of genes in this term category) | Term |
|---|---|---|---|---|---|---|---|---|---|
| FDR | Benjamini | Bonferroni | Fold Enrichment | Pop Total | Pop Hits | P-value | | | |
| 3.77E−04 | 2.68E−04 | 2.68E−04 | 2.046948738 | 13588 | 2227 | 2.35E−07 | 24.3 | 52 | GO: 0045449 ~regulation of transcription |
| 0.002706436 | 9.62E−04 | 0.00192331 | 3.273188102 | 13588 | 616 | 1.68E−06 | 10.7 | 23 | GO: 0006357 ~regulation of transcription from RNA polymerase II promoter |
| 0.002859408 | 6.78E−04 | 0.00203191 | 3.691137521 | 13588 | 475 | 1.78E−06 | 9.3 | 20 | GO: 0045941 ~positive regulation of transcription |
| 0.003662215 | 6.51E−04 | 0.002601657 | 3.473499696 | 13588 | 530 | 2.28E−06 | 9.8 | 21 | GO: 0010557 ~positive regulation of macromolecule biosynthetic process |
| 0.004253361 | 6.05E−04 | 0.003020984 | 3.592808038 | 13588 | 488 | 2.65E−06 | 9.3 | 20 | GO: 0010628 ~positive regulation of gene expression |
| 0.006460509 | 7.66E−04 | 0.00458508 | 3.848686074 | 13588 | 410 | 4.02E−06 | 8.4 | 18 | GO: 0010629 ~negative regulation of gene expression |
| 0.006777121 | 6.88E−04 | 0.004809249 | 3.335063114 | 13588 | 552 | 4.22E−06 | 9.8 | 21 | GO: 0031328 ~positive regulation of cellular biosynthetic process |
| 0.007079523 | 6.29E−04 | 0.00502331 | 2.077827132 | 13588 | 1772 | 4.41E−06 | 19.6 | 42 | GO: 0006350 ~transcription |

TABLE 4 miR-7 predicted targets under Gene Ontology Term "Regulation of Transcription" (*mus musculus*)
Regulation of transcription

| Gene Name | Gene ID |
| --- | --- |
| BCL6 co-repressor-like 1 | 453169 |
| CCR4-NOT transcription complex, subunit 8 | 460864 |
| CGG triplet repeat binding protein 1 | 451590 |
| GATA binding protein 6 | 472801 |
| GATA zinc finger domain containing 2B | 470085 |
| GLI-Kruppel family member GLI3 | 442692 |
| Kruppel-like factor 12 | 452902 |
| Kruppel-like factor 4 (gut) | 439346 |
| PHD finger protein 17 | 443767 |
| PHD finger protein 21A | 422523 |
| RIKEN cDNA D930049A15 gene; zinc finger, MIZ-type containing 1 | 424115 |
| SET domain containing (lysine methyltransferase) 8; predicted gene 8590 | 465940 |
| additional sex combs like 1 (*Drosophila*) | 468967 |
| bromodomain and WD repeat domain containing 1 | 434997 |
| catenin (cadherin associated protein), delta 1 | 424730 |
| cone-rod homeobox containing gene | 439284 |
| dachshund 1 (*Drosophila*) | 467246 |
| early growth response 3 | 454142 |
| estrogen-related receptor gamma | 477434 |
| eukaryotic translation initiation factor 2C, 1 | 467835 |
| forkhead box N3 | 480126 |
| helicase, lymphoid specific | 477958 |
| homeodomain interacting protein kinase 2 | 445147 |
| inhibitor of growth family, member 5 | 430151 |
| methyl CpG binding protein 2 | 426701 |
| methyl-CpG binding domain protein 2 | 480586 |
| nuclear factor I/B | 479694 |
| nuclear receptor subfamily 1, group H, member 2 | 445414 |
| nuclear receptor subfamily 4, group A, member 3 | 457788 |
| paired box gene 6 | 431410 |
| poly (ADP-ribose) polymerase family, member 1 | 443346 |
| purine rich element binding protein B | 424173 |
| ras responsive element binding protein 1 | 459023 |
| retinoblastoma 1 | 427771 |
| similar to PBX3a; pre B-cell leukemia transcription factor 3 | 460161 |
| similar to Zinc finger and BTB domain containing 1; zinc finger and BTB domain containing 1 | 449895 |
| similar to mKIAA0658 protein; cryptochrome 2 (photolyase-like) | 422529 |
| similar to mafG; v-maf musculoaponeurotic fibrosarcoma oncogene family, protein G (avian) | 459027 |
| sine oculis-related homeobox 4 homolog (*Drosophila*) | 461708 |
| special AT-rich sequence binding protein 1 | 424985 |
| trans-acting transcription factor 1 | 481531 |
| transcription factor 12 | 475056 |
| transcription factor 4 | 482380 |
| v-maf musculoaponeurotic fibrosarcoma oncogene family, protein K (avian) | 470659 |
| zinc fingers and homeoboxes 3 | 452440 |

\* Of note, Table 2 is a bioinformatic analysis of mRNAs encoding for proteins involved in pancreas development, with respect to conserved miRNA binding sites in their 3'UTRs. Predictions are based on TargetScans and PicTar. Table 3 is a gene Ontology (GO) analysis of miR-7 conserved targets, and Table 4 depicts the genes listed under the GO term "Regulation of Transcription", among them is Pax6.

To determine whether miR-7 directly targets Pax6 3'UTR the present inventors performed a heterologous reporter assay. The whole 3'UTR of Pax6 (742 bp) was cloned into a dual luciferase reporter vector and introduced into HEK-293T cells along with expression vector for miR-7 (miRvec-7) or a miRNA control vector (harboring a random and non-targeting miRNA-like sequence: 'Ctrl'). Overexpression of miR-7 significantly decreased luciferase activity relative to negative control (FIG. 2C, pink bar; reduced to 62%). The addition of an anti-miRNA oligo partially blocked this repression, supporting the functionality of the predicted miR-7 binding site. Moreover, when inventors introduced a 3'UTR mutant sequences, in which 6 nucleotides of the potential 'seed' binding-site were eliminated (marked in red, FIG. 2B), miR-7-dependent repression was completely abolished (FIG. 2C). To determine whether miR-7 represses the expression of endogenous Pax6, inventors transfected the beta cell line (MIN6) with miRvec-7. Overexpression of miR-7 decreased PAX6 protein levels to 60% relative to control miRvec, as measured by western blots. Consistently, inhibition of miR-7 by anti-miR-7 oligos significantly upregulated PAX6 protein levels (FIGS. 2D-G). Taken together, these results indicate that Pax6 is a bona fide target of miR-7 in beta cells.

Inventors next tested if miR-7 and its target Pax6 are co-expressed in the developmental context of endocrine differentiation. miR-7 in situ hybridization combined with Pax6 immunofluorescence revealed that miR-7 and Pax6 are indeed co-expressed in endocrine cell, allowing direct molecular interactions (FIGS. 2H-J). To quantify temporal dynamics of miR-7 and Pax6 expression, inventors performed qPCR on RNA extracted from E12.5-E15.5 pancreata. miR-7 levels increased in time, reaching maximal levels at E14.5. Intriguingly, inventors noted trend of reciprocal miR-7 and Pax6 expression in which miR-7 upregulation is associated with Pax6 downregulation (FIG. 2K).

Hence, miR-7-based attenuation may serve to progressively inhibit Pax6 expression levels as maturation of endocrine cells occurs.

Example 3 miR-7 Controls Endocrine Differentiation in Explants Culture

To determine the functional role of miR-7 in the endocrine lineage, inventors carried out gain- and loss-of function experiments in a primary pancreatic explant system (see schematic illustration in FIG. 3A). E12.5 pancreatic buds were cultured for 48 hrs under defined ex-vivo conditions, providing a reliable model for normal development [as previously described by Kredo-Russo, S. and Hornstein, E. (2011), supra]. Inventors detected typical Ngn3, insulin and miR-7 expression that recapitulated in-vivo differentiation, including the expected differentiation of alpha and beta cells (FIG. 4A-E).

To manipulate miR-7 expression in organ cultures, inventors used cholesterol-conjugated 2′-O-methyl (2′OMe) 'antagomirs' against miR-7 or miR-7 'mimic' oligos (termed 'miR-7 KD' and 'miR-7 OE', respectively). As 'non-targeting' negative controls, inventors used antagomirs against the liver specific miR-122, which is not expressed in the pancreas and miR-67-mimic, a nematode miRNA that is not expressed in vertebrates (termed 'Ctrl-KD or 'Ctrl-OE', respectively). First, inventors verified that a Cy-bound oligos is efficiently taken up by the explants (FIGS. 4F-H). Next, the functionality of miR-7 KD and miR-7 OE oligos was confirmed by co-transfecting them into HEK-293T with a miR-7 luciferase reporter that harbors multiple miR-7 binding sites on its 3′UTR [as previously described by Kefas et al. (2008) Cancer Res (68) 3566-3572]. Reporter luciferase activity was strongly suppressed by miR-7 overexpression, and this was reversed by co-transfecting miR-7 KD together with miR-7 OE oligos (FIG. 4I). Inventors then used this system to study miR-7-Pax6 interactions in pancreatic explants.

In explants treated with miR-7 KD, Pax6 mRNA levels were up-regulated by 2.5 fold, relative to control (FIG. 3B), whereas in explants treated with miR-7 OE, Pax6 mRNA levels were repressed to 60%, relative to control (FIG. 3M). Additionally, immunofluorescent analysis revealed reduction of PAX6 protein levels (FIGS. 4S-T). These results suggest functional regulation of Pax6 levels downstream of miR-7 in pancreas development.

Intriguingly, upon miR-7 KD, insulin and glucagon mRNAs levels were increased (insulin by 22% and glucagon by 61%, FIG. 3C). Accordingly, an increase in insulin protein content was demonstrated by ELISA measurement in miR-7 KD explants, relative to control (FIG. 3D). Furthermore, comprehensive morphometric analysis revealed a 20% increase in the insulin-positive area and in the number of insulin-positive cells. Similarly, 40% increase in the glucagon-positive area and in the number of glucagon-positive cells were found in miR-7 KD pancreata, relative to controls (FIGS. 3E-J, 3L and FIGS. 8A-J). However, Somatostatin expression in miR-7 KD was comparable with control (FIGS. 8A-J). To understand the potential causes for the increase in insulin and glucagon-positive cells, the proliferation capacity of endocrine cells was studied. The total numbers of BrdU-positive nuclei and the percentage of proliferating insulin-positive and glucagon-positive cells, measured by either Ki67 or BrdU, was comparable in miR-7 KD and control explants (FIGS. 9A-G). In addition, the numbers of Ngn3-positive progenitors, was not affected by miR-7 KD (FIGS. 8K-S) suggesting that the increase in insulin- and glucagon-positive cells emerges neither from enhanced proliferation, nor from changes in the size of the Ngn3 precursor pool.

Although Pax6 positively regulates insulin and glucagon expression, it negatively regulates ghrelin expression and differentiation of 8-cells. Accordingly, miR-7 KD resulted in reduced numbers of ghrelin-positive cells (FIGS. 3E-J, 3L and FIGS. 8A-J) supporting the view that miR-7 knockdown acts upstream of Pax6 to promote differentiation into insulin- and glucagon-positive cells at the expense of ghrelin-positive cells.

Inventors next quantified the expression levels of a set of transcription factors that are essential for beta and alpha-cell differentiation. This analysis revealed upregulation of Arx, which is specifically expressed in alpha cells and of the beta cell factors, Pax4 and MafB in miR-7 KD explants. However, the levels of the exocrine markers Cpa1 and Ptf1a were unchanged (FIG. 3K). Consistently, miR-7 OE resulted in downregulation of insulin and MafB mRNA levels, two genes that are directly controlled by Pax6, and in reduced beta cell mass (FIG. 3N-R). However, glucagon and Arx mRNA levels were not significantly changed. Taken together, these findings revealed that miR-7 negatively control differentiation and maturation of hormone-producing cells.

Example 4

Overexpression of miR-7 In-Vivo Reduced Expression of Endocrine Genes

To examine the consequences of miR-7 overexpression in-vivo, inventors generated a conditional miR-7 transgenic mouse line. miR-7a-1 genomic sequence was inserted by homologous recombination into the ubiquitously-expressed Rosa26 locus (FIGS. 5A-B) as previously described by Srinivas et al. (supra). In this knock-in model, the expression of miR-7 is coupled to the expression of enhanced green fluorescent protein (EGFP) and both are conditionally blocked by a 'Neo-STOP' cassette, flanked by LoxP sites. Thus, miR-7 and EGFP expression are induced only in tissues that express a Cre transgene. To validate the inducible expression of miR-7, inventors isolated mouse embryonic fibroblasts (MEFs) from Rosa26-miR-7 mice. Upon introduction of Cre recombinase by adenoviral vector, the expression of miR-7 was specifically up-regulated by 2 fold, whereas the level of an unrelated miRNA, miR-199, remained unchanged (FIG. 5C).

To stimulate the production of miR-7 early in the pancreatic lineage, inventors crossed the Rosa26-miR-7 allele to a Pdx1-Cre transgene. Pdx1-Cre; Rosa26-miR-7 mice specifically expressed GFP protein in E13.5 pancreas cells (FIGS. 5D-E), while littermates that did not harbor the Pdx1-Cre transgene did not express GFP (termed 'Ctrl').

Inventors next characterized the Pdx1-Cre; Rosa26-miR-7 mice by qPCR of E15.5 pancreata. The expression of the mature endocrine cell markers, insulin and glucagon was downregulated (insulin to 72%, glucagon to 68%). Quantification of the expression of transcription factors showed a reduction in Arx (reduced to 63%), Pax4 (reduced to 62%), and in the miR-7 target gene Pax6 (reduced to 49%, FIG. 5F). Notably, Cpa1 and Ptf1a levels were unchanged, indicating that the exocrine lineage was unaffected by miR-7 mis-expression in Pdx1-Cre; Rosa26-miR-7 mice. Immunostaining for insulin and glucagon on E15.5 pancreas sections revealed a decrease in the expression of endocrine markers (FIGS. 5G-J). Therefore, when miR-7 was overexpressed in Pdx1-Cre; Rosa26-miR-7 embryos, Pax6 levels decreased and the expression of insulin and glucagon was downregulated, providing in-vivo evidence for control of Pax6 by miR-7.

To elucidate the genetic interactions of miR-7 and Pax6, a luciferase reporter, driven by the insulin promoter was used as previously described [Melkman-Zehavi et al., (2011), supra]. As the insulin promoter is directly activated by Pax6, it provides a model system for monitoring the effect of miR-7-Pax6 axis on insulin expression. Transfecting MIN6 cells with either siRNA against Pax6 ('siPax6') or miR-7 overexpression vector ('miR-7 OE'), resulted in downregulation of insulin promoter activity, relative to scrambled siRNA, or empty miRvec, respectively (FIG. 5K). These results support the observed decrease in insulin mRNA expression by miR-7 OE in explants (FIG. 3N) and in miR-7 transgenic model (FIG. 5F). The combined effect of siPax6 together with miR-7 OE, significantly repressed the activity of the insulin promoter (FIG. 5K). Furthermore, transfecting MIN6 cells with knockdown oligos against miR-7 ('miR-7 KD') resulted in upregulation of insulin promoter activity, relative to scrambled oligos ('Ctrl KD'), consistent with insulin mRNA upregulation in miR-7 KD-treated explants (FIG. 5L).

However, when inhibited simultaneously, siPax6 reversed the effect of miR-7 KD, suggesting that Pax6 mediates miR-7 regulation of insulin expression (FIGS. 5K-L). These results stress the epistatic relationship of miR-7 upstream of Pax6, in the control of insulin expression. Taken together, when miR-7 is overexpressed, Pax6 levels are decreased and the expression of is down-regulated, consistent with the data obtained from explant studies. Therefore, miR-7 negatively regulates Pax6 and downstream endocrine differentiation. Inventors next studied the consequences of a genetic manipulation in the miR-7 target, Pax6.

Example 5

Pax6 Haplo-Insufficiency Resembles miR-7 Overexpression Phenotype

To examine the outcome of Pax6 downregulation by an independent mechanism, inventors analyzed Pax6 heterozygous pancreata (termed 'het'). These mice were generated by replacing the start codon and the entire paired domain with a beta-galactosidase gene as previously described by St-Onge [see FIG. 6A, St-Onge et al. (1997) *Nature* 387: 406-409]. qPCR analysis of mRNA, extracted from E15.5 Pax6 heterozygous pancreata showed a 50% reduction in Pax6 mRNA levels relative to wild-type littermate controls (termed 'wt', FIG. 6B). Immunostaining and quantification further revealed downregulation of protein expression at the cellular level (FIGS. 6C-E). While homozygous loss of Pax6 causes complete loss of insulin and of glucagon expression, here inventors show that in Pax6 heterozygote pancreata insulin and glucagon mRNA levels decreased by 65% and 30%, respectively (FIG. 6F). In addition, MafB levels were slightly downregulated in Pax6 heterozygouse (20% reduction), whereas Pdx1, Arx, Pax4 and Ptf1a remained unchanged relative to wt (FIG. 6G). In addition, serial confocal quantification revealed a 22% decrease in beta cells numbers, while alpha cell numbers remained unchanged (FIGS. 6H-J). These data revealed the sensitivity of MafB, insulin and glucagon expression to Pax6 levels. Moreover, Pax6 haplo-insufficiency phenocopied miR-7 overexpression, especially the predominant impact on insulin-expressing cells. Inventors next mapped miR-7 into the transcriptional network that specifies the endocrine cells.

Example 6 miR-7 Functions Upstream of Pax6 and is Dependent on Ngn3

To examine whether miR-7 and Pax6 reciprocally regulate each other, inventors quantified miR-7 levels in E15.5 Pax6 null pancreata by qPCR. miR-7 expression was not changed in Pax6 heterozygous or in homozygote null pancreata relative to wild-type littermate controls (FIG. 7A). Therefore, inventors conclude that miR-7 is not controlled by Pax6. To examine how miR-7 is activated upstream of Pax6, inventors quantified miR-7 levels in E15.5 Ngn3-null pancreata. Intriguingly, miR-7 expression was completely abrogated in Ngn3-null pancreas relative to littermate controls (FIG. 1F). This analysis demonstrated that miR-7 expression is dependent on the presence of Ngn3, providing a molecular mechanism for endocrine-specific expression of miR-7 (FIG. 7B). In summary, the presented data suggest that miR-7 acts downstream of Ngn3 to limit Pax6 expression levels, allowing endocrine cell maturation and precise development of the endocrine pancreas.

Taken together, the present inventors have discovered a miR-7-based mechanism that controls and refines Pax6 levels in the endocrine pancreas, through a conserved binding site in Pax6 mRNA 3'UTR. This mechanism enables correct insulin and glucagon expression and proper beta and alpha cell differentiation. The present inventors showed that miR-7 is expressed uniquely in the endocrine lineage and that its expression is up-regulated between mouse gestational ages E12.5-E15.5. Intriguingly, despite high expression levels, miR-7 serves an inhibitory factor in endocrine cell maturation. For example, miR-7 knockdown led to upregulation of endocrine markers. Conversely, overexpression of miR-7 repressed endocrine gene expression, mainly insulin. While miR-7 appears as an inhibitor of final differentiation, more likely it controls Pax6 levels in a temporal fashion, allowing higher levels of the transcription factor first and dampening its expression later (see model in FIG. 10). The present inventors have further demonstrated that miR-7 expression is dependent on Ngn3.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of ex-vivo increasing insulin content in primary beta cells, the method comprising contacting said primary beta cells with an agent for downregulating an activity or expression of miR-7, thereby increasing said insulin content in said primary beta cells.

2. A method of treating a medical condition associated with an insulin deficiency in a subject in need thereof having said insulin deficiency, the method comprising administering to the subject an agent for downregulating an activity or expression of miR-7, and wherein the medical condition associated with an insulin deficiency is selected from the group consisting of diabetes mellitus, insulin deficiency syndrome, maturity onset diabetes of the young (MODY 1-11), and permanent neonatal diabetes mellitus, thereby treating the medical condition associated with the insulin deficiency.

3. The method of claim 1, wherein said primary beta cells are selected from the group consisting of precursor beta cells and mature beta cells.

4. The method of claim 3, wherein said precursor beta cells comprise de-differentiated beta cells.

5. The method of claim 1, wherein said agent is a polynucleotide agent.

6. The method of claim 1, wherein said agent is an antagomir.

7. A method of treating a medical condition associated with an insulin deficiency in a subject in need thereof having said insulin deficiency, the method comprising administering to the subject an isolated population of primary beta cells comprising an exogenous agent for downregulating an activity or expression of miR-7 and wherein said cells secrete insulin, wherein said medical condition associated with an insulin deficiency is selected from the group consisting of diabetes mellitus, insulin deficiency syndrome, maturity onset diabetes of the young (MODY 1-11), and permanent neonatal diabetes mellitus, thereby treating the medical condition associated with the insulin deficiency.

8. The method of claim 2, wherein said agent is a polynucleotide agent.

9. The method of claim 2, wherein said agent is an antagomir.

10. The method of claim 2, wherein said subject is a human subject.

11. The method of claim 7, wherein said primary beta cells are selected from the group consisting of precursor beta cells and mature beta cells.

12. The method of claim 11, wherein said precursor beta cells comprise de-differentiated beta cells.

13. The method of claim 7, wherein said agent is a polynucleotide agent.

14. The method of claim 7, wherein said agent is an antagomir.

15. The method of claim 7, wherein said subject is a human subject.

* * * * *

SEQUENCE LISTING

<160> NUMBER OF SEQ ID NOS: 61

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 1
aacaacctgc ctatgcaacc                                           20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 2
acttggacgg gaactgacac                                           20

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 3
cctgttggtg cacttcctac                                           20

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 4
tgcagtagtt ctccagctgg                                           20

<210> SEQ ID NO 5
<211> LENGTH: 28
<212> TYPE: DNA
<213> ORGANISM: Artificial sequence
<220> FEATURE:
<223> OTHER INFORMATION: Single strand DNA oligonucleotides

<400> SEQUENCE: 5
aaaccaagat cactgacaag aaataggt                                  28

<210> SEQ ID NO 6
<211> LENGTH: 25
<212> TYPE: DNA
<213> ORGANISM: Artificial sequence
<220> FEATURE:
<223> OTHER INFORMATION: Single strand DNA oligonucleotides

<400> SEQUENCE: 6
tttgaaattg tacatcccaa gtgac                                     25

<210> SEQ ID NO 7
<211> LENGTH: 19
<212> TYPE: DNA
<213> ORGANISM: Artificial sequence

```
<220> FEATURE:
<223> OTHER INFORMATION: Single strand DNA oligonucleotides

<400> SEQUENCE: 7
ttcccgaatg gaaccgagc                                                    19

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 8
gtaggcagta cgggtcctct                                                   20

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotides

<400> SEQUENCE: 9
acctcatccc aggcctatct c                                                 21

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 10
tgaggaggaa gccacaggaa                                                   20

<210> SEQ ID NO 11
<211> LENGTH: 21
<212> TYPE: DNA
<213> ORGANISM: Artificial sequence
<220> FEATURE:
<223> OTHER INFORMATION: Single strand DNA oligonucleotides

<400> SEQUENCE: 11
cagatcggca gcacctttga a                                                 21

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 12
gacccactcc ctggaatgga                                                   20

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotides

<400> SEQUENCE: 13
tcccatcccc ttactttgat ga                                                22
```

```
<210> SEQ ID NO 14
<211> LENGTH: 22
<212> TYPE: DNA
<213> ORGANISM: Artificial sequence
<220> FEATURE:
<223> OTHER INFORMATION: Single strand DNA oligonucleotides

<400> SEQUENCE: 14
gtagcagtat tcgtgtagct gg                                                  22

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotides

<400> SEQUENCE: 15
tggcaaagtg gagattgttg cc                                                  22

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotides

<400> SEQUENCE: 16
aagatggtga tgggcttccc g                                                   21

<210> SEQ ID NO 17
<211> LENGTH: 24
<212> TYPE: DNA
<213> ORGANISM: Artificial sequence
<220> FEATURE:
<223> OTHER INFORMATION: Single strand DNA oligonucleotides

<400> SEQUENCE: 17
ctggttaagc agtacagccc caaa                                                24

<210> SEQ ID NO 18
<211> LENGTH: 24
<212> TYPE: DNA
<213> ORGANISM: Artificial sequence
<220> FEATURE:
<223> OTHER INFORMATION: Single strand DNA oligonucleotides

<400> SEQUENCE: 18
tggcctgtat ccaacacttc gaga                                                24

<210> SEQ ID NO 19
<211> LENGTH: 23
<212> TYPE: RNA
<213> ORGANISM: Artificial sequence
<220> FEATURE:
<223> OTHER INFORMATION: Anti-miR-7 antagomir (2'OH)-chl
<220> FEATURE:
<221> NAME/KEY: misc_feature
<223> OTHER INFORMATION: 2-O'-methylated oligonucleotide
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (1)..(2)
<223> OTHER INFORMATION: Phosphorothioate backbone
<220> FEATURE:
```

```
<221> NAME/KEY: misc_feature
<222> LOCATION: (20)..(23)
<223> OTHER INFORMATION: phosphorothioate backbone
<220> FEATURE:
<221> NAME/KEY: misc_feature
<222> LOCATION: (23)..(23)
<223> OTHER INFORMATION: (2'OH)-Chol conjugated oligonucleotide

<400> SEQUENCE: 19
acaacaaaau cacuagucuu cca                                              23

<210> SEQ ID NO 20
<211> LENGTH: 23
<212> TYPE: RNA
<213> ORGANISM: Artificial sequence
<220> FEATURE:
<223> OTHER INFORMATION: Anti-miR-122 antagomir (2'OH)-chl
<220> FEATURE:
<221> NAME/KEY: misc_feature
<223> OTHER INFORMATION: 2-O'-methylated oligonucleotide
<220> FEATURE:
<221> NAME/KEY: misc_feature
<222> LOCATION: (1)..(2)
<223> OTHER INFORMATION: Phosphorothioate backbone
<220> FEATURE:
<221> NAME/KEY: misc_feature
<222> LOCATION: (20)..(23)
<223> OTHER INFORMATION: Phosphorothioate backbone
<220> FEATURE:
<221> NAME/KEY: misc_feature
<222> LOCATION: (23)..(23)
<223> OTHER INFORMATION: (2'OH)-Chol conjugated oligonucleotide

<400> SEQUENCE: 20
acaaacacca uugucacacu cca                                              23

<210> SEQ ID NO 21
<211> LENGTH: 110
<212> TYPE: RNA
<213> ORGANISM: Homo sapiens

<400> SEQUENCE: 21
uuggauguug gccuaguucu guguggaaga cuagugauuu uguuguuuuu agauaacuaa      60
aucgacaaca aaucacaguc ugccauaugg cacaggccau gccucuacag                110

<210> SEQ ID NO 22
<211> LENGTH: 110
<212> TYPE: RNA
<213> ORGANISM: Homo sapiens

<400> SEQUENCE: 22
cuggauacag aguggaccgg cuggccccau cuggaagacu agugauuuug uuguugcuuu      60
acugcgcuca acaacaaauc ccagucuacc uaauggugcc agccaucgca                110

<210> SEQ ID NO 23
<211> LENGTH: 110
<212> TYPE: RNA
<213> ORGANISM: Homo sapiens

<400> SEQUENCE: 23
agauuagagu ggcugugguc uagugcugug uggaagacua gugauuuugu uguucgaug       60 uacuacgaca acaagucaca gccggccuca uagcgcagac ucccuucgac                110

<210> SEQ ID NO 24
<211> LENGTH: 23
<212> TYPE: RNA
```

```
<213> ORGANISM: Homo sapiens

<400> SEQUENCE: 24
uggaagacua gugauuugu ugu                                              23

<210> SEQ ID NO 25
<211> LENGTH: 22
<212> TYPE: RNA
<213> ORGANISM: Homo sapiens

<400> SEQUENCE: 25
caacaaauca cagucugcca ua                                              22

<210> SEQ ID NO 26
<211> LENGTH: 22
<212> TYPE: RNA
<213> ORGANISM: Homo sapiens

<400> SEQUENCE: 26
caacaaaucc cagucuaccu aa                                              22

<210> SEQ ID NO 27
<211> LENGTH: 23
<212> TYPE: RNA
<213> ORGANISM: Mus musculus

<400> SEQUENCE: 27
aaaauguaag uauuugucuu ccc                                             23

<210> SEQ ID NO 28
<211> LENGTH: 24
<212> TYPE: RNA
<213> ORGANISM: Mus musculus

<400> SEQUENCE: 28
uggaagacua gugauuugu uugu                                             24

<210> SEQ ID NO 29
<211> LENGTH: 18
<212> TYPE: DNA
<213> ORGANISM: Artificial sequence
<220> FEATURE:
<223> OTHER INFORMATION: Single strand DNA oligonucleotides

<400> SEQUENCE: 29
caggctccag cttcctga                                                   18

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 30
gtggctgcag tttagctggt                                                 20

<210> SEQ ID NO 31
<211> LENGTH: 21
<212> TYPE: DNA
<213> ORGANISM: Artificial sequence
<220> FEATURE:
<223> OTHER INFORMATION: Single strand DNA oligonucleotides

<400> SEQUENCE: 31
```
cgtccttcct ccctctagct c                                              21

<210> SEQ ID NO 32
<211> LENGTH: 19
<212> TYPE: DNA
<213> ORGANISM: Artificial sequence
<220> FEATURE:
<223> OTHER INFORMATION: Single strand DNA oligonucleotides

<400> SEQUENCE: 32
actccctgtc cctgccatg                                                 19

<210> SEQ ID NO 33
<211> LENGTH: 18
<212> TYPE: DNA
<213> ORGANISM: Artificial sequence
<220> FEATURE:
<223> OTHER INFORMATION: Single strand DNA oligonucleotides

<400> SEQUENCE: 33
cagcatttgg caggctct                                                  18

<210> SEQ ID NO 34
<211> LENGTH: 20
<212> TYPE: DNA
<213> ORGANISM: Artificial sequence
<220> FEATURE:
<223> OTHER INFORMATION: Single strand DNA oligonucleotides

<400> SEQUENCE: 34
aggatgttga gctgcgtgag                                                20

<210> SEQ ID NO 35
<211> LENGTH: 24
<212> TYPE: DNA
<213> ORGANISM: Artificial sequence
<220> FEATURE:
<223> OTHER INFORMATION: siPAx6

<400> SEQUENCE: 35
accaugaucg acaagauuug ccat                                           24

<210> SEQ ID NO 36
<211> LENGTH: 22
<212> TYPE: DNA
<213> ORGANISM: Artificial sequence
<220> FEATURE:
<223> OTHER INFORMATION: Anti Human miR-7-1 pre sequence

<400> SEQUENCE: 36
tgtgccatat ggcagactgt ga                                             22

<210> SEQ ID NO 37
<211> LENGTH: 21
<212> TYPE: DNA
<213> ORGANISM: Artificial sequence
<220> FEATURE:
<223> OTHER INFORMATION: Anti Human miR-7-1 pre (loop) sequence

<400> SEQUENCE: 37
tcgatttagt tatctaaaaa c                                              21

<210> SEQ ID NO 38
<211> LENGTH: 21
<212> TYPE: DNA

<213> ORGANISM: Artificial sequence
<220> FEATURE:
<223> OTHER INFORMATION: Anti Human miR-7-2 pre sequnece

<400> SEQUENCE: 38
ggtagactgg gatttgttgt t                                              21

<210> SEQ ID NO 39
<211> LENGTH: 22
<212> TYPE: DNA
<213> ORGANISM: Artificial sequence
<220> FEATURE:
<223> OTHER INFORMATION: Anti Human miR-7-2 pre (loop) sequence

<400> SEQUENCE: 39
gagcgcagta agacaacaac aa                                             22

<210> SEQ ID NO 40
<211> LENGTH: 21
<212> TYPE: DNA
<213> ORGANISM: Artificial sequence
<220> FEATURE:
<223> OTHER INFORMATION: Anti Human miR-7-3 pre sequence

<400> SEQUENCE: 40
gtctgcgcta tgaggccggc t                                              21

<210> SEQ ID NO 41
<211> LENGTH: 21
<212> TYPE: DNA
<213> ORGANISM: Artificial sequence
<220> FEATURE:
<223> OTHER INFORMATION: Anti Human miR-7-3 pre (loop) sequence

<400> SEQUENCE: 41
ttgttgtcgt agtacatcag a                                              21

<210> SEQ ID NO 42
<211> LENGTH: 5616
<212> TYPE: DNA
<213> ORGANISM: Homo sapiens

<400> SEQUENCE: 42
ccccggcgca gcgcggccgc agcagcctcc gcccccgca cggtgtgagc gcccgacgcg      60
gccgaggcgg ccggagtccc gagctagccc cggcggccgc cgccgcccag accggacgac    120
aggccacctc gtcggcgtcc gcccgagtcc ccgcctcgcc gccaacgcca caaccaccgc    180
gcacggcccc ctgactccgt ccagtattga tcgggagagc cggagcgagc tcttcgggga    240
gcagcgatgc gaccctccgg gacggccggg gcagcgctcc tggcgctgct ggctgcgctc    300
tgcccggcga gtcgggctct ggaggaaaag aaagtttgcc aaggcacgag taacaagctc    360
acgcagttgg cacttttga agatcatttt ctcagcctcc agaggatgtt caataactgt    420
gaggtggtcc ttgggaattt ggaaattacc tatgtgcaga ggaattatga tctttccttc    480
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca caaccctgc cctgtgcaac    720 gtggagagca tccagtggcg ggacatagtc agcagtgact ttctcagcaa catgtcgatg    780
gacttccaga accacctggg cagctgccaa aagtgtgatc caagctgtcc caatgggagc    840

```
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080
gtgaacccgg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg gacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag cagggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag tcttgaagg ctgtccaacg   2160
aatgggccta agatcccgtc catcgccact gggatggtgg gggcctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc ccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga cgtactggt gaaaacaccg cagcatgtca agatcacaga ttttgggctg   2820
gccaaactgc tgggtgcgga agagaaagaa taccatgcag aaggaggcaa agtgcctatc   2880
aagtggatgg cattggaatc aatttttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctccctca gccacccata   3060
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
```

```
cttgtcattc aggggGatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttcttttcc   3780
aaggaagcca agccaaatgg catctttaag ggctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt ttgggaagtt gcattccttt gtcttcaaac   4080
tgtgaagcat ttacagaaac gcatccagca agaatattgt cccttCGAGC AGAAATTTAT   4140 cttcaaaga ggtatatttg aaaaaaaaaa aagtatatg tgaggatttt tattgattgg   4200
ggatcttgga gttttcatt gtcgctattg attttactt caatgggctc ttccaacaag   4260
gaagaagctt gctggtagca cttgctaccc tgagttcatc caggcccaac tgtgagcaag   4320
gagcacaagc cacaagtctt ccagaggatg cttgattcca gtggttctgc ttcaaggctt   4380
ccactgcaaa acactaaaga tccaagaagg ccttcatggc cccagcaggc cggatcggta   4440
ctgtatcaag tcatggcagg tacagtagga taagccactc tgtcccttcc tgggcaaaga   4500
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgtttga aactcagtat gctgccctg tcttgctgtc atgaaatcag   4680
caagagagga tgacacatca ataataact cggattccag cccacattgg attcatcagc   4740
atttggacca atagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920
accccccaaa attagtttgt gttacttatg gaagatagtt ttctcctttt acttcacttc   4980
aaaagctttt tactcaaaga gtatatgttc cctccaggtc agctgccccc aaacccctc    5040 cttacgcttt gtcacacaaa aagtgtctct gccttgagtc atctattcaa gcacttacag   5100
ctctggccac aacagggcat tttacaggtg cgaatgacag tagcattatg agtagtgtgg   5160
aattcaggta gtaaatatga aactagggtt tgaaattgat aatgctttca caacatttgc   5220 agatgttta gaaggaaaaa agttccttcc taaataatt tctctacaat tggaagattg   5280
gaagattcag ctagttagga gcccaccttt tttcctaatc tgtgtgtgcc ctgtaacctg   5340
actggttaac agcagtcctt tgtaaacagt gttttaaact ctcctagtca atatccaccc   5400
catccaattt atcaaggaag aaatggttca gaaatatttt tcagcctaca gttatgttca   5460
gtcacacaca catacaaaat gttccttttg cttttaaagt aattttttgac tcccagatca   5520 gtcagagccc ctacagcatt gttaagaaag tatttgattt ttgtctcaat gaaaataaaa   5580
```

```
ctatattcat ttccactcta aaaaaaaaaa aaaaaa                                    5616
```

<210> SEQ ID NO 43
<211> LENGTH: 1210
<212> TYPE: PRT
<213> ORGANISM: Homo sapiens

<400> SEQUENCE: 43

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

-continued

Leu His Ile Leu Pro Val Ala Phe Arg Gly Asp Ser Phe Thr His Thr
    370             375             380

Pro Pro Leu Asp Pro Gln Glu Leu Asp Ile Leu Lys Thr Val Lys Glu
385             390             395             400

Ile Thr Gly Phe Leu Leu Ile Gln Ala Trp Pro Glu Asn Arg Thr Asp
            405             410             415

Leu His Ala Phe Glu Asn Leu Glu Ile Ile Arg Gly Arg Thr Lys Gln
            420             425             430

His Gly Gln Phe Ser Leu Ala Val Val Ser Leu Asn Ile Thr Ser Leu
        435             440             445

Gly Leu Arg Ser Leu Lys Glu Ile Ser Asp Gly Asp Val Ile Ile Ser
    450             455             460

Gly Asn Lys Asn Leu Cys Tyr Ala Asn Thr Ile Asn Trp Lys Lys Leu
465             470             475             480

Phe Gly Thr Ser Gly Gln Lys Thr Lys Ile Ile Ser Asn Arg Gly Glu
            485             490             495

Asn Ser Cys Lys Ala Thr Gly Gln Val Cys His Ala Leu Cys Ser Pro
        500             505             510

Glu Gly Cys Trp Gly Pro Glu Pro Arg Asp Cys Val Ser Cys Arg Asn
    515             520             525

Val Ser Arg Gly Arg Glu Cys Val Asp Lys Cys Asn Leu Leu Glu Gly
530             535             540

Glu Pro Arg Glu Phe Val Glu Asn Ser Glu Cys Ile Gln Cys His Pro
545             550             555             560

Glu Cys Leu Pro Gln Ala Met Asn Ile Thr Cys Thr Gly Arg Gly Pro
            565             570             575

Asp Asn Cys Ile Gln Cys Ala His Tyr Ile Asp Gly Pro His Cys Val
        580             585             590

Lys Thr Cys Pro Ala Gly Val Met Gly Glu Asn Asn Thr Leu Val Trp
    595             600             605

Lys Tyr Ala Asp Ala Gly His Val Cys His Leu Cys His Pro Asn Cys
    610             615             620

Thr Tyr Gly Cys Thr Gly Pro Gly Leu Glu Gly Cys Pro Thr Asn Gly
625             630             635             640

Pro Lys Ile Pro Ser Ile Ala Thr Gly Met Val Gly Ala Leu Leu Leu
            645             650             655

Leu Leu Val Val Ala Leu Gly Ile Gly Leu Phe Met Arg Arg Arg His
        660             665             670

Ile Val Arg Lys Arg Thr Leu Arg Arg Leu Leu Gln Glu Arg Glu Leu
    675             680             685

Val Glu Pro Leu Thr Pro Ser Gly Glu Ala Pro Asn Gln Ala Leu Leu
690             695             700

Arg Ile Leu Lys Glu Thr Glu Phe Lys Lys Ile Lys Val Leu Gly Ser
705             710             715             720

Gly Ala Phe Gly Thr Val Tyr Lys Gly Leu Trp Ile Pro Glu Gly Glu
            725             730             735

Lys Val Lys Ile Pro Val Ala Ile Lys Glu Leu Arg Glu Ala Thr Ser
        740             745             750

Pro Lys Ala Asn Lys Glu Ile Leu Asp Glu Ala Tyr Val Met Ala Ser
    755             760             765

Val Asp Asn Pro His Val Cys Arg Leu Leu Gly Ile Cys Leu Thr Ser
770             775             780

```
Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
        805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
        885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
        965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
                995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
```

Ser Ser  Glu Phe Ile Gly Ala
      1205           1210

<210> SEQ ID NO 44
<211> LENGTH: 4480
<212> TYPE: DNA
<213> ORGANISM: Homo sapiens

<400> SEQUENCE: 44

| | | | | | |
|---|---|---|---|---|---|
| agttgtaact | gtagtaggtc | agtgatacat | ggtgcaaaac | agcctgggat | aatattgcca |   60 |
| gctgccagac | cagactaggg | tggctcaagg | ggttgccata | gtttctaaat | cttttgaagg |  120 |
| aaaaactgat | cgcacagaag | agtggtatgg | aacccagtac | aaacaagaag | ctataccgga |  180 |
| tgaagtcatc | aagaaatggc | aaaatgctga | cctgaatggg | aaatttaaac | ttcctacaaa |  240 |
| gaatgaattt | attcctacga | attttgagat | tttaccgtta | gaaaagaggg | cgacaccata |  300 |
| ccctgctctt | attaaggata | cagctatgag | caaactttgg | ttcaaacaag | atgataagtt |  360 |
| ttttttgccg | aaggcttgtc | tcaactttga | attttcagc | ccatttgctt | atgtggaccc |  420 |
| cttgcactgt | aacatggcct | atttgtacct | tgagctcctc | aaagactcac | tcaacgagta |  480 |
| tgcatatgca | gcagagctag | caggcttgag | ctatgatctc | caaaatacca | tctatgggat |  540 |
| gtatctttca | gtgaaaggtt | acaatgacaa | gcagccaatt | ttactaaaga | agattattga |  600 |
| gaaaatggct | acctttgaga | ttgatgaaaa | aagatttgaa | attatcaaag | aagcatatat |  660 |
| gcgatctctt | aacaatttcc | gggctgaaca | gcctcaccag | catgccatgt | actacctccg |  720 |
| cttgctgatg | actgaagtgg | cctggactaa | agatgagtta | aaagaagctc | tggatgatgt |  780 |
| aacccttcct | cgccttaagg | ccttcatacc | tcagctcctg | tcacggctgc | acattgaagc |  840 |
| ccttctccat | ggaaacataa | caaagcaggc | tgcattagga | attatgcaga | tggttgaaga |  900 |
| cacccctcatt | gaacatgctc | ataccaaacc | tctccttcca | agtcagctgg | ttcggtatag |  960 |
| agaagttcag | ctccctgaca | gaggatggtt | tgtttatcag | cagagaaatg | aagttcacaa | 1020 |
| taactgtggc | atcagagatat | actaccaaac | agacatgcaa | agcacctcag | agaatatgtt | 1080 |
| tctggagctc | ttctgtcaga | ttatctcgga | accttgcttc | aacaccctgc | gcaccaagga | 1140 |
| gcagttgggc | tatatcgtct | tcagcggggcc | acgtcgagct | aatggcatac | agggcttgag | 1200 |
| attcatcatc | cagtcagaaa | agccacctca | ctacctagaa | agcagagtgg | aagctttctt | 1260 |
| aattaccatg | gaaaagtcca | tagaggacat | gacagaagag | gccttccaaa | aacacattca | 1320 |
| ggcattagca | attcgtcgac | tagacaaacc | aaagaagcta | tctgctgagt | gtgctaaata | 1380 |
| ctggggagaa | atcatctccc | agcaatataa | ttttgacaga | gataacactg | aggttgcata | 1440 |
| tttaaagaca | cttaccaagg | aagatatcat | caaattctac | aaggaaatgt | ggcagtaga | 1500 |
| tgctccaagg | agacataagg | tatccgtcca | tgttcttgcc | agggaaatgg | attcttgtcc | 1560 |
| tgttgttgga | gagttcccat | gtcaaaatga | cataaatttg | tcacaagcac | cagccttgcc | 1620 |
| acaacctgaa | gtgattcaga | acatgaccga | attcaagcgt | ggtctgccac | tgtttccct | 1680 |
| tgtgaaacca | catattaact | tcatggctgc | aaaactctga | agattcccca | tgcatgggaa | 1740 |
| agtgcaagtg | gatgcattcc | tgagtcttcc | agagcctaag | aaaatcatct | tggccacttt | 1800 |
| aatagtttct | gattcactat | tagagaaaca | aacaaaaaat | tgtcaaatgt | cattatgtag | 1860 |
| aaatattata | aatccaaagt | aaaattacaaa | atccttataga | tgtagaatat | ttttaaata | 1920 |
| catgcctctt | aaatattta | aaattttct | tttgattact | gagagaaatt | tccccaatat | 1980 |

```
aacaatgctt aaaatgaatg atattcctat agaatcttcc ttccctattc tgtaaaatag   2040
tcacttgtcc gaagaaagtt aaaagttagc tcttttctaa aagcctccta gcttgacata   2100
gaaggcttca caacatttag aaaggtaata acttttaaaa aattgatcct caaatttgct   2160
ttctacttga tggtttcatg taaatcagtg gaaaacatta catttggcag atgataaagc   2220
aatgtcatct tttattagtg aaatgctggt tatataaggc atggttttaa tcttttata    2280 aaatttgaac atgttttta tgccaactcg taaaatgcta gaaaacccta cttatttaca    2340
atgctagaaa tacagactta ccttacatca attttgtcct aaaccgaatt tctcaggatt   2400
actgtggttt ctttcattct gattgaatta tattgaccta cttcttcata gttggtttgc   2460
agtgttccat gagttttact tttcctcatc aacatattgc tttaacacaa catatttatt   2520
taacacgtac aaataggtc aacttcagat cctactgagt gtgtgacatg cttttccaac    2580
atcagctttt tgtaaccacc tgtataactt tttattacag tgaaattgca gtcagtatgt   2640
gaaccaaaat atcttgcccc tttatgaatt taaaaggcag ccaatacaaa gccacctttt   2700
tggaaatata aaaagtaaag ccttgcattc ttatatagca ggtcttcata aaactctaaa   2760
atcccttgtt gctaccagtc taatcttgcc ttaaatgtta agttattttt tgaatatata   2820
aatataaaca tataaacaca gatgatgact ggagtagact tttaaaaaaa tattttttc    2880 atgagatact attttaggtg aaattgttac tgtagattta acagctgttt tgaaatattt   2940
actgttatta aaacttgctt caagagaaat tgtgaatata tttccatata caagcactag   3000
taacagtaag tggccctgtc atccactaac tcaggcaaag taaagaatgg cattttgaa    3060 ggacatttta cctccccata tgatttgatt ggctaggact ttcttctgta aagtcatacc   3120
ttttcacatc ttaagttttt acatttgcca ttttccaaat ctcaatttg ggcaagaacg    3180 atatagtcac aactatgggg ctgctttcaa aagcgggact ccatttctac tgtcagatca   3240
atgtggtgct gtaaccatct ttttatccct accttcaaga acctccttat atgaagcctg   3300
tctttatcca tcagaaggtg tgtgaaatca tcacttcctt ctggttttat gtatttgtag   3360
actatgcagc ttttcattaa actgcaagta tatacaagac agatctgaaa ttaggcctga   3420
gtgttccgat ccaccactgt actagtaaat aaaaatccac ctacctttta tgtggaaaat   3480
tatgtgctat tgagtaactt ttagctcttt tttaaaaaat gggtgaaatt aagtgtctt    3540 ttttatgaga atgacacatg aagagatctg agagcaatct catgtagtct tccatgaacc   3600
tgcaattgtt tggtatgcgt cagcattttc caatttccag gttggatcta gagctgctgt   3660
tgatcactca ggcatactaa tggattcatt tagatgggtc caagctgcag tccatgagca   3720
ataacagact accccagata ctgcagttta cgcagtgctt agtaaatgag atttgtggaa   3780
ctaagttatt agttacctga ggcttcttaa gaaagtcttc ttttttgacc agttgatgtg   3840
aaagagggag catgtgacac agccagtatg gtggagtgct agggttatcc tgtttacaat   3900
aaatcgcctg aatttcacct ctggagtctg catttgtatt attttttccag ttttagtgaa  3960 atagtacagt ggccagtcct cagcctacct ctcaacatcc cagtttgacc agatttcttg   4020
ctttcattgt tcataatgca gaaagcagtg aattatatta acattttaaa agtgtttctg   4080
ggtaacaatg attttgtca aatagaagac tcaatttcac aaccttaaga atagatcact    4140
tttgtaaaac aagaatctca gtatttgatg ttggactcct tgctgtgagt attgtcactg   4200
actccaaacc cagaaagatt tgttcctgcc cttacaggga tgaaaataaa aaggatagaa   4260
aaaatatttc tctcctctac aatgagtcct tacatcttct tgccacatct ccagctgcag   4320
tttaggcaga tatcttgttc aatctctgtc ttcttgatcc ctgtcaaaat aattttttcta  4380
```

-continued

```
ctcatatagt ggccagttgg ctcaggcagg catttcaaga ggaatctgct tgttcctcac    4440 tttttccagca taggacagtg gtccagcccg cacagtcagc                          4480
```

<210> SEQ ID NO 45
<211> LENGTH: 464
<212> TYPE: PRT
<213> ORGANISM: Homo sapiens

<400> SEQUENCE: 45

Met Ser Lys Leu Trp Phe Lys Gln Asp Asp Lys Phe Phe Leu Pro Lys
1               5                   10                  15

Ala Cys Leu Asn Phe Glu Phe Ser Pro Phe Ala Tyr Val Asp Pro
            20                  25                  30

Leu His Cys Asn Met Ala Tyr Leu Tyr Leu Glu Leu Leu Lys Asp Ser
        35                  40                  45

Leu Asn Glu Tyr Ala Tyr Ala Ala Glu Leu Ala Gly Leu Ser Tyr Asp
    50                  55                  60

Leu Gln Asn Thr Ile Tyr Gly Met Tyr Leu Ser Val Lys Gly Tyr Asn
65                  70                  75                  80

Asp Lys Gln Pro Ile Leu Leu Lys Lys Ile Ile Glu Lys Met Ala Thr
                85                  90                  95

Phe Glu Ile Asp Glu Lys Arg Phe Glu Ile Ile Lys Glu Ala Tyr Met
            100                 105                 110

Arg Ser Leu Asn Asn Phe Arg Ala Glu Gln Pro His Gln His Ala Met
        115                 120                 125

Tyr Tyr Leu Arg Leu Leu Met Thr Glu Val Ala Trp Thr Lys Asp Glu
    130                 135                 140

Leu Lys Glu Ala Leu Asp Asp Val Thr Leu Pro Arg Leu Lys Ala Phe
145                 150                 155                 160

Ile Pro Gln Leu Leu Ser Arg Leu His Ile Glu Ala Leu Leu His Gly
                165                 170                 175

Asn Ile Thr Lys Gln Ala Ala Leu Gly Ile Met Gln Met Val Glu Asp
            180                 185                 190

Thr Leu Ile Glu His Ala His Thr Lys Pro Leu Leu Pro Ser Gln Leu
        195                 200                 205

Val Arg Tyr Arg Glu Val Gln Leu Pro Asp Arg Gly Trp Phe Val Tyr
    210                 215                 220

Gln Gln Arg Asn Glu Val His Asn Asn Cys Gly Ile Glu Ile Tyr Tyr
225                 230                 235                 240

Gln Thr Asp Met Gln Ser Thr Ser Glu Asn Met Phe Leu Glu Leu Phe
                245                 250                 255

Cys Gln Ile Ile Ser Glu Pro Cys Phe Asn Thr Leu Arg Thr Lys Glu
            260                 265                 270

Gln Leu Gly Tyr Ile Val Phe Ser Gly Pro Arg Arg Ala Asn Gly Ile
        275                 280                 285

Gln Gly Leu Arg Phe Ile Ile Gln Ser Glu Lys Pro Pro His Tyr Leu
    290                 295                 300

Glu Ser Arg Val Glu Ala Phe Leu Ile Thr Met Glu Lys Ser Ile Glu
305                 310                 315                 320

Asp Met Thr Glu Glu Ala Phe Gln Lys His Ile Gln Ala Leu Ala Ile
                325                 330                 335

Arg Arg Leu Asp Lys Pro Lys Leu Leu Ser Ala Glu Cys Ala Lys Tyr
            340                 345                 350

```
Trp Gly Glu Ile Ile Ser Gln Gln Tyr Asn Phe Asp Arg Asp Asn Thr
            355                 360                 365
Glu Val Ala Tyr Leu Lys Thr Leu Thr Lys Glu Asp Ile Ile Lys Phe
    370                 375                 380
Tyr Lys Glu Met Leu Ala Val Asp Ala Pro Arg Arg His Lys Val Ser
385                 390                 395                 400
Val His Val Leu Ala Arg Glu Met Asp Ser Cys Pro Val Val Gly Glu
                405                 410                 415
Phe Pro Cys Gln Asn Asp Ile Asn Leu Ser Gln Ala Pro Ala Leu Pro
            420                 425                 430
Gln Pro Glu Val Ile Gln Asn Met Thr Glu Phe Lys Arg Gly Leu Pro
        435                 440                 445
Leu Phe Pro Leu Val Lys Pro His Ile Asn Phe Met Ala Ala Lys Leu
    450                 455                 460

<210> SEQ ID NO 46
<211> LENGTH: 7014
<212> TYPE: DNA
<213> ORGANISM: Homo sapiens

<400> SEQUENCE: 46
cggggaccgc gacgagcccg ggtcgccgtt ggcagcagca gcagcaacac cagcagcagc        60
agcagcccg  gcggcggcgc ggaccccgag cgcccgggcg caccccggct tcccggagcg       120
cgacgcggcg gcagcagccc cggtgcggcc gcgcgcgcct taggctcggc cccgcggctc       180
ggggaccccg actcccggcc cagcgagcgc gtccccccgg ccgcccgag  agcccgagga       240
ggcagcggcc gcaggcagcc ggggagggg  gcggccaccg cccgcgccgg gcatcctcag       300
gagccccaga gcgcggaggg cgcggcgccg ccgagcggtg ctggccccg  cgggcctccc       360
cggaccttcc ccaccgcctg gcccgaggg  acgcgtgatc gggcgggcgg ccgggcgcaa       420
gggtgggagg gagccgcccc cgcccgcgcc ccctccgccc ctcgcccaa  ccctgggcg        480
ccgggcccgg gccgcgcggc ctgaagcgcc cgcgatggcg agcccgccgc ggcacgggcc       540
gcccgggccg cgagcggag  acggcccaa  cctcaacaac aacaacaaca caacaacca        600
cagcgtgcgc aagtgcggct acctgcgcaa gcagaagcat ggccacaagc gcttcttcgt       660
gctgcgcgga cccggcgcgg gcggcgacga ggcgacggcg ggcggggggt cggcgccgca       720
accgccgcgg ctcgagtact acgagagcga gaaaaagtgg cggagcaagg caggcgcgcc       780
gaaacgggtg atcgctctcg actgctgcct gaacatcaac aagcgcgccg acgccaagca       840
caagtacctg atcgccctct acaccaagga cgagtacttc gccgtggccg ccgagaacga       900
gcaggagcag gagggctggt accgcgcgct caccgacctg gtcagcgagg ccgcgcggc        960
cgccggagac gcgccccccg ccgcgcgcc  cgccgcgtcc tgcagcgcct ccctgcccgg      1020
cgccctgggc ggctctgccg gcgccgccgg ggccgaggac agctacgggc tggtggctcc      1080
cgccacggcc gcctaccgtg aggtgtggca ggtgaacctg aagcccaagg gtctgggcca      1140
gagcaagaac ctgacggggg tgtaccgtct gtgcctgtct gcgcgcacca tcggcttcgt      1200
gaagctcaac tgcgagcagc cgtcggtgac gctgcagctc atgaacatcc gccgctgcgg      1260
ccactcggac agcttcttct tcatcgaggt gggccgctcg gccgtcacag gccccggcga      1320
gctgtggatg caggcggacg actcggtggt ggcgcagaac atccacgaga ccatcctgga      1380
ggccatgaag gcgctcaagg agctcttcga gttccggccg gcagtaaga  gccaatcgtc      1440
ggggtcgtcg gccacgcacc ccatcagcgt ccccggcgcg cgccgccacc accacctggt      1500
```

```
caacctgccc cccagccaga cgggcctggt gcgccgctcg cgcaccgaca gcctggccgc    1560 cacccgccg gcggccaagt gcagctcgtg ccgggtgcgc accgccagcg agggcgacgg     1620
cggcgcggcg gcgggagcgg cggccgcggg cgccaggccg gtgtcggtgg ctgggagccc    1680
cctgagcccc gggccggtgc gcgcgcccct gagccgctcg cacaccctga gcggcggctg    1740
cggcggccgc gggagcaagg tggcgctgct gccggcaggg ggcgcgctgc aacacagccg    1800
ctccatgtcc atgcccgtgg cgcactcgcc gccgccgcc accagccccg gctccctgtc     1860
gtccagcagc ggccacggct cgggctccta cccgccgccg cccggcccgc accgcctct     1920 gccgcatccg ctgcaccacg gccccggcca gcggccctcc agcggcagcg cctccgcctc    1980
gggctccccc agcgaccccg gcttcatgtc cctggacgag tacggctcca gcccaggcga    2040
cctgcgcgcc ttctgcagcc accgaagcaa cacgcccgag tccatcgcgg agacgccccc    2100 ggccccgagac ggcggcggcg gcggtgagtt ctacgggtac atgaccatgg acaggcccct   2160
gagccactgt ggccgctcct accgccgggt ctcggggggac gcggcccagg acctggaccg    2220
agggctgcgc aagaggacct actccctgac cacgccagcc cggcagcggc cggtgcccca    2280
gccctcctct gcctcgctgg atgaatacac cctgatgcgg gccaccttct cgggcagcgc    2340
gggccgcctc tgcccgtcct gccccgcgtc ctctcccaag gtggcctacc accctaccc    2400 agaggactac ggagacatcg agatcggctc ccacaggagc tccagcagca acctgggggc    2460
agacgacggc tacatgccca tgacgcccgg cgcggccctc gcgggcagtg ggagcggcag    2520
ctgcaggagc gacgactaca tgcccatgag ccccgccagc gtgtccgccc ccaagcagat    2580
cttgcagccc agggccgccg ccgccgccgc cgccgccgtg ccttctgcgg ggcctgcggg    2640
gccagcaccc acctctgcgg cgggcaggac attcccggcg agcggggggcg gctacaaggc    2700 cagctcgccc gccgagagct cccccgagga cagtgggtac atgcgcatgt ggtgcggttc    2760
caagctgtcc atggagcatg cagatggcaa gctgctgccc aacggggact acctcaacgt    2820
gtcccccagc gacgcggtca ccacgggcac cccgcccgac ttcttctccg cagccctgca    2880
ccccggcggg gagccgctca ggggcgttcc cggctgctgc tacagctcct tgccccgctc    2940
ctacaaggcc ccctacacct gtggcgggga cagcgaccag tacgtgctca tgagctcccc    3000
cgtggggcgc atcctggagg aggagcgtct ggagcctcag gccacgccag ggcccagcca    3060
ggcggccagc gccttcgggg ccggcccac gcagcccccct caccctgtag tgccttcgcc    3120
cgtgcggcct agcggcggcc gccccggaggg cttcttgggc cagcgcggcc gggcggtgag    3180
gcccacgcgc ctgtccctgg aggggctgcc cagcctgccc agcatgcacg agtacccact    3240
gccaccggag cccaagagcc ccggcgagta catcaacatc gactttggcg agcccggggc    3300
ccgcctgtcg ccgccgcgc ctccctgct ggcgtcggcg gctcgtcct cctcgctctt      3360 gtccgccagc agcccggcct cgtcgctggg ctcaggcacc ccgggcacca gcagcgacag    3420
ccggcagcgg tctccgctct ccgactacat gaacctcgac ttcagctccc ccaagtctcc    3480
taagccgggc gccccgagcg gccaccccgt gggctccttg gacggcctcc tgtccccga    3540 ggcctcctcc ccgtatccgc cgttgccccc gcgtccgtcc gcgtcccgt cgtcgtctct    3600 gcagccgccg ccaccgccgc cggccccggg ggagctgtac cgcctgcccc ccgcctcggc    3660
cgttgccacc gcccaggcc cggcgccgc ctcatcgttg tcctcggaca ccggggacaa    3720
tggtgactac accgagatgg cttttggtgt ggccgccacc ccgccgcaac ctatcgcggc    3780 cccccccgaag ccagaagctg cccgcgtggc cagcccgacg tcgggcgtga agaggctgag    3840
cctcatggag caggtgtcgg gagtcgaggc cttcctgcag gccagccagc cccggaccc    3900
```

```
ccaccgcggc gccaaggtca tccgcgcaga cccgcagggg ggccgccgcc gccacagttc    3960
cgagaccttc tcctccacca cgacggtcac ccccgtgtcc ccgtccttcg cccacaaccc    4020
caagcgccac aactcggcct ccgtggaaaa tgtctctctc aggaaaagca gcgagggcgg    4080
cgtgggtgtc ggccctggag ggggcgacga gccgcccacc tccccacgac agttgcagcc    4140 ggcgcccccct ttggcaccgc agggccggcc gtggaccccg ggtcagcccg ggggcttggt    4200
cggttgtcct gggagcggtg gatcgcccat gcgcagagag acctctgccg gcttccagaa    4260
tggtctcaac tacatcgcca tcgacgtgag ggaggagccc gggctgccac cccagccgca    4320
gccgccgccg ccgccgcttc ctcagccggg agacaagagc tcctggggcc ggacccgaag    4380
cctcgggggt ctcatcagcg ctgtgggcgt cggcagcacc ggcggcgggt gcggggggcc    4440
gggtcccggt gccctgcccc ctgccaacac ctacgccagc attgacttct tgtcccacca    4500
cttgaaggag gccaccatcg tgaaagagtg aagatctgtc tggctttatc accaggatgt    4560
cacatgtcag agagtatcat taaaagaaga cgctcagcac tgtttcagcc cgaagctgct    4620
tgcagttttc ttttggatct gagcaatgac tgtgtttgga acatctgtg gactctgtta    4680 gatgaggcac caacaaggca aggtcacctg cctctttccc ttgttcccgg atggggcatt    4740
catcattgtg ctgtttgcgt tttgttttgt tttgttttaa caaaattagc tgaagaagtt    4800
attctcaaga aaattggatg ttttcattgg ccttcttaaa ttgtggccag tgtcttttaa    4860
tttcttcttc ttttcctttt ggcaaagcag atataacccct cagcatgcta ggagagtgca    4920
cccgtaccta tggaagtggt aaaatctggt atttactggc ttacactcaa aacgaccaca    4980
gtcctacctc agttcaaggt aaagccggat ttccgtggcg ggggtcccac aggacctcct    5040
gtagtagccc ctgcgctgtg tgtctggagc gcggtcctcg gccttattga aatggtccaa    5100
gtagacagct gcttgttgga ttccagtgca ggtacctgcg atgtttacgt ccacaccgag    5160
cccagtgtgg gactgacatt tctcaatgga agtgaaattt gggattggac tttgaagacg    5220
gattactaaa taataattat tatatgtaac tgaagcaacc tacttttgaa aatcaactgt    5280
attgggtagt gggaggtggg agggaagggc tttgggaagg ggatgaatat ctcttttttac    5340 cttaacaga cttgtttaat cttctcgatg tagatgttta tgtaggtact tcacattgca    5400
aacgcctttt attctattta caagctcaga tgtctctgct ctcctgaatc ttgggcatgc    5460
ctttctgtaa ccaaaaatcc ctgtaggcgt gctagcaatt ccagggtggt ccgggttttgg    5520 cagatttgat ttttaaaaaa cgtattatct ttaataaaat gttattatgt caaccagtga    5580
ggctgccctg aacaaaaaaa acaaaaagaa aaaaaaaaa ggaaagaaag aaactgataa    5640
aaagaggcat tccagcccct atgttattga tggaaaaaga aaagaagaa aagcaatctc    5700 gcagtacatg ttacttgtcg aaaaaattcc ggacaagact acccttgttt tatgttttca    5760
gtattctgaa ataccagtg tgtggcagtt ctcgcagatg ttacctaaaa ctgctgaact    5820
tgaccggcag aatgttctgc cgttttctgc tccctcgaca cttgattgga gggctgtcga    5880
cctctcctcc cgtgggggct tccccagtgc ctatcttctc tgatagtcat ggagaggtta    5940
cactaattca ttggagatgt aagttgttgg ttttgttttg ttttgttttt agaaaaaatat    6000 atataaatat ataatagata tctatcgcta tagaataatg cattaataaa atgaggcttt    6060
tttagaggaa gaccaaaaaa ttcaatgtct taaaaatata tttaatggca atgcaaaagt    6120
cttcctgctt ccgtgctgaa ctttagaaca gaggattgta ttgcaagaca aagttgaatg    6180
taaagtgatc tccctgaaca ttttaaggt tttacttttc tgaaattata catcacagca    6240
```

-continued

```
gtgcataggc catataatgt tagctggaag gtcaatttca gtgtatgata tactttatta    6300
agatgtataa aaatcctgaa gttttatttt agttttggga ataggcatca atgggtggta    6360
tttgctttgt aactcccccc aggtacgata gggactgaat atggaccctg ctgaaagcag    6420
tgtattgacg catatttaac tcgccctcta ccgtagagt agtcatgaca ctatacagat     6480
ggttcgtgtt catactgcag cttaaaacaa gcaaaataca cagatgataa tatgctaaat    6540
tttcctctat cctgtacatt tcacaaaaag gcatatgcaa tatttacatt tttaatttag    6600
tttacagaat ggaaccaaaa tgtataaatg ttatgtttgc taaaacttca caatgtatat    6660
tgggtctttg tacattttgc ctgacttacc ttaaatttaa aatatttttt gctatataaa    6720
ctttaacagt tattaaacag tgttttcttt ttgggtacgt attgtttctg gatatcaaga    6780
tgttaaatat atttcttgct attgtgatat gacaagagac ttaacttatc ttgctctgtc    6840
ttccactgta cacgctgtat ataggggtca atgtgatgct gctggagacg agaataaact    6900
ggactagaat agtgcattgt atttagtctg tattgatcat ggatgccctc cttaatagcc    6960
atatgcaata aaataaagta cattatttat gaaatgaaaa aaaaaaaaa aaaa           7014
```

<210> SEQ ID NO 47
<211> LENGTH: 1338
<212> TYPE: PRT
<213> ORGANISM: Homo sapiens

<400> SEQUENCE: 47

```
Met Ala Ser Pro Pro Arg His Gly Pro Pro Gly Pro Ala Ser Gly Asp
1               5                   10                  15

Gly Pro Asn Leu Asn Asn Asn Asn Asn Asn His Ser Val Arg
            20                  25                  30

Lys Cys Gly Tyr Leu Arg Lys Gln Lys His Gly His Lys Arg Phe Phe
        35                  40                  45

Val Leu Arg Gly Pro Gly Ala Gly Gly Asp Glu Ala Thr Ala Gly Gly
    50                  55                  60

Gly Ser Ala Pro Gln Pro Pro Arg Leu Glu Tyr Tyr Glu Ser Glu Lys
65                  70                  75                  80

Lys Trp Arg Ser Lys Ala Gly Ala Pro Lys Arg Val Ile Ala Leu Asp
                85                  90                  95

Cys Cys Leu Asn Ile Asn Lys Arg Ala Asp Ala Lys His Lys Tyr Leu
            100                 105                 110

Ile Ala Leu Tyr Thr Lys Asp Glu Tyr Phe Ala Val Ala Ala Glu Asn
        115                 120                 125

Glu Gln Glu Gln Glu Gly Trp Tyr Arg Ala Leu Thr Asp Leu Val Ser
    130                 135                 140

Glu Gly Arg Ala Ala Ala Gly Asp Ala Pro Ala Ala Ala Pro Ala
145                 150                 155                 160

Ala Ser Cys Ser Ala Ser Leu Pro Gly Ala Leu Gly Gly Ser Ala Gly
                165                 170                 175

Ala Ala Gly Ala Glu Asp Ser Tyr Gly Leu Val Ala Pro Ala Thr Ala
            180                 185                 190

Ala Tyr Arg Glu Val Trp Gln Val Asn Leu Lys Pro Lys Gly Leu Gly
        195                 200                 205

Gln Ser Lys Asn Leu Thr Gly Val Tyr Arg Leu Cys Leu Ser Ala Arg
    210                 215                 220

Thr Ile Gly Phe Val Lys Leu Asn Cys Glu Gln Pro Ser Val Thr Leu
225                 230                 235                 240
```

-continued

```
Gln Leu Met Asn Ile Arg Arg Cys Gly His Ser Asp Ser Phe Phe Phe
            245                 250                 255
Ile Glu Val Gly Arg Ser Ala Val Thr Gly Pro Gly Glu Leu Trp Met
        260                 265                 270
Gln Ala Asp Asp Ser Val Val Ala Gln Asn Ile His Glu Thr Ile Leu
    275                 280                 285
Glu Ala Met Lys Ala Leu Lys Glu Leu Phe Glu Phe Arg Pro Arg Ser
290                 295                 300
Lys Ser Gln Ser Ser Gly Ser Ser Ala Thr His Pro Ile Ser Val Pro
305                 310                 315                 320
Gly Ala Arg Arg His His His Leu Val Asn Leu Pro Pro Ser Gln Thr
            325                 330                 335
Gly Leu Val Arg Arg Ser Arg Thr Asp Ser Leu Ala Ala Thr Pro Pro
        340                 345                 350
Ala Ala Lys Cys Ser Ser Cys Arg Val Arg Thr Ala Ser Glu Gly Asp
    355                 360                 365
Gly Gly Ala Ala Ala Gly Ala Ala Ala Gly Ala Arg Pro Val Ser
370                 375                 380
Val Ala Gly Ser Pro Leu Ser Pro Gly Pro Val Arg Ala Pro Leu Ser
385                 390                 395                 400
Arg Ser His Thr Leu Ser Gly Gly Cys Gly Gly Arg Gly Ser Lys Val
            405                 410                 415
Ala Leu Leu Pro Ala Gly Gly Ala Leu Gln His Ser Arg Ser Met Ser
        420                 425                 430
Met Pro Val Ala His Ser Pro Ala Ala Thr Ser Pro Gly Ser Leu
    435                 440                 445
Ser Ser Ser Ser Gly His Gly Ser Gly Ser Tyr Pro Pro Pro Gly
450                 455                 460
Pro His Pro Pro Leu Pro His Pro Leu His His Gly Pro Gly Gln Arg
465                 470                 475                 480
Pro Ser Ser Gly Ser Ala Ser Ala Ser Gly Ser Pro Ser Asp Pro Gly
            485                 490                 495
Phe Met Ser Leu Asp Glu Tyr Gly Ser Ser Pro Gly Asp Leu Arg Ala
        500                 505                 510
Phe Cys Ser His Arg Ser Asn Thr Pro Glu Ser Ile Ala Glu Thr Pro
    515                 520                 525
Pro Ala Arg Asp Gly Gly Gly Gly Glu Phe Tyr Gly Tyr Met Thr
530                 535                 540
Met Asp Arg Pro Leu Ser His Cys Gly Arg Ser Tyr Arg Arg Val Ser
545                 550                 555                 560
Gly Asp Ala Ala Gln Asp Leu Asp Arg Gly Leu Arg Lys Arg Thr Tyr
            565                 570                 575
Ser Leu Thr Thr Pro Ala Arg Gln Arg Pro Val Pro Gln Pro Ser Ser
        580                 585                 590
Ala Ser Leu Asp Glu Tyr Thr Leu Met Arg Ala Thr Phe Ser Gly Ser
    595                 600                 605
Ala Gly Arg Leu Cys Pro Ser Cys Pro Ala Ser Ser Pro Lys Val Ala
610                 615                 620
Tyr His Pro Tyr Pro Glu Asp Tyr Gly Asp Ile Glu Ile Gly Ser His
625                 630                 635                 640
Arg Ser Ser Ser Asn Leu Gly Ala Asp Asp Gly Tyr Met Pro Met
            645                 650                 655
Thr Pro Gly Ala Ala Leu Ala Gly Ser Gly Ser Gly Ser Cys Arg Ser
```

```
                    660                 665                 670
Asp Asp Tyr Met Pro Met Ser Pro Ala Ser Val Ser Ala Pro Lys Gln
            675                 680                 685

Ile Leu Gln Pro Arg Ala Ala Ala Ala Ala Ala Ala Val Pro Ser
            690                 695                 700

Ala Gly Pro Ala Gly Pro Ala Pro Thr Ser Ala Ala Gly Arg Thr Phe
705                 710                 715                 720

Pro Ala Ser Gly Gly Gly Tyr Lys Ala Ser Ser Pro Ala Glu Ser Ser
                725                 730                 735

Pro Glu Asp Ser Gly Tyr Met Arg Met Trp Cys Gly Ser Lys Leu Ser
            740                 745                 750

Met Glu His Ala Asp Gly Lys Leu Leu Pro Asn Gly Asp Tyr Leu Asn
            755                 760                 765

Val Ser Pro Ser Asp Ala Val Thr Thr Gly Thr Pro Pro Asp Phe Phe
770                 775                 780

Ser Ala Ala Leu His Pro Gly Gly Glu Pro Leu Arg Gly Val Pro Gly
785                 790                 795                 800

Cys Cys Tyr Ser Ser Leu Pro Arg Ser Tyr Lys Ala Pro Tyr Thr Cys
                805                 810                 815

Gly Gly Asp Ser Asp Gln Tyr Val Leu Met Ser Ser Pro Val Gly Arg
                820                 825                 830

Ile Leu Glu Glu Glu Arg Leu Glu Pro Gln Ala Thr Pro Gly Pro Ser
            835                 840                 845

Gln Ala Ala Ser Ala Phe Gly Ala Gly Pro Thr Gln Pro Pro His Pro
            850                 855                 860

Val Val Pro Ser Pro Val Arg Pro Ser Gly Gly Arg Pro Glu Gly Phe
865                 870                 875                 880

Leu Gly Gln Arg Gly Arg Ala Val Arg Pro Thr Arg Leu Ser Leu Glu
                885                 890                 895

Gly Leu Pro Ser Leu Pro Ser Met His Glu Tyr Pro Leu Pro Pro Glu
                900                 905                 910

Pro Lys Ser Pro Gly Glu Tyr Ile Asn Ile Asp Phe Gly Glu Pro Gly
            915                 920                 925

Ala Arg Leu Ser Pro Ala Pro Pro Leu Leu Ala Ser Ala Ser
            930                 935                 940

Ser Ser Ser Leu Leu Ser Ala Ser Ser Pro Ala Ser Ser Leu Gly Ser
945                 950                 955                 960

Gly Thr Pro Gly Thr Ser Ser Asp Ser Arg Gln Arg Ser Pro Leu Ser
                965                 970                 975

Asp Tyr Met Asn Leu Asp Phe Ser Ser Pro Lys Ser Pro Lys Pro Gly
                980                 985                 990

Ala Pro Ser Gly His Pro Val Gly Ser Leu Asp Gly Leu Leu Ser Pro
            995                 1000                1005

Glu Ala Ser Ser Pro Tyr Pro Pro Leu Pro Pro Arg Pro Ser Ala
            1010                1015                1020

Ser Pro Ser Ser Ser Leu Gln Pro Pro Pro Pro Pro Ala Pro
            1025                1030                1035

Gly Glu Leu Tyr Arg Leu Pro Pro Ala Ser Ala Val Ala Thr Ala
            1040                1045                1050

Gln Gly Pro Gly Ala Ala Ser Ser Leu Ser Ser Asp Thr Gly Asp
            1055                1060                1065

Asn Gly Asp Tyr Thr Glu Met Ala Phe Gly Val Ala Ala Thr Pro
            1070                1075                1080
```

```
Pro Gln  Pro Ile Ala Ala Pro  Pro Lys Pro Glu Ala  Ala Arg Val
    1085             1090              1095

Ala Ser  Pro Thr Ser Gly Val  Lys Arg Leu Ser Leu  Met Glu Gln
    1100             1105              1110

Val Ser  Gly Val Glu Ala Phe  Leu Gln Ala Ser Gln  Pro Pro Asp
    1115             1120              1125

Pro His  Arg Gly Ala Lys Val  Ile Arg Ala Asp Pro  Gln Gly Gly
    1130             1135              1140

Arg Arg  Arg His Ser Ser Glu  Thr Phe Ser Ser Thr  Thr Thr Val
    1145             1150              1155

Thr Pro  Val Ser Pro Ser Phe  Ala His Asn Pro Lys  Arg His Asn
    1160             1165              1170

Ser Ala  Ser Val Glu Asn Val  Ser Leu Arg Lys Ser  Ser Glu Gly
    1175             1180              1185

Gly Val  Gly Val Gly Pro Gly  Gly Gly Asp Glu Pro  Pro Thr Ser
    1190             1195              1200

Pro Arg  Gln Leu Gln Pro Ala  Pro Pro Leu Ala Pro  Gln Gly Arg
    1205             1210              1215

Pro Trp  Thr Pro Gly Gln Pro  Gly Gly Leu Val Gly  Cys Pro Gly
    1220             1225              1230

Ser Gly  Gly Ser Pro Met Arg  Arg Glu Thr Ser Ala  Gly Phe Gln
    1235             1240              1245

Asn Gly  Leu Asn Tyr Ile Ala  Ile Asp Val Arg Glu  Glu Pro Gly
    1250             1255              1260

Leu Pro  Pro Gln Pro Gln Pro  Pro Pro Pro Leu Pro  Gln Pro
    1265             1270              1275

Gly Asp  Lys Ser Ser Trp Gly  Arg Thr Arg Ser Leu  Gly Gly Leu
    1280             1285              1290

Ile Ser  Ala Val Gly Val Gly  Ser Thr Gly Gly Gly  Cys Gly Gly
    1295             1300              1305

Pro Gly  Pro Gly Ala Leu Pro  Pro Ala Asn Thr Tyr  Ala Ser Ile
    1310             1315              1320

Asp Phe  Leu Ser His His Leu  Lys Glu Ala Thr Ile  Val Lys Glu
    1325             1330              1335

<210> SEQ ID NO 48
<211> LENGTH: 2949
<212> TYPE: DNA
<213> ORGANISM: Homo sapiens

<400> SEQUENCE: 48
agtttcccga ccagagagaa cgaacgtgtc tgcgggcgcg cggggagcag aggcggtggc    60
gggcggcggc ggcaccggga gccgccgagt gaccctcccc cgcccctctg gcccccacc   120 ctcccacccg cccgtggccc gcgcccatgg ccgcgcgcgc tccacacaac tcaccggagt   180
ccgcgccttg cgccgccgac cagttcgcag ctccgcgcca cggcagccag tctcacctgg   240
cggcaccgcc cgcccaccgc cccggccaca gccctgcgc ccacggcagc actcgaggcg    300
accgcgacag tggtgggga cgctgctgag tggaagagag cgcagcccgg ccaccggacc    360
tacttactcg ccttgctgat tgtctatttt tgcgtttaca acttttctaa gaacttttgt   420
atacaaagga acttttaaa aaagacgctt ccaagttata tttaatccaa agaagaagga   480
tctcggccaa tttggggttt tgggttttgg cttcgtttct tctcttcgtt gactttgggg   540
ttcaggtgcc ccagctgctt cgggctgccg aggaccttct gggcccccac attaatgagg   600
```

-continued

```
cagccacctg gcgagtctga catggctgtc agcgacgcgc tgctcccatc tttctccacg    660
ttcgcgtctg gcccggcggg aagggagaag acactgcgtc aagcaggtgc cccgaataac    720
cgctggcggg aggagctctc ccacatgaag cgacttcccc cagtgcttcc cggccgcccc    780
tatgacctgg cggcggcgac cgtggccaca gacctggaga gcggcggagc cggtgcggct    840
tgcggcggta gcaacctggc gcccctacct cggagagaga ccgaggagtt caacgatctc    900
ctggacctgg actttattct ctccaattcg ctgacccatc ctccggagtc agtggccgcc    960
accgtgtcct cgtcagcgtc agcctcctct tcgtcgtcgc cgtcgagcag cggccctgcc   1020
agcgcgccct ccacctgcag cttcacctat ccgatccggg ccgggaacga cccgggcgtg   1080
gcgccgggcg gcacgggcgg aggcctcctc tatggcaggg agtccgctcc ccctccgacg   1140
gctcccttca acctggcgga catcaacgac gtgagcccct cgggcggctt cgtggccgag   1200
ctcctgcggc cagaattgga cccggtgtac attccgccgc agcagccgca gccgccaggt   1260
ggcgggctga tgggcaagtt cgtgctgaag gcgtcgctga gcgcccctgg cagcgagtac   1320
ggcagcccgt cggtcatcag cgtcagcaaa ggcagccctg acggcagcca cccggtggtg   1380
gtggcgccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620
cacccggggc ccaattaccc atccttcctg cccgatcaga tgcagccgca agtcccgccg   1680
ctccattacc aagagctcat gccacccggt tcctgcatgc cagaggagcc caagccaaag   1740
aggggaagac gatcgtggcc ccggaaaagg accgccaccc acacttgtga ttacgcgggc   1800
tgcggcaaaa cctacacaaa gagttcccat ctcaaggcac acctgcgaac ccacacaggt   1860
gagaaacctt accactgtga ctgggacggc tgtggatgga aattcgcccg ctcagatgaa   1920
ctgaccaggc actaccgtaa acacacgggg caccgcccgt tccagtgcca aaaatgcgac   1980
cgagcatttt ccaggtcgga ccacctcgcc ttacacatga gaggcatttt ttaaatccca   2040
gacagtggat atgacccaca ctgccagaag agaattcagt attttttact tttcacactg   2100
tcttcccgat gagggaagga gcccagccaa aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaaggggggt gactggaagt tgtggatatc agggtataaa   2340
ttatatccgt gagttggggg agggaagacc agaattccct tgaattgtgt attgatgcaa   2400
tataagcata aaagatcacc ttgtattctc tttaccttct aaaagccatt attatgatgt   2460
tagaagaaga ggaagaaatt caggtacaga aaacatgttt aaatagccta atgatggtg    2520 cttggtgagt cttggttcta aaggtaccaa acaaggaagc caaagttttc aaactgctgc   2580
atactttgac aaggaaaatc tatatttgtc ttccgatcaa catttatgac ctaagtcagg   2640
taatatacct ggtttacttc tttagcattt ttatgcagac agtctgttat gcactgtggt   2700
ttcagatgtg caataatttg tacaatggtt tattcccaag tatgccttaa gcagaacaaa   2760
tgtgtttttc tatatagttc cttgccttaa taaatatgta atataaattt aagcaaacgt   2820
ctattttgta tatttgtaaa ctacaaagta aaatgaacat tttgtggagt ttgtattttg   2880
catactcaag gtgagaatta agtttaaat aaacctataa tatttatct gaaaaaaaaa    2940
``` aaaaaaaaa                                                                                                    2949

<210> SEQ ID NO 49
<211> LENGTH: 479
<212> TYPE: PRT
<213> ORGANISM: Homo sapiens

<400> SEQUENCE: 49

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
                20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365
```

```
Met Pro Pro Gly Ser Cys Met Pro Glu Glu Pro Lys Pro Lys Arg Gly
370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
                420                 425                 430

Cys Gly Trp Lys Phe Ala Arg Ser Asp Glu Leu Thr Arg His Tyr Arg
                435                 440                 445

Lys His Thr Gly His Arg Pro Phe Gln Cys Gln Lys Cys Asp Arg Ala
                450                 455                 460

Phe Ser Arg Ser Asp His Leu Ala Leu His Met Lys Arg His Phe
465                 470                 475

<210> SEQ ID NO 50
<211> LENGTH: 8228
<212> TYPE: DNA
<213> ORGANISM: Homo sapiens

<400> SEQUENCE: 50
ccgcgggtct atgggaagtt cggggacttg acagccgctg ccgccgcagg gcattttgg       60 tcgaagagag ctgaagtaat gagaagacat catggaggcc cagtcccaca gctccacgac     120
cactgaaaag aaaaaagttg agaattccat agtgaagtgc tccactcgaa cagatgtgag     180
cgagaaagcc gttgcctcca gcaccacttc taatgaggat gaaagtcctg acagactta     240 tcacagagag agaagaaacg caatcactat gcagccacag aatgtccagg ggctcagcaa     300
agtcagtgag gaaccttcaa catcgagtga cgagagggcc tcattgatca agaaagagat     360
ccatgggtcc ctgccacacg tggcggagcc ctctgtgccg taccgcggga cggtgtttgc     420
catggacccc aggaatggtt acatggagcc ccactaccac cctcctcatc ttttccctgc     480
cttccatcct cctgtaccaa ttgatgccag acatcatgag ggccgttacc attacgatcc     540
atctccgatt cctccattgc atatgacttc cgccttatct agtagcccta cgtatccgga     600
cctgcccttc attaggatct ccccacaccg gaacccact gctgcttccg agtctccctt      660
cagccctcca catccctaca ttaatcccta catggactat atccgctcct gcacagcag     720 cccatcgctc tccatgatct cagcaacccg tgggctgagc cctacagatg cgccccatgc     780
aggagtcagc ccagcagaat actatcatca gatggccctg ctaactggcc agcgcagccc     840
ctatgcagac attattccct cagctgccac cgccggcacg ggggccatcc acatggaata     900
tcttcatgct atggatagca ccagattctc cagccccagg ctgtcagcca ggccgagccg     960
aaaacgtaca ctgtccatat caccactctc cgatcatagc tttgaccttc agaccatgat    1020
aaggacgtct cccaactcct tggtcacgat tctcaataat tcccgtagca gctcttcagc    1080
aagtggctcc tatggtcact tatctgcaag tgcaatcagc cctgccttga gcttcaccta    1140
ctcttccgcg cccgtctctc tccacatgca tcagcagatc taagccgac aacagagctt     1200 aggttcagcc tttggacaca gccctccact catccaccct gccccaactt ttccaacaca    1260
gaggcctatt ccagggatcc ctacggttct gaaccccgtc caggtcagct ccggcccttc    1320
tgagtcctca cagaacaagc ccacgagtga gtctgcagtg agcagcactg gtgacccgat    1380
gcacaacaag aggtccaaga tcaaacccga tgaagacctc cccagcccag gggctcgggg    1440
gcagcaggaa cagcccgaag gaacaaccct tgtcaaggag aaggggaca aagatgaaag     1500
```

-continued

| | | | | | |
|---|---|---|---|---|---|
| caaacaggag | cctgaagtca | tctatgagac | aaactgccac | tgggaaggct | gcgcgaggga | 1560 |
| gttcgacacc | caagagcagc | ttgtgcacca | tataataac | gaccatattc | atggagagaa | 1620 |
| gaaggagttc | gtgtgcaggt | ggctggactg | ctcaagagag | cagaaaccct | tcaaagccca | 1680 |
| gtatatgttg | gtagtgcata | tgagaagaca | cacgggcgag | aagcctcaca | aatgcacttt | 1740 |
| tgaaggttgc | acaaaggcct | actcgagact | agaaaacttg | aaaacacact | tgagatctca | 1800 |
| cactggagag | aaaccatacg | tctgtgagca | cgaaggttgc | aacaaggctt | tctcaaatgc | 1860 |
| ctctgatcgc | gccaaacacc | aaaacagaac | gcattccaat | gagaaaccat | atgtgtgcaa | 1920 |
| aatcccaggc | tgcactaagc | gttacacaga | cccaagctcc | ctccggaaac | atgtgaagac | 1980 |
| agtgcatggc | ccagaggctc | atgtcaccaa | gaagcagcga | ggggacatcc | atcctcggcc | 2040 |
| gccacccccg | agagattccg | gcagccattc | acagtccagg | tcgcctggcc | gaccgactca | 2100 |
| gggagcccctt | ggtgagcagc | aggacctcag | caacactacc | tcaaagcggg | aagaatgcct | 2160 |
| ccaggtgaaa | accgtcaagg | cagagaagcc | aatgacatct | cagccaagcc | ctggtggtca | 2220 |
| gtcttcatgc | agcagccaac | agtcccccat | cagcaactat | tccaacagtg | ggctcgagct | 2280 |
| tcctctgacc | gatggaggta | gtataggaga | cctcagtgcc | atcgatgaaa | ccccaatcat | 2340 |
| ggactcaacc | atttccactg | caaccacagc | ccttgctttg | caagccagga | gaaacccggc | 2400 |
| agggaccaaa | tggatggagc | acgtaaaact | agaaaggcta | aaacaagtga | atggaatgtt | 2460 |
| tccgcgactg | aaccccattc | taccccctaa | agccctgcg | gtctctcctc | tcataggaaa | 2520 |
| tggcacacag | tccaacaaca | cctgcagctt | gggtgggccc | atgacgcttc | tcccgggcag | 2580 |
| aagcgaccctc | tctggggtgg | acgtcactat | gctgaacatg | ctcaacagaa | gggacagcag | 2640 |
| cgccagcacc | atcagctcgg | cctacctgag | cagccgccgc | tcctcaggga | tctcgccctg | 2700 |
| cttctccagc | cgccgctcca | gcgaggcgtc | acaggccgag | ggccggccgc | agaacgtgag | 2760 |
| cgtggccgac | tcctacgacc | ccatctccac | cgacgcctcg | cgccgctcca | gcgaagccag | 2820 |
| ccagagcgac | ggcctgccca | gcctgctcag | cctcacgccc | gccagcagt | accgcctcaa | 2880 |
| ggccaagtac | gcggctgcca | caggagggcc | gccgccgacg | cccctgccca | acatggagag | 2940 |
| gatgagcctg | aagacgcgcc | tggcgctgct | cggggatgcc | ctcgagcctg | gcgtggccct | 3000 |
| gcctccagtt | catgccccga | ggaggtgcag | cgacggggga | gcccacggct | acgggcggcg | 3060 |
| ccacctgcag | ccgcacgatg | cgccgggcca | cggcgtgagg | agggccagcg | acccggtgcg | 3120 |
| gacaggctcc | gagggcctgg | ccctgcctcg | tgtgccgcgc | ttcagcagcc | tcagcagctg | 3180 |
| caacccccg | gcgatggcca | cgtccgcgga | gaagcgcagt | ctcgtgcttc | agaattacac | 3240 |
| gcggcccgag | ggcggccagt | cccgaaactt | ccactcgtcc | cctgtcctc | ccagcatcac | 3300 |
| cgagaacgtc | accctggagt | ccctgaccat | ggacgctgat | gccaacctga | acgatgagga | 3360 |
| tttcctgccg | gacgacgtgg | tgcagtattt | aaattcccag | aaccaagcag | ggtacgagca | 3420 |
| gcacttcccc | agcgccctcc | cggacgacag | caaagtgccc | cacgggcccg | gtgactttga | 3480 |
| cgcgcccggg | ctgccagaca | gccacgctgg | ccagcagttc | catgccctcg | agcagccctg | 3540 |
| ccccgagggc | agcaaaaccg | acctgccat | tcagtggaac | gaagtcagct | ccggaagcgc | 3600 |
| cgacctgtcc | tcctccaagc | tcaagtgtgg | gcgcggcc | gctgtgccgc | agactcgcgc | 3660 |
| cttgggttc | tgcaacggca | tggtcgtcca | cccgcagaac | cccttgagga | gcgggcctgc | 3720 |
| tgggggctat | cagaccctcg | gggagaacag | caaccctac | ggtggccag | agcacttgat | 3780 |
| gctccacaac | agccccggaa | gtggcaccag | tggaaacgcc | ttccatgaac | agccctgtaa | 3840 |
| ggccccgcag | tatgggaact | gtctcaacag | gcagccagtg | gccctggtg | cactcgacgg | 3900 |

```
tgcctgtggt gccgggattc aagcctcaaa gctgaagagc accccatgc aagggagcgg    3960 gggccagctg aatttcggcc tgccggtagc gccaaatgag tcagctggca gcatggtgaa    4020
tggcatgcag aaccaggacc cagtgggaca ggggtacctg gctcaccagc tcctcggcga    4080
cagcatgcag caccegggg caggccgccc cggtcagcag atgcttgggc agattagtgc    4140
tacctcacac atcaacatct accaaggcc agagagctgc ctgccagggg ctcacggcat    4200
gggcagccag ccgtcaagct tggcagttgt caggggctac cagccatgtg ccagctttgg    4260
gggcagcagg cgccaggcta tgccgaggga cagccttgct ctgcagtcag gacagctcag    4320
tgacacaagt cagacctgca gggtgaatgg tatcaagatg gagatgaaag gcagcccca    4380 tccgctgtgc tctaatctgc agaattactc tggtcagttc tatgaccaaa ccgtgggctt    4440
cagtcagcaa gacacgaaag ctggttcatt ctctatttca gacgccagct gcctgctaca    4500
ggggaccagc gccaaaaact ctgagttact ttccccaggt gctaatcagg tgacaagcac    4560
agtggacagc ctcgcagcc atgacctgga aggggtacag attgacttcg atgccatcat    4620
agacgatggg gaccactcca gcctgatgtc gggggccctg agcccaagta tcattcagaa    4680
cctttcccat agctcctccc gcctcaccac gcctcgggcg tccctcccat tcccagcgct    4740
gtccatgagc accaccaaca tggctatcgg ggacatgagt tctttgctga cctccctagc    4800
ggaagaaagc aaattccttg cagttatgca ataggcttta ggaaaaaaag actgcaacca    4860
acggaaatca ataggagttg aagagattaa actgactttg ttttggctgt tttttagtt    4920 ctgtatgtat tttagcaatc tcatctcacc taactgagat gtgtttcaat tatattcctt    4980
ttatggaaaa ggactctgaa aaaccctaaa gtattctagg gagaaactgt cttccatttc    5040
agttttgaat cagtattgtt acactcaaac caccctcttt ttaaaaaaaa aaaaaaaac    5100 tgtaagcccc gcccccttt tagtaaaccg atgtaaattt gtgatgtgca tattcttctt    5160
tcttttagaa gagcagtcaa attaaaggat ttgacatgtt ttgctgttgc tcaaaggaaa    5220
taggagttgg tgtgcttgtg accaaggggt tacacttcca gcttttaaaa ttctccttta    5280
catgtgctca gtgttttgtt ttgtgttttg gtttctgttt tttatttaa ttcccacatt    5340 gggcacaaga atcagaatat ggatagctag tttaagaaac ttttgtgggt gcactgtagc    5400
atagatgaca gaatattgat gttcccccca tctccaattc agttcagggc attccacagt    5460
taaacagaaa tgggaacgtg gggctcttat aaatgaaatg ggcgctcaca gttttggttt    5520
tcagctcttc atgtctgtaa gtgtgctttg ggggaggcta tgtctgtatg gtcgattctc    5580
agttatcaca tttgcctctc ctcccactac cttcatgaac attcagtgct gtttcgcact    5640
gcagttagag agaagggacg gacagttggt gacactcagc cacattgcta ctttatctg    5700 ttctggtaag aagttagata gatggtagat tgaagcaatt gggtagaatt agttggggga    5760
atatttatga gttgctgtgt tgttgatta gttccatctc tttcccattt taactgagaa    5820
ttgattatat atagctctaa gtatataggt atttaaacaa ccccacaagc ggctgtatca    5880
gtaacattta ttaattccac tatagtgagg gaggatttcc attctaaata ccttattttg    5940
agggatttat aaaacttagt tgtaaaagag aaagcccaca tagtgggaat aaattgcttc    6000
agccattttt agtatttgag agcactaggg aagatgttta gtagctgtgt ggatgccttt    6060
tttcacaccc tgtctattga atgctgcatc cattcacgaa gttaaatgtt acatgcagtt    6120
agtccttaat gtggactgga tctgtacttt tgttttggat taaaacattt aaagattttt    6180
gaagtgcagc tactccccac gtgcatttga tacacataaa agtcatactg tgtgtgcaca    6240
```

```
aagagtacat ggattttcca gcatattgct ttaaaaaatt atataaactg ttaaaatatt      6300
aacacctcag gctacctgct gtattctgtc ccattgaccc ctggaattgg atttactgca      6360
agtgattgat aattcaatta tgtggctttt cccctttaat cttgccattt aaattacagt      6420
agaaagacaa atcaagtaa aataaagtgt tagataatag aaagagtgtt aagaccagcc       6480
cacttttctc atgtttatgt tctttcattt ggaccaagaa tctccgcatg gaggttgatt      6540
tgccactggg gactttggct aagactatta ggtttgcttt caactagatg ttcctgagac      6600
aagcagaggg acactgcaat tccccttcca tgcctgctgt tctcccccat gtaagtcttc      6660
tttgaaatta acggatgtgt ctcctttgga acagccccat aacaaaagag aactactgat      6720
ctgagcatag gaaagtagag gctctaccac ttttcagttg aaaaagcaag actttctctg      6780
tgtttctgaa acaaggcata atgttgtcac agaatcagag atccagtctc acttttccac      6840
aaatctccaa atctccagtc ttatcttgtg tgctctaatg gtttggttca atcccttttcc     6900 aactcttgtt ttcaaagcat ggggcctgag tgttctccac tcctcctaag aaaggagctt      6960
gggtggaagg gaccatgctg acctcctcca tcagagggct cttccagtag tattctcgga      7020
tgcaacctcc atttctcagt taccattatt tcctgtatca gctttgtcct tcctggaggg      7080
atgcacagtg atccggccca ccactgttgt tgtcttgtgc ttctgctctt tcctatggtt      7140
tcaggttatt ttctgggttt cccctattct tcttttattt cttttttttt ttatatttgc      7200 tttccttttct actgctttta gatttgcagg agatgcaagt ttcagctcaa tgtttggctt     7260
ctctcaatat ggaaatttca gaaggacaga ggagaggagg gaggaagaag aaagtatact      7320
cctccagaat ttcagtgatc tgttgtggca gtccagtgga aggaaggtct tttgaggtca      7380
cttagaagca tctttttggg acatccttttt gggatctctg taggctaggc atctcatatc     7440
ttgagactca cccccagcct ccaagcctct ctccatttct ctaacctatg cattttagag      7500
cgagaggacc gcctcactag tgtcaccatc ctgccttttc taaaacatgc aggctcacac      7560
attctactcc tgcttaatgt ctgtgttaaa cgttttctaa ccattttgt tttattttc        7620 tgaaaaagtt aacccctccc aactcctcac acattggctc ttcctcttga gccacaaagt      7680
tttgattctt gcgatgtatg tgccttattt tatgttaatc ttgtcaatga gagggaccag      7740
ttggtgttgc ccaatcagca ctccaaggct gtgtgtgcac cagccagaga gcgcacggtg      7800
gtagcagagt cgaggctgtc ttgtatcctg gtttcatgtg ttgttttgaa ctgataggag      7860
gatgttctct tctgacaagt taccttgtg tatcctgcag acatgtaaaa taaaatacaa       7920 gttcatttt ttcaccttt ttagatttt ttaaaaata aatgtgtaa tccttttttt           7980 aaaagaaaca catgtaaata catttaagta ttgtaggcat agcgttcaga tgtgactggc      8040
ccaggcgttc ctcggacaag cctgcattcc ccgtgatcac gcccacctca agcccagggg      8100
ctgcagccca gccacagatg aactctacct ttgctttcag aaccacttag tccttttgta      8160
acaaagaaaa aaaatgtttt cttacaatgt caataaaaaa ttctttgtat ggaaaaaaaa      8220
aaaaaaaa                                                               8228

<210> SEQ ID NO 51
<211> LENGTH: 1580
<212> TYPE: PRT
<213> ORGANISM: Homo sapiens

<400> SEQUENCE: 51

Met Glu Ala Gln Ser His Ser Ser Thr Thr Thr Glu Lys Lys Lys Val
1               5                   10                  15
```

-continued

```
Glu Asn Ser Ile Val Lys Cys Ser Thr Arg Thr Asp Val Ser Glu Lys
             20                  25                  30

Ala Val Ala Ser Ser Thr Thr Ser Asn Glu Asp Glu Ser Pro Gly Gln
         35                  40                  45

Thr Tyr His Arg Glu Arg Arg Asn Ala Ile Thr Met Gln Pro Gln Asn
     50                  55                  60

Val Gln Gly Leu Ser Lys Val Ser Glu Glu Pro Ser Thr Ser Ser Asp
 65                  70                  75                  80

Glu Arg Ala Ser Leu Ile Lys Lys Glu Ile His Gly Ser Leu Pro His
                 85                  90                  95

Val Ala Glu Pro Ser Val Pro Tyr Arg Gly Thr Val Phe Ala Met Asp
            100                 105                 110

Pro Arg Asn Gly Tyr Met Glu Pro His Tyr His Pro His Leu Phe
        115                 120                 125

Pro Ala Phe His Pro Pro Val Pro Ile Asp Ala Arg His His Glu Gly
        130                 135                 140

Arg Tyr His Tyr Asp Pro Ser Pro Ile Pro Pro Leu His Met Thr Ser
145                 150                 155                 160

Ala Leu Ser Ser Ser Pro Thr Tyr Pro Asp Leu Pro Phe Ile Arg Ile
                165                 170                 175

Ser Pro His Arg Asn Pro Thr Ala Ala Ser Glu Ser Pro Phe Ser Pro
            180                 185                 190

Pro His Pro Tyr Ile Asn Pro Tyr Met Asp Tyr Ile Arg Ser Leu His
        195                 200                 205

Ser Ser Pro Ser Leu Ser Met Ile Ser Ala Thr Arg Gly Leu Ser Pro
210                 215                 220

Thr Asp Ala Pro His Ala Gly Val Ser Pro Ala Glu Tyr Tyr His Gln
225                 230                 235                 240

Met Ala Leu Leu Thr Gly Gln Arg Ser Pro Tyr Ala Asp Ile Ile Pro
                245                 250                 255

Ser Ala Ala Thr Ala Gly Thr Gly Ala Ile His Met Glu Tyr Leu His
            260                 265                 270

Ala Met Asp Ser Thr Arg Phe Ser Ser Pro Arg Leu Ser Ala Arg Pro
        275                 280                 285

Ser Arg Lys Arg Thr Leu Ser Ile Ser Pro Leu Ser Asp His Ser Phe
290                 295                 300

Asp Leu Gln Thr Met Ile Arg Thr Ser Pro Asn Ser Leu Val Thr Ile
305                 310                 315                 320

Leu Asn Asn Ser Arg Ser Ser Ser Ala Ser Gly Ser Tyr Gly His
                325                 330                 335

Leu Ser Ala Ser Ala Ile Ser Pro Ala Leu Ser Phe Thr Tyr Ser Ser
            340                 345                 350

Ala Pro Val Ser Leu His Met His Gln Gln Ile Leu Ser Arg Gln Gln
        355                 360                 365

Ser Leu Gly Ser Ala Phe Gly His Ser Pro Pro Leu Ile His Pro Ala
370                 375                 380

Pro Thr Phe Pro Thr Gln Arg Pro Ile Pro Gly Ile Pro Thr Val Leu
385                 390                 395                 400

Asn Pro Val Gln Val Ser Ser Gly Pro Ser Glu Ser Ser Gln Asn Lys
                405                 410                 415

Pro Thr Ser Glu Ser Ala Val Ser Ser Thr Gly Asp Pro Met His Asn
            420                 425                 430

Lys Arg Ser Lys Ile Lys Pro Asp Glu Asp Leu Pro Ser Pro Gly Ala
```

-continued

```
            435                 440                 445
Arg Gly Gln Gln Glu Gln Pro Glu Gly Thr Thr Leu Val Lys Glu Glu
450                 455                 460
Gly Asp Lys Asp Glu Ser Lys Gln Glu Pro Glu Val Ile Tyr Glu Thr
465                 470                 475                 480
Asn Cys His Trp Glu Gly Cys Ala Arg Glu Phe Asp Thr Gln Glu Gln
                    485                 490                 495
Leu Val His His Ile Asn Asn Asp His Ile His Gly Glu Lys Lys Glu
                500                 505                 510
Phe Val Cys Arg Trp Leu Asp Cys Ser Arg Glu Gln Lys Pro Phe Lys
            515                 520                 525
Ala Gln Tyr Met Leu Val Val His Met Arg Arg His Thr Gly Glu Lys
530                 535                 540
Pro His Lys Cys Thr Phe Glu Gly Cys Thr Lys Ala Tyr Ser Arg Leu
545                 550                 555                 560
Glu Asn Leu Lys Thr His Leu Arg Ser His Thr Gly Glu Lys Pro Tyr
                565                 570                 575
Val Cys Glu His Glu Gly Cys Asn Lys Ala Phe Ser Asn Ala Ser Asp
                580                 585                 590
Arg Ala Lys His Gln Asn Arg Thr His Ser Asn Glu Lys Pro Tyr Val
            595                 600                 605
Cys Lys Ile Pro Gly Cys Thr Lys Arg Tyr Thr Asp Pro Ser Ser Leu
610                 615                 620
Arg Lys His Val Lys Thr Val His Gly Pro Glu Ala His Val Thr Lys
625                 630                 635                 640
Lys Gln Arg Gly Asp Ile His Pro Arg Pro Pro Pro Arg Asp Ser
                645                 650                 655
Gly Ser His Ser Gln Ser Arg Ser Pro Gly Arg Pro Thr Gln Gly Ala
                660                 665                 670
Leu Gly Glu Gln Gln Asp Leu Ser Asn Thr Thr Ser Lys Arg Glu Glu
            675                 680                 685
Cys Leu Gln Val Lys Thr Val Lys Ala Glu Lys Pro Met Thr Ser Gln
690                 695                 700
Pro Ser Pro Gly Gly Gln Ser Ser Cys Ser Ser Gln Gln Ser Pro Ile
705                 710                 715                 720
Ser Asn Tyr Ser Asn Ser Gly Leu Glu Leu Pro Leu Thr Asp Gly Gly
                725                 730                 735
Ser Ile Gly Asp Leu Ser Ala Ile Asp Glu Thr Pro Ile Met Asp Ser
                740                 745                 750
Thr Ile Ser Thr Ala Thr Thr Ala Leu Ala Leu Gln Ala Arg Arg Asn
            755                 760                 765
Pro Ala Gly Thr Lys Trp Met Glu His Val Lys Leu Glu Arg Leu Lys
770                 775                 780
Gln Val Asn Gly Met Phe Pro Arg Leu Asn Pro Ile Leu Pro Pro Lys
785                 790                 795                 800
Ala Pro Ala Val Ser Pro Leu Ile Gly Asn Gly Thr Gln Ser Asn Asn
                805                 810                 815
Thr Cys Ser Leu Gly Gly Pro Met Thr Leu Leu Pro Gly Arg Ser Asp
                820                 825                 830
Leu Ser Gly Val Asp Val Thr Met Leu Asn Met Leu Asn Arg Arg Asp
            835                 840                 845
Ser Ser Ala Ser Thr Ile Ser Ser Ala Tyr Leu Ser Ser Arg Arg Ser
850                 855                 860
```

```
Ser Gly Ile Ser Pro Cys Phe Ser Ser Arg Arg Ser Glu Ala Ser
865                 870                 875                 880

Gln Ala Glu Gly Arg Pro Gln Asn Val Ser Val Ala Asp Ser Tyr Asp
            885                 890                 895

Pro Ile Ser Thr Asp Ala Ser Arg Arg Ser Ser Glu Ala Ser Gln Ser
            900                 905                 910

Asp Gly Leu Pro Ser Leu Leu Ser Leu Thr Pro Ala Gln Gln Tyr Arg
            915                 920                 925

Leu Lys Ala Lys Tyr Ala Ala Ala Thr Gly Gly Pro Pro Thr Pro
930                 935                 940

Leu Pro Asn Met Glu Arg Met Ser Leu Lys Thr Arg Leu Ala Leu Leu
945                 950                 955                 960

Gly Asp Ala Leu Glu Pro Gly Val Ala Leu Pro Pro Val His Ala Pro
                965                 970                 975

Arg Arg Cys Ser Asp Gly Gly Ala His Gly Tyr Gly Arg Arg His Leu
            980                 985                 990

Gln Pro His Asp Ala Pro Gly His Gly Val Arg Arg Ala Ser Asp Pro
            995                 1000                1005

Val Arg Thr Gly Ser Glu Gly Leu Ala Leu Pro Arg Val Pro Arg
1010                1015                1020

Phe Ser Ser Leu Ser Ser Cys Asn Pro Pro Ala Met Ala Thr Ser
1025                1030                1035

Ala Glu Lys Arg Ser Leu Val Leu Gln Asn Tyr Thr Arg Pro Glu
1040                1045                1050

Gly Gly Gln Ser Arg Asn Phe His Ser Ser Pro Cys Pro Pro Ser
1055                1060                1065

Ile Thr Glu Asn Val Thr Leu Glu Ser Leu Thr Met Asp Ala Asp
1070                1075                1080

Ala Asn Leu Asn Asp Glu Asp Phe Leu Pro Asp Val Val Gln
1085                1090                1095

Tyr Leu Asn Ser Gln Asn Gln Ala Gly Tyr Glu Gln His Phe Pro
1100                1105                1110

Ser Ala Leu Pro Asp Asp Ser Lys Val Pro His Gly Pro Gly Asp
1115                1120                1125

Phe Asp Ala Pro Gly Leu Pro Asp Ser His Ala Gly Gln Gln Phe
1130                1135                1140

His Ala Leu Glu Gln Pro Cys Pro Glu Gly Ser Lys Thr Asp Leu
1145                1150                1155

Pro Ile Gln Trp Asn Glu Val Ser Ser Gly Ser Ala Asp Leu Ser
1160                1165                1170

Ser Ser Lys Leu Lys Cys Gly Pro Arg Pro Ala Val Pro Gln Thr
1175                1180                1185

Arg Ala Phe Gly Phe Cys Asn Gly Met Val Val His Pro Gln Asn
1190                1195                1200

Pro Leu Arg Ser Gly Pro Ala Gly Gly Tyr Gln Thr Leu Gly Glu
1205                1210                1215

Asn Ser Asn Pro Tyr Gly Gly Pro Glu His Leu Met Leu His Asn
1220                1225                1230

Ser Pro Gly Ser Gly Thr Ser Gly Asn Ala Phe His Glu Gln Pro
1235                1240                1245

Cys Lys Ala Pro Gln Tyr Gly Asn Cys Leu Asn Arg Gln Pro Val
1250                1255                1260
```

| Ala Pro | Gly | Ala | Leu | Asp | Gly | Ala | Cys | Gly | Ala | Gly | Ile | Gln | Ala |
| 1265 | | | | 1270 | | | | 1275 | | | | | |

Ser Lys Leu Lys Ser Thr Pro Met Gln Gly Ser Gly Gly Gln Leu
1280                      1285                  1290

Asn Phe Gly Leu Pro Val Ala Pro Asn Glu Ser Ala Gly Ser Met
1295                      1300                  1305

Val Asn Gly Met Gln Asn Gln Asp Pro Val Gly Gln Gly Tyr Leu
1310                      1315                  1320

Ala His Gln Leu Leu Gly Asp Ser Met Gln His Pro Gly Ala Gly
1325                      1330                  1335

Arg Pro Gly Gln Gln Met Leu Gly Gln Ile Ser Ala Thr Ser His
1340                      1345                  1350

Ile Asn Ile Tyr Gln Gly Pro Glu Ser Cys Leu Pro Gly Ala His
1355                      1360                  1365

Gly Met Gly Ser Gln Pro Ser Ser Leu Ala Val Val Arg Gly Tyr
1370                      1375                  1380

Gln Pro Cys Ala Ser Phe Gly Gly Ser Arg Arg Gln Ala Met Pro
1385                      1390                  1395

Arg Asp Ser Leu Ala Leu Gln Ser Gly Gln Leu Ser Asp Thr Ser
1400                      1405                  1410

Gln Thr Cys Arg Val Asn Gly Ile Lys Met Glu Met Lys Gly Gln
1415                      1420                  1425

Pro His Pro Leu Cys Ser Asn Leu Gln Asn Tyr Ser Gly Gln Phe
1430                      1435                  1440

Tyr Asp Gln Thr Val Gly Phe Ser Gln Gln Asp Thr Lys Ala Gly
1445                      1450                  1455

Ser Phe Ser Ile Ser Asp Ala Ser Cys Leu Leu Gln Gly Thr Ser
1460                      1465                  1470

Ala Lys Asn Ser Glu Leu Leu Ser Pro Gly Ala Asn Gln Val Thr
1475                      1480                  1485

Ser Thr Val Asp Ser Leu Asp Ser His Asp Leu Glu Gly Val Gln
1490                      1495                  1500

Ile Asp Phe Asp Ala Ile Ile Asp Asp Gly Asp His Ser Ser Leu
1505                      1510                  1515

Met Ser Gly Ala Leu Ser Pro Ser Ile Ile Gln Asn Leu Ser His
1520                      1525                  1530

Ser Ser Ser Arg Leu Thr Thr Pro Arg Ala Ser Leu Pro Phe Pro
1535                      1540                  1545

Ala Leu Ser Met Ser Thr Thr Asn Met Ala Ile Gly Asp Met Ser
1550                      1555                  1560

Ser Leu Leu Thr Ser Leu Ala Glu Glu Ser Lys Phe Leu Ala Val
1565                      1570                  1575

Met Gln
1580

<210> SEQ ID NO 52
<211> LENGTH: 7014
<212> TYPE: DNA
<213> ORGANISM: Homo sapiens

<400> SEQUENCE: 52
cggggaccgc gacgagcccg ggtcgccgtt ggcagcagca gcagcaacac cagcagcagc   60
agcagccccg gcggcggcgc ggaccccgag cgcccgggcg caccccggct tcccggagcg  120
cgacgcggcg gcagcagccc cggtgcggcc gcgcgcgcct taggctcggc cccgcggctc  180

-continued

| | |
|---|---|
| ggggacccccg actcccggcc cagcgagcgc gtccccggc gccgcccgag agcccgagga | 240 |
| ggcagcggcc gcaggcagcc ggggaggggg gcggccaccg cccgcgccgg gcatcctcag | 300 |
| gagccccaga gcgcgaggg cgcggcgccg ccgagcggtg ctggccccg cgggcctccc | 360 |
| cggaccttcc ccaccgcctg ggcccgaggg acgcgtgatc gggcgggcgg ccgggcgcaa | 420 |
| gggtgggagg gagccgcccc cgccgcgcc ccctccgccc ctcgcccaa cccctgggcg | 480 |
| ccgggcccgg gccgcgcggc ctgaagcgcc cgcgatggcg agcccgccgc ggcacgggcc | 540 |
| gcccgggccg gcgagcggag acggccccaa cctcaacaac aacaacaaca acaacaacca | 600 |
| cagcgtgcgc aagtgcggct acctgcgcaa gcagaagcat ggccacaagc gcttcttcgt | 660 |
| gctgcgcgga cccggcgcgg gcggcgacga ggcgacggcg ggcgggggggt cggcgccgca | 720 |
| accgccgcgg ctcgagtact acgagagcga gaaaaagtgg cggagcaagg caggcgcgcc | 780 |
| gaaacgggtg atcgctctcg actgctgcct gaacatcaac aagcgcgccg acgccaagca | 840 |
| caagtacctg atcgccctct acaccaagga cgagtacttc gccgtggccg ccgagaacga | 900 |
| gcaggagcag gagggctggt accgcgcgct caccgacctg gtcagcgagg gccgcgcggc | 960 |
| cgccggagac gcgcccccg ccgccgcgcc cgccgcgtcc tgcagcgcct ccctgccccgg | 1020 |
| cgccctgggc ggctctgccg gcgccgccgg ggccgaggac agctacgggc tggtggctcc | 1080 |
| cgccacggcc gcctaccgtg aggtgtggca ggtgaacctg aagcccaagg gtctgggcca | 1140 |
| gagcaagaac ctgacggggg tgtaccgtct gtgcctgtct gcgcgcacca tcggcttcgt | 1200 |
| gaagctcaac tgcgagcagc cgtcggtgac gctgcagctc atgaacatcc gccgctgcgg | 1260 |
| ccactcggac agcttcttct tcatcgaggt gggccgctcg gccgtcacag gccccggcga | 1320 |
| gctgtggatg caggcggacg actcggtggt ggcgcagaac atccacgaga ccatcctgga | 1380 |
| ggccatgaag gcgctcaagg agctcttcga gttccggccg cgcagtaaga gccaatcgtc | 1440 |
| ggggtcgtcg gccacgcacc ccatcagcgt ccccggcgcg cgccgccacc accacctggt | 1500 |
| caacctgccc cccagccaga cgggcctggt gcgccgctcg cgcaccgaca gcctggccgc | 1560 |
| caccccgccg gcggccaagt gcagctcgtg ccgggtgcgc accgcagcg agggcgacgg | 1620 |
| cggcgcggcg gcgggagcgg cggccgcggg cgccaggccg gtgtcggtgg ctgggagccc | 1680 |
| cctgagcccc gggccggtgc gcgcgccccct gagccgctcg cacaccctga gcggcggctg | 1740 |
| cggcggccgg gggagcaagg tggcgctgct gccggcaggg ggcgcgctgc aacacagccg | 1800 |
| ctccatgtcc atgcccgtgg cgcactcgcc gcccgccgcc accagccccg gctccctgtc | 1860 |
| gtccagcagc ggccacggct cgggctccta cccgccgccg cccggcccgc acccgcctct | 1920 |
| gccgcatccg ctgcaccacg gccccggcca gcggccctcc agcggcagcg cctccgcctc | 1980 |
| gggctccccc agcgaccccg gcttcatgtc cctggacgag tacggctcca gcccaggcga | 2040 |
| cctgcgcgcc ttctgcagcc accgaagcaa cacgcccgag tccatcgcgg agacgccccc | 2100 |
| ggcccgagac ggcggcggcg gcggtgagtt ctacgggtac atgaccatgg acaggcccct | 2160 |
| gagccactgt ggccgctcct accgccgggt ctcggggggac gcggcccagg acctggaccg | 2220 |
| agggctgcgc aagaggacct actccctgac cacgccagcc cggcagcggc cggtgccccca | 2280 |
| gccctcctct gcctcgctgg atgaatacac cctgatgcgg gccaccttct cgggcagcgc | 2340 |
| gggccgcctc tgcccgtcct gccccgcgtc ctctcccaag gtggcctacc acccctaccc | 2400 |
| agaggactac ggagacatcg agatcggctc ccacaggagc tccagcagca acctgggggc | 2460 |
| agacgacggc tacatgccca tgacgcccgg cgcggccctc gcgggcagtg ggagcggcag | 2520 |

```
ctgcaggagc gacgactaca tgcccatgag ccccgccagc gtgtccgccc ccaagcagat    2580
cttgcagccc agggccgccg ccgccgccgc cgccgccgtg ccttctgcgg ggcctgcggg    2640
gccagcaccc acctctgcgg cgggcaggac attcccggcg agcgggggcg gctacaaggc    2700
cagctcgccc gccgagagct cccccgagga cagtgggtac atgcgcatgt ggtgcggttc    2760
caagctgtcc atggagcatg cagatggcaa gctgctgccc aacggggact acctcaacgt    2820
gtcccccagc gacgcggtca ccacgggcac cccgcccgac ttcttctccg cagccctgca    2880
ccccggcggg gagccgctca ggggcgttcc cggctgctgc tacagctcct tgccccgctc    2940
ctacaaggcc ccctcacacct gtggcgggga cagcgaccag tacgtgctca tgagctcccc    3000
cgtggggcgc atcctggagg aggagcgtct ggagcctcag gccacgccag ggcccagcca    3060
ggcggccagc gccttcgggg ccggcccac gcagccccct cacccctgtag tgccttcgcc    3120 cgtgcggcct agcggcggcc gcccggaggg cttcttgggc cagcgcggcc gggcggtgag    3180
gcccacgcgc ctgtccctgg aggggctgcc cagcctgccc agcatgcacg agtacccact    3240
gccaccggag cccaagagcc ccggcgagta catcaacatc gactttggcg agcccggggc    3300
ccgcctgtcg ccgcccgcgc ctcccctgct ggcgtcggcg gcctcgtcct cctcgctctt    3360
gtccgccagc agcccggcct cgtcgctggg ctcaggcacc ccgggcacca gcagcgacag    3420
ccggcagcgg tctccgctct ccgactacat gaacctcgac ttcagctccc ccaagtctcc    3480
taagccgggc gccccgagcg ccaccccgt gggctccttg gacggcctcc tgtccccgga    3540
ggcctcctcc ccgtatccgc cgttgccccc gcgtccgtcc gcgtcccgt cgtcgtctct    3600 gcagccgccg ccaccgccgc cggccccggg ggagctgtac cgcctgcccc ccgcctcggc    3660
cgttgccacc gccagggcc cgggcgccgc ctcatcgttg tcctcggaca ccggggacaa    3720
tggtgactac accgagatgg cttttggtgt ggccgccacc ccgccgcaac ctatcgcggc    3780
ccccccgaag ccagaagctg cccgcgtggc cagcccgacg tcgggcgtga agaggctgag    3840
cctcatggag caggtgtcgg gagtcgaggc cttcctgcag gccagccagc ccccggaccc    3900
ccaccgcggc gccaaggtca tccgcgcaga cccgcagggg ggccgccgcc gccacagttc    3960
cgagaccttc tcctccacca cgacggtcac ccccgtgtcc ccgtccttcg cccacaaccc    4020
caagcgccac aactcggcct ccgtggaaaa tgtctctctc aggaaaagca gcgagggcgg    4080
cgtgggtgtc ggcccctggag gggcgacga gccgcccacc tccccacgac agttgcagcc    4140
ggcgccccct ttggcaccgc agggccggcc gtggaccccg ggtcagcccg ggggcttggt    4200
cggttgtcct gggagcggtg gatcgcccat gcgcagagag acctctgccg gcttccagaa    4260
tggtctcaac tacatcgcca tcgacgtgag ggaggagccc gggctgccac cccagccgca    4320
gccgccgccg ccgccgcttc ctcagccggg agacaagagc tcctggggcc ggacccgaag    4380 cctcggggt ctcatcagcg ctgtgggcgt cggcagcacc ggcggcgggt gcgggggggcc    4440 gggtcccggt gccctgcccc ctgccaacac ctacgccagc attgacttct tgtcccacca    4500
cttgaaggag gccaccatcg tgaaagagtg aagatctgtc tggctttatc accaggatgt    4560
cacatgtcag agagtatcat taaaagaaga cgctcagcac tgtttcagcc cgaagctgct    4620
tgcagttttc ttttggatct gagcaatgac tgtgttgga acatctgtg gactctgtta    4680 gatgaggcac caacaaggca aggtcacctg cctctttccc ttgttcccgg atggggcatt    4740
catcattgtg ctgtttgcgt tttgtttttgt tttgttttaa caaaattagc tgaagaagtt    4800
attctcaaga aaattggatg ttttcattgg ccttcttaaa ttgtggccag tgtcttttaa    4860
tttcttcttc ttttccttttt ggcaaagcag atataaccct cagcatgcta ggagagtgca    4920
```

```
cccgtaccta tggaagtggt aaaatctggt atttactggc ttacactcaa aacgaccaca    4980
gtcctacctc agttcaaggt aaagccggat ttccgtggcg ggggtcccac aggacctcct    5040
gtagtagccc ctgcgctgtg tgtctggagc gcggtcctcg gccttattga aatggtccaa    5100
gtagacagct gcttgttgga ttccagtgca ggtacctgcg atgtttacgt ccacaccgag    5160
cccagtgtgg gactgacatt tctcaatgga agtgaaattt gggattggac tttgaagacg    5220
gattactaaa taataattat tatatgtaac tgaagcaacc tacttttgaa aatcaactgt    5280
attgggtagt gggaggtggg agggaagggc tttgggaagg ggatgaatat ctcttttac     5340 cttaaacaga cttgtttaat cttctcgatg tagatgttta tgtaggtact tcacattgca    5400
aacgcctttt attctattta caagctcaga tgtctctgct ctcctgaatc ttgggcatgc    5460
ctttctgtaa ccaaaaatcc ctgtaggcgt gctagcaatt ccaggtggt ccgggtttgg     5520 cagatttgat ttttaaaaaa cgtattatct ttaataaaat gttattatgt caaccagtga    5580
ggctgccctg aacaaaaaaa acaaaagaa aaaaaaaaa ggaaagaaag aaactgataa      5640
aaagaggcat tccagcccct atgttattga tggaaaaga aaagaagaa aagcaatctc      5700 gcagtacatg ttacttgtcg aaaaaattcc ggacaagact acccttgttt tatgttttca    5760
gtattctgaa ataccagtg tgtggcagtt ctcgcagatg ttacctaaaa ctgctgaact     5820
tgaccggcag aatgttctgc cgttttctgc tccctcgaca cttgattgga gggctgtcga    5880
cctctcctcc cgtgggggct tccccagtgc ctatcttctc tgatagtcat ggagaggtta    5940
cactaattca ttggagatgt aagttgttgg ttttgttttg ttttgttttt agaaaaatat    6000
atataaatat ataatagata tctatcgcta tagaataatg cattaataaa atgaggcttt    6060
tttagaggaa gaccaaaaaa ttcaatgtct taaaaatata tttaatggca atgcaaaagt    6120
cttcctgctt ccgtgctgaa ctttagaaca gaggattgta ttgcaagaca aagttgaatg    6180
taaagtgatc tccctgaaca tttttaaggt tttactttc tgaaattata catcacagca     6240
gtgcataggc catataatgt tagctggaag gtcaatttca gtgtatgata tactttatta    6300
agatgtataa aaatcctgaa gttttttatt agtttgggga ataggcatca atgggtggta    6360 tttgcttgt aactcccccc aggtacgata gggactgaat atggaccctg ctgaaagcag     6420
tgtattgacg catatttaac tcgccctcta tccgtagagt agtcatgaca ctatacagat    6480
ggttcgtgtt catactgcag cttaaaacaa gcaaataca cagatgataa tatgctaaat     6540
tttcctctat cctgtacatt tcacaaaaag gcatatgcaa tatttacatt tttaatttag    6600
tttacagaat ggaaccaaaa tgtataaatg ttatgtttgc taaaacttca caatgtatat    6660
tgggtctttg tacattttgc ctgacttacc ttaaatttaa aatattttt gctatataaa     6720 ctttaacagt tattaaacag tgttttcttt ttgggtacgt attgtttctg gatatcaaga    6780
tgttaaatat atttcttgct attgtgatat gacaagagac ttaacttatc ttgctctgtc    6840
ttccactgta cacgctgtat ataggggtca atgtgatgct gctggagacg agaataaact    6900
ggactagaat agtgcattgt atttagtctg tattgatcat ggatgccctc cttaatagcc    6960
atatgcaata aaataaagta cattatttat gaaatgaaaa aaaaaaaaa aaaa           7014
```

<210> SEQ ID NO 53
<211> LENGTH: 1338
<212> TYPE: PRT
<213> ORGANISM: Homo sapiens

<400> SEQUENCE: 53

-continued

```
Met Ala Ser Pro Pro Arg His Gly Pro Pro Ala Ser Gly Asp
 1               5                  10                  15

Gly Pro Asn Leu Asn Asn Asn Asn Asn Asn His Ser Val Arg
            20              25                  30

Lys Cys Gly Tyr Leu Arg Lys Gln Lys His Gly His Lys Arg Phe Phe
                35                  40                  45

Val Leu Arg Gly Pro Gly Ala Gly Gly Asp Glu Ala Thr Ala Gly Gly
 50                  55                  60

Gly Ser Ala Pro Gln Pro Pro Arg Leu Glu Tyr Tyr Glu Ser Glu Lys
 65                  70                  75                  80

Lys Trp Arg Ser Lys Ala Gly Ala Pro Lys Arg Val Ile Ala Leu Asp
                85                  90                  95

Cys Cys Leu Asn Ile Asn Lys Arg Ala Asp Ala Lys His Lys Tyr Leu
                100                 105                 110

Ile Ala Leu Tyr Thr Lys Asp Glu Tyr Phe Ala Val Ala Ala Glu Asn
                115                 120                 125

Glu Gln Glu Gln Glu Gly Trp Tyr Arg Ala Leu Thr Asp Leu Val Ser
    130                 135                 140

Glu Gly Arg Ala Ala Ala Gly Asp Ala Pro Ala Ala Ala Pro Ala
145                 150                 155                 160

Ala Ser Cys Ser Ala Ser Leu Pro Gly Ala Leu Gly Gly Ser Ala Gly
                165                 170                 175

Ala Ala Gly Ala Glu Asp Ser Tyr Gly Leu Val Ala Pro Ala Thr Ala
                180                 185                 190

Ala Tyr Arg Glu Val Trp Gln Val Asn Leu Lys Pro Lys Gly Leu Gly
                195                 200                 205

Gln Ser Lys Asn Leu Thr Gly Val Tyr Arg Leu Cys Leu Ser Ala Arg
    210                 215                 220

Thr Ile Gly Phe Val Lys Leu Asn Cys Glu Gln Pro Ser Val Thr Leu
225                 230                 235                 240

Gln Leu Met Asn Ile Arg Arg Cys Gly His Ser Asp Ser Phe Phe Phe
                245                 250                 255

Ile Glu Val Gly Arg Ser Ala Val Thr Gly Pro Gly Glu Leu Trp Met
                260                 265                 270

Gln Ala Asp Asp Ser Val Val Ala Gln Asn Ile His Glu Thr Ile Leu
    275                 280                 285

Glu Ala Met Lys Ala Leu Lys Glu Leu Phe Glu Phe Arg Pro Arg Ser
    290                 295                 300

Lys Ser Gln Ser Ser Gly Ser Ser Ala Thr His Pro Ile Ser Val Pro
305                 310                 315                 320

Gly Ala Arg Arg His His His Leu Val Asn Leu Pro Pro Ser Gln Thr
                325                 330                 335

Gly Leu Val Arg Arg Ser Arg Thr Asp Ser Leu Ala Ala Thr Pro Pro
                340                 345                 350

Ala Ala Lys Cys Ser Ser Cys Arg Val Arg Thr Ala Ser Glu Gly Asp
                355                 360                 365

Gly Gly Ala Ala Ala Gly Ala Ala Ala Gly Ala Arg Pro Val Ser
    370                 375                 380

Val Ala Gly Ser Pro Leu Ser Pro Gly Pro Val Arg Ala Pro Leu Ser
385                 390                 395                 400

Arg Ser His Thr Leu Ser Gly Gly Cys Gly Gly Arg Gly Ser Lys Val
                405                 410                 415

Ala Leu Leu Pro Ala Gly Gly Ala Leu Gln His Ser Arg Ser Met Ser
```

-continued

```
                420             425             430
Met Pro Val Ala His Ser Pro Ala Ala Thr Ser Pro Gly Ser Leu
                435                 440                 445
Ser Ser Ser Ser Gly His Gly Ser Gly Ser Tyr Pro Pro Pro Gly
                450                 455                 460
Pro His Pro Pro Leu Pro His Pro Leu His His Gly Pro Gly Gln Arg
465                 470                 475                 480
Pro Ser Ser Gly Ser Ala Ser Ala Ser Gly Ser Pro Ser Asp Pro Gly
                485                 490                 495
Phe Met Ser Leu Asp Glu Tyr Gly Ser Ser Pro Gly Asp Leu Arg Ala
                500                 505                 510
Phe Cys Ser His Arg Ser Asn Thr Pro Glu Ser Ile Ala Glu Thr Pro
                515                 520                 525
Pro Ala Arg Asp Gly Gly Gly Gly Glu Phe Tyr Gly Tyr Met Thr
                530                 535                 540
Met Asp Arg Pro Leu Ser His Cys Gly Arg Ser Tyr Arg Arg Val Ser
545                 550                 555                 560
Gly Asp Ala Ala Gln Asp Leu Asp Arg Gly Leu Arg Lys Arg Thr Tyr
                565                 570                 575
Ser Leu Thr Thr Pro Ala Arg Gln Arg Pro Val Pro Gln Pro Ser Ser
                580                 585                 590
Ala Ser Leu Asp Glu Tyr Thr Leu Met Arg Ala Thr Phe Ser Gly Ser
                595                 600                 605
Ala Gly Arg Leu Cys Pro Ser Cys Pro Ala Ser Ser Pro Lys Val Ala
                610                 615                 620
Tyr His Pro Tyr Pro Glu Asp Tyr Gly Asp Ile Glu Ile Gly Ser His
625                 630                 635                 640
Arg Ser Ser Ser Asn Leu Gly Ala Asp Asp Gly Tyr Met Pro Met
                645                 650                 655
Thr Pro Gly Ala Ala Leu Ala Gly Ser Gly Ser Gly Ser Cys Arg Ser
                660                 665                 670
Asp Asp Tyr Met Pro Met Ser Pro Ala Ser Val Ser Ala Pro Lys Gln
                675                 680                 685
Ile Leu Gln Pro Arg Ala Ala Ala Ala Ala Ala Val Pro Ser
                690                 695                 700
Ala Gly Pro Ala Gly Pro Ala Pro Thr Ser Ala Ala Gly Arg Thr Phe
705                 710                 715                 720
Pro Ala Ser Gly Gly Tyr Lys Ala Ser Pro Ala Glu Ser Ser
                725                 730                 735
Pro Glu Asp Ser Gly Tyr Met Arg Met Trp Cys Gly Ser Lys Leu Ser
                740                 745                 750
Met Glu His Ala Asp Gly Lys Leu Leu Pro Asn Gly Asp Tyr Leu Asn
                755                 760                 765
Val Ser Pro Ser Asp Ala Val Thr Thr Gly Thr Pro Asp Phe Phe
                770                 775                 780
Ser Ala Ala Leu His Pro Gly Gly Glu Pro Leu Arg Gly Val Pro Gly
785                 790                 795                 800
Cys Cys Tyr Ser Ser Leu Pro Arg Ser Tyr Lys Ala Pro Tyr Thr Cys
                805                 810                 815
Gly Gly Asp Ser Asp Gln Tyr Val Leu Met Ser Ser Pro Val Gly Arg
                820                 825                 830
Ile Leu Glu Glu Glu Arg Leu Glu Pro Gln Ala Thr Pro Gly Pro Ser
                835                 840                 845
```

```
Gln Ala Ala Ser Ala Phe Gly Ala Gly Pro Thr Gln Pro Pro His Pro
    850             855                 860
Val Val Pro Ser Pro Val Arg Pro Ser Gly Gly Arg Pro Glu Gly Phe
865             870                 875                 880
Leu Gly Gln Arg Gly Arg Ala Val Arg Pro Thr Arg Leu Ser Leu Glu
                885                 890                 895
Gly Leu Pro Ser Leu Pro Ser Met His Glu Tyr Pro Leu Pro Pro Glu
                900                 905                 910
Pro Lys Ser Pro Gly Glu Tyr Ile Asn Ile Asp Phe Gly Glu Pro Gly
                915                 920                 925
Ala Arg Leu Ser Pro Pro Ala Pro Pro Leu Leu Ala Ser Ala Ala Ser
    930                 935                 940
Ser Ser Ser Leu Leu Ser Ala Ser Ser Pro Ala Ser Ser Leu Gly Ser
945             950                 955                 960
Gly Thr Pro Gly Thr Ser Ser Asp Ser Arg Gln Arg Ser Pro Leu Ser
                965                 970                 975
Asp Tyr Met Asn Leu Asp Phe Ser Ser Pro Lys Ser Pro Lys Pro Gly
                980                 985                 990
Ala Pro Ser Gly His Pro Val Gly  Ser Leu Asp Gly Leu  Leu Ser Pro
    995                 1000                1005
Glu Ala  Ser Ser Pro Tyr Pro  Pro Leu Pro Pro Arg  Pro Ser Ala
    1010                1015                1020
Ser Pro  Ser Ser Ser Leu Gln  Pro Pro Pro Pro  Pro Ala Pro
    1025                1030                1035
Gly Glu  Leu Tyr Arg Leu Pro  Pro Ala Ser Ala Val  Ala Thr Ala
    1040                1045                1050
Gln Gly  Pro Gly Ala Ala Ser  Ser Leu Ser Ser Asp  Thr Gly Asp
    1055                1060                1065
Asn Gly  Asp Tyr Thr Glu Met  Ala Phe Gly Val Ala  Ala Thr Pro
    1070                1075                1080
Pro Gln  Pro Ile Ala Ala Pro  Pro Lys Pro Glu Ala  Ala Arg Val
    1085                1090                1095
Ala Ser  Pro Thr Ser Gly Val  Lys Arg Leu Ser Leu  Met Glu Gln
    1100                1105                1110
Val Ser  Gly Val Glu Ala Phe  Leu Gln Ala Ser Gln  Pro Pro Asp
    1115                1120                1125
Pro His  Arg Gly Ala Lys Val  Ile Arg Ala Asp Pro  Gln Gly Gly
    1130                1135                1140
Arg Arg  Arg His Ser Ser Glu  Thr Phe Ser Ser Thr  Thr Thr Val
    1145                1150                1155
Thr Pro  Val Ser Pro Ser Phe  Ala His Asn Pro Lys  Arg His Asn
    1160                1165                1170
Ser Ala  Ser Val Glu Asn Val  Ser Leu Arg Lys Ser  Ser Glu Gly
    1175                1180                1185
Gly Val  Gly Val Gly Pro Gly  Gly Gly Asp Glu Pro  Pro Thr Ser
    1190                1195                1200
Pro Arg  Gln Leu Gln Pro Ala  Pro Pro Leu Ala Pro  Gln Gly Arg
    1205                1210                1215
Pro Trp  Thr Pro Gly Gln Pro  Gly Gly Leu Val Gly  Cys Pro Gly
    1220                1225                1230
Ser Gly  Gly Ser Pro Met Arg  Arg Glu Thr Ser Ala  Gly Phe Gln
    1235                1240                1245
```

```
Asn Gly Leu Asn Tyr Ile Ala Ile Asp Val Arg Glu Glu Pro Gly
    1250                1255                1260
Leu Pro Pro Gln Pro Gln Pro Pro Pro Pro Leu Pro Gln Pro
    1265                1270                1275
Gly Asp Lys Ser Ser Trp Gly Arg Thr Arg Ser Leu Gly Gly Leu
    1280                1285                1290
Ile Ser Ala Val Gly Val Gly Ser Thr Gly Gly Cys Gly Gly
    1295                1300                1305
Pro Gly Pro Gly Ala Leu Pro Pro Ala Asn Thr Tyr Ala Ser Ile
    1310                1315                1320
Asp Phe Leu Ser His His Leu Lys Glu Ala Thr Ile Val Lys Glu
    1325                1330                1335

<210> SEQ ID NO 54
<211> LENGTH: 7614
<212> TYPE: DNA
<213> ORGANISM: Homo sapiens

<400> SEQUENCE: 54 aggcccgcc cgggccaacc gcctgcctgg tccgccctct gaccaagatc actccatgga    60
tgaaatgaca gctgtggtga aaattgaaaa aggagttggt ggcaataatg ggggcaatgg   120
taatggtggt ggtgcctttt cacaggctcg aagtagcagc acaggcagta gcagcagcac   180
tggaggagga gggcaggagt cccagccatc ccctttggct ctgctggcag caacttgcag   240
cagaattgag tcacccaatg agaacagcaa caactcccag ggcccgagtc agtcaggggg   300
aacaggtgag cttgacctca cagccacaca actttcacag ggtgccaatg gctggcagat   360
catctcttcc tcctctgggg ctaccctac ctcaaaggaa cagagtggca gcagtaccaa   420
tggcagcaat ggcagtgagt cttccaagaa tcgcacagtc tctggtgggc agtatgttgt   480
ggctgccgct cccaacttac agaaccagca agttctgaca ggactacctg gagtgatgcc   540
taatattcag tatcaagtaa tcccacagtt ccagaccgtt gatgggcaac agctgcagtt   600
tgctgccact ggggcccaag tgcagcagga tggttctggt caaatacaga tcataccagg   660
tgcaaaccaa cagattatca caaatcgagg aagtggaggc aacatcattg ctgctatgcc   720
aaacctactc cagcaggctg tccccctcca aggcctggct aataatgtac tctcaggaca   780
gactcagtat gtgaccaatg taccagtggc cctgaatggg aacatcacct tgctacctgt   840
caacagcgtt tctgcagcta ccttgactcc cagctctcag gcagtcacga tcagcagctc   900
tgggtcccag gagagtggct cacagccgt cacctcaggg actaccatca gttctgccag   960
cttggtatca tcacaagcca gttccagctc ctttttcacc aatgccaata gctactcaac  1020
tactactacc accagcaaca tgggaattat gaactttact accagtggat catcagggac  1080
caactctcaa ggccagacac cccagagggt cagtgggcta caggggtctg atgctctgaa  1140
catccagcaa aaccagacat ctggaggctc attgcaagca ggccagcaaa agaaggaga   1200
gcaaaaccag cagacacagc agcaacaaat tcttatccag cctcagctag ttcaagggg   1260
acaggccctc caggccctcc aagcagcacc attgtcaggg cagaccttta caactcaagc  1320
catctcccag gaaccctcc agaacctcca gcttcaggct gttccaaact ctggtcccat  1380
catcatccgg acaccaacag tggggcccaa tggacaggtc agttggcaga ctctacagct  1440
gcagaacctc caagttcaga cccacaagc ccaaacaatc accttagccc caatgcaggg  1500
tgtttccttg gggcagacca gcagcagcaa caccactctc acacccattg cctcagctgc  1560
ttccattcct gctggcacag tcactgtgaa tgctgctcaa ctctcctcca tgccaggcct  1620
```

```
ccagaccatt aacctcagtg cattgggtac ttcaggaatc caggtgcacc caattcaagg    1680
cctgccgttg gctatagcaa atgccccagg tgatcatgga gctcagcttg gtctccatgg    1740
ggctggtggt gatggaatac atgatgacac agcaggtgga gaggaaggag aaaacagccc    1800
agatgcccaa ccccaagccg gtcggaggac ccggcgggaa gcatgcacct gcccctactg    1860
taaagacagt gaaggaaggg gctcggggga tcctggcaaa agaaacagc atatttgcca    1920 catccaaggc tgtgggaaag tgtatggcaa gacctctcac ctgcgggcac acttgcgctg    1980
gcatacaggc gagaggccat ttatgtgtac ctggtcatac tgtgggaaac gcttcacacg    2040
ttcggatgag ctacagaggc acaaacgtac acacacaggt gagaagaaat ttgcctgccc    2100
tgagtgtcct aagcgcttca tgaggagtga ccacctgtca aaacatatca agacccacca    2160
gaataagaag ggaggcccag tgtagctct gagtgtgggc actttgcccc tggacagtgg    2220
ggcaggttca gaaggcagtg gcactgccac tccttcagcc cttattacca ccaatatggt    2280
agccatggag gccatctgtc cagagggcat tgcccgtctt gccaacagtg gcatcaacgt    2340
catgcaggtg gcagatctgc agtccattaa tatcagtggc aatggcttct gagatcaggc    2400
acccggggcc agagacatat gggccatacc ccttaacccc gggatgcaag gtagcatggg    2460
tccaagagac atggaagaga gagccatgaa gcattaaaat gcatggtgtt gagaagaatc    2520
aggagaggga tacaagagag gagatggggt cccggcaccc atctgtatca tcagtgcctc    2580
tttgaaggtg ggaaacatta gtgaaaattc tgttggtgcc acgctttgat gagcatttgt    2640
ttgaccccag tttcttctta cacttcttac cccagcctac ccttcctgca tttctcttct    2700
cagctcttcc atgatggatt cccccccctt tcctaaagcc atcatgcctt gataaatata    2760
tatgatcatt gaaatacttt ttaacaaaaa acagattcta tattattata tatatatata    2820
tatatataaa gatatataga gatgcattca caggggttgg ctgggaggag aagaccatt    2880 ctgtgaccaa ataccttgg tcatttttt tatattgcct tatttcccta tggctgagcc    2940
ttgttgtgac acatcaagct tttctgtaga tgttgtcttg gcttcccacc agcttaagcg    3000
ttcatatgct ctgcttttag ttcatatata catacataat gttttccctt tcttaatttt    3060
gtctttttgt ttgggatcag cttcttgcac tccttcccta actcaactgt tgccgtctca    3120
tcttctctca tctgatcact tcatgttttg tttttgttac tgcctggatg aggcacttct    3180
gtcaattttt tcaggacctt agttccagca gcagaatgga aaaatccttg aagcccaggc    3240
tgatgcttga agtaactgtg gagggagtgt tcaaaatact actgacgcag gcaccttctt    3300
ggcgctggag agtcaaaggc atctcccttc attagctgct ctgagcatca agaattagaa    3360
gtctttcagt ggaattgtac aagagtccct ttgaagataa taatcttggc tcagtttgta    3420
taaactgtca aattttcaaa aataggtag ggggctttca ctaggaaaat catgtgctca    3480
gaagaggaaa tgactcgtag tcaggttcag gagttagtgg agtatttgga ctttggtact    3540
gctgtcttcc aaggtagctc taagttttga tgtgtgggct tctgagttta tattctgaaa    3600
ggaaatacac ttcttttgaa catccccact aggttctttt ccattgtcaa taaggagcat    3660
cagccagtga atctgtttca ggtttccatt ctgcagaact cctccaaagc atgtgctagt    3720
ggcaagacag tggttcttat gatgttttcc cttaactttt ccttgtatgt tcttgggtgg    3780
ttcctaaggg aaagggaagc acatgatcat gggaatgata gcccagaaca aaaagaaatc    3840
ttgtcttacc acagtgtttt ataggagaga ttgggagaaa tcatcctgtt ttctctgtga    3900
cctgatttca gaagagactg atccaaaaat tataacggca gggaacctag tgcatttggc    3960
```

```
actgagattt aaatgcaacc agaattgtcc tcaaggccca gccataaaag cattgtctct    4020
ctcgaccttc tggtatcttg ttagagagct tttcactgtg aggaagtgtg gaaaaatagc    4080
tctgtgtgtg tgtgtgtgtg tgtgtgtgtg tgtgtgtgta atctgttagg ttggggatag    4140
gttttctgct agccaatatt aaaagagacc tgcaataaaa aaattaccct gatctgatag    4200
aaagcaagtg ttttttgtatg tgtgggtgaa tgtgtgttca tgcccgtata tgtctacaca   4260
cagatgacaa attatatttg aaatcgttgg aaaataaatt cagatcaaaa tgcctttcag    4320
gcccattacc tagaaatcta tcttaaaacc tgggtatgtt cctaaggtca tttctttgct    4380
tatgctaaat taattacaat tatgaatgga ggatattcta ctgtactttt ttaaaaagaa    4440
actattttg tgtttgaaag tgaaaccaac atccagatct atagcagagt ccttattctt     4500
ctcataaatc ttttttacttt ggctacaaat agatgatggt atgattctat tatatatttt   4560
atataaaatc catccaaatt aagttttggg taagtgtgtt gtttaatctg aactatagta    4620
acttaatact ctaaacaata gttcactcca tttggtcctt tctccacaga tgtaattatg    4680
ttttcaactc aggaactatg gcaaggaact ttccccagat caaattctat taacgctgag    4740
atacaagtca tccatgcaca gccactatca tacccttttat tctcactgaa aggcagaact   4800
cagaacctgt tattttatgt ctgtaatcat gtactttggc atcttttgga ggaaaggggc    4860
aggataactc actggaatgt acagtatttt gctagtgcat ttcaaggaat ggaatcttct    4920
ccagtatgaa attaccagat ataaaataat gtaatgatgc tgaggatata agcttttaga   4980
aggtaatttg atggtatttc tttctcgaat gaaaagctgc tggtttaccc tcaaccctat    5040
tcattagcat taccatgagt gaatttatat ctaattattt ccacttgccc tgttctcttc    5100
acaccaagga agctccagat ccagtatctt gtttggcctc aaaacagaag cagcttcttt    5160
tgtctcccag cagtagtgag ccactcagtc tcttccacag gaagtttgga gcctacattc    5220
cttgagtcag gagcttatta cagaaaaacc ccgtttccct gaacttttgg ctaacagaaa    5280
ttaatttaac tgacatgcat attgattctg aaattttttt cctaagtttt tttcattttt    5340
ttgaatgagt tttttaaatt ttttagatga ccaaaacttg cagggcaggg gatgcccaga    5400
agagtggtga gatagtaaaa cacttattcc ctcatccttt caggttttca ggttgcccat    5460
ttatattcat ttacatgtca tttgactgtc tcactttta cccagaacag taacaaccca     5520
caccgtcttc cttcagggat ttccaactgg cactctgtgg gtgctacaca gaatgcaatt   5580
taatggatat ttctcagcct ggttcagaat aaattgatcc tttgatccca gaaagtatat    5640
actgaagtgt gggataaaga ttatgattag gggaggggttg gagacaaaag ctgtaaatta   5700
ctatggctga tttatttcta ctatatacat atatatttt tgcttttgta tatcctatat     5760
aggaaactaa gcattgtatt tttttaaca aatctaaaaa agcactatga actcaggtg     5820
tttgactttc aaaatatatt ttgtattgtt aatatcttca cattgtgtga atactggaag    5880
ctgcagatct ttgctaggac gcaataaatt tatatacttt ttgagggggtt cttctggggt   5940
gctaatcagg cccctgttat gcttaggggg agccctggtg ctacttgctt gaagttttca    6000
gtgtaagtac cctgatgcct tttggacctt gggatcagat caagagtttt ggagatcagg    6060
taccaaggaa ataaggacag tctagctgcc tcaagtgagg ggcccttttgc atagctctcc   6120
ttccccctca ctgaagctgg gtagcctatt ggggttgaga gggaaaatgt gaaatctcag    6180
aatttatctc ccttagaaga gagccagtaa cttatgtaca aggatgaaag aaaggtcgca    6240
gcagtagctt tggggaaagg gaggaagata tggcacttct ccaacccgg aaaacattgc    6300
ttttgaaaac tgctgataaa atatgagccg gttattactt ctgtttggga gactgtgctc    6360
```

```
tctgtggtgc ctctcttggc tctactccac agataccaga cctcttctaa gaggatgagc      6420
agaccagctt tgaggttgac ctgtttctct ttgtctgcct tcccaaaaca ccagccccca      6480
ggaagacatt aagcagcctt aagcttaaat tcctactccc tcttccaaat ttggctcact      6540
tgccttagat ccaaggcagg gaaaggaaaa gaaggggggt ctctggcttt attactcccc      6600
taagtcttta ctctgacttc cccaaaccca gaaagatttt ctccacagtg ttcatttgaa      6660
agaggagtat tttgtcccat tttccccttc ctcattatca aacagcccca gtcttccttg      6720
tctctgctaa gaaagtagag gcatgatgat ctgcctctca actgccctaa gtcctagcta      6780
agtatcaggg gaaaaaaaaa aaaaaaaagc ctaacaaatg ggattagact agggctgcaa      6840
gtagtgagga ttttgttgat acctctgctg ggatgtgtgc tttcccatat cttgccttca      6900
ggaattacac tgtgcctttt ccccagggat atgggctctg tctacccagt gctccagttt      6960
cccggtaact gctcttgaac attgtggaca agggcaggtc ttcatatttt tgatcatccc      7020
tttctcccag tgaaatccca tagcccttac ctagagtcta gggcacaaag acttcgggga      7080
agatacactg agattgacct gaggagacat ctacacacac cagtggcagc tgccccaggg      7140
cctgcttccc cttcctaagt ctgtcatcct ctggaaggga tgggtggtgc tccaatctct      7200
ggtgcctaaa acccaagtt tatttctctc ttaacactgg caataaccag tccacaccac      7260
tgttgccttt taaaacctct taataatctc atgctgtgtt tgttttgatt ccaatccaat      7320
tatcaccagg gctgtgtggg taaatgcttt taaatgctct ctcatcttgt tcttcccct       7380 cacccccac tcttaggtat gtatgatgct aatcttgtcc ctaagtaagt ttcttcctgc       7440
tccttttgta tcttcctttc ttgtctttcc tcctacctt tgtctcttgg tgttttggga      7500
cttttttttt ttttttttg gccttttgta caaagattag tttcaatgta gtctgtagcc      7560
tcctttgtaa accaattaaa aagttttta ataaaaaaaa aaaaaaaaaa aaaa            7614
```

<210> SEQ ID NO 55
<211> LENGTH: 778
<212> TYPE: PRT
<213> ORGANISM: Homo sapiens

<400> SEQUENCE: 55

```
Met Asp Glu Met Thr Ala Val Val Lys Ile Glu Lys Gly Val Gly Gly
1               5                  10                  15

Asn Asn Gly Gly Asn Gly Asn Gly Gly Gly Ala Phe Ser Gln Ala Arg
            20                  25                  30

Ser Ser Ser Thr Gly Ser Ser Ser Thr Gly Gly Gly Gly Gln Glu
        35                  40                  45

Ser Gln Pro Ser Pro Leu Ala Leu Leu Ala Ala Thr Cys Ser Arg Ile
    50                  55                  60

Glu Ser Pro Asn Glu Asn Ser Asn Asn Ser Gln Gly Pro Ser Gln Ser
65                  70                  75                  80

Gly Gly Thr Gly Glu Leu Asp Leu Thr Ala Thr Gln Leu Ser Gln Gly
                85                  90                  95

Ala Asn Gly Trp Gln Ile Ile Ser Ser Ser Gly Ala Thr Pro Thr
            100                 105                 110

Ser Lys Glu Gln Ser Gly Ser Ser Thr Asn Gly Ser Asn Gly Ser Glu
        115                 120                 125

Ser Ser Lys Asn Arg Thr Val Ser Gly Gly Gln Tyr Val Val Ala Ala
    130                 135                 140

Ala Pro Asn Leu Gln Asn Gln Gln Val Leu Thr Gly Leu Pro Gly Val
```

-continued

```
            145                 150                 155                 160
        Met Pro Asn Ile Gln Tyr Gln Val Ile Pro Gln Phe Gln Thr Val Asp
                        165                 170                 175
        Gly Gln Gln Leu Gln Phe Ala Ala Thr Gly Ala Gln Val Gln Gln Asp
                        180                 185                 190
        Gly Ser Gly Gln Ile Gln Ile Pro Gly Ala Asn Gln Gln Ile Ile
                        195                 200                 205
        Thr Asn Arg Gly Ser Gly Gly Asn Ile Ile Ala Met Pro Asn Leu
            210                 215                 220
        Leu Gln Gln Ala Val Pro Leu Gln Gly Leu Ala Asn Asn Val Leu Ser
        225                 230                 235                 240
        Gly Gln Thr Gln Tyr Val Thr Asn Val Pro Val Ala Leu Asn Gly Asn
                        245                 250                 255
        Ile Thr Leu Leu Pro Val Asn Ser Val Ser Ala Ala Thr Leu Thr Pro
                        260                 265                 270
        Ser Ser Gln Ala Val Thr Ile Ser Ser Ser Gly Ser Gln Glu Ser Gly
                        275                 280                 285
        Ser Gln Pro Val Thr Ser Gly Thr Thr Ile Ser Ser Ala Ser Leu Val
            290                 295                 300
        Ser Ser Gln Ala Ser Ser Ser Ser Phe Phe Thr Asn Ala Asn Ser Tyr
        305                 310                 315                 320
        Ser Thr Thr Thr Thr Thr Ser Asn Met Gly Ile Met Asn Phe Thr Thr
                        325                 330                 335
        Ser Gly Ser Ser Gly Thr Asn Ser Gln Gly Gln Thr Pro Gln Arg Val
                        340                 345                 350
        Ser Gly Leu Gln Gly Ser Asp Ala Leu Asn Ile Gln Gln Asn Gln Thr
                        355                 360                 365
        Ser Gly Gly Ser Leu Gln Ala Gly Gln Gln Lys Glu Gly Glu Gln Asn
                        370                 375                 380
        Gln Gln Thr Gln Gln Gln Ile Leu Ile Gln Pro Gln Leu Val Gln
        385                 390                 395                 400
        Gly Gly Gln Ala Leu Gln Ala Leu Gln Ala Ala Pro Leu Ser Gly Gln
                        405                 410                 415
        Thr Phe Thr Thr Gln Ala Ile Ser Gln Glu Thr Leu Gln Asn Leu Gln
                        420                 425                 430
        Leu Gln Ala Val Pro Asn Ser Gly Pro Ile Ile Ile Arg Thr Pro Thr
                        435                 440                 445
        Val Gly Pro Asn Gly Gln Val Ser Trp Gln Thr Leu Gln Leu Gln Asn
        450                 455                 460
        Leu Gln Val Gln Asn Pro Gln Ala Gln Thr Ile Thr Leu Ala Pro Met
        465                 470                 475                 480
        Gln Gly Val Ser Leu Gly Gln Thr Ser Ser Ser Asn Thr Thr Leu Thr
                        485                 490                 495
        Pro Ile Ala Ser Ala Ala Ser Ile Pro Ala Gly Thr Val Thr Val Asn
                        500                 505                 510
        Ala Ala Gln Leu Ser Ser Met Pro Gly Leu Gln Thr Ile Asn Leu Ser
                        515                 520                 525
        Ala Leu Gly Thr Ser Gly Ile Gln Val His Pro Ile Gln Gly Leu Pro
                        530                 535                 540
        Leu Ala Ile Ala Asn Ala Pro Gly Asp His Gly Ala Gln Leu Gly Leu
        545                 550                 555                 560
        His Gly Ala Gly Gly Asp Gly Ile His Asp Asp Thr Ala Gly Gly Glu
                        565                 570                 575
```

```
Glu Gly Glu Asn Ser Pro Asp Ala Gln Pro Gln Ala Gly Arg Arg Thr
            580                 585                 590
Arg Arg Glu Ala Cys Thr Cys Pro Tyr Cys Lys Asp Ser Glu Gly Arg
        595                 600                 605
Gly Ser Gly Asp Pro Gly Lys Lys Lys Gln His Ile Cys His Ile Gln
    610                 615                 620
Gly Cys Gly Lys Val Tyr Gly Lys Thr Ser His Leu Arg Ala His Leu
625                 630                 635                 640
Arg Trp His Thr Gly Glu Arg Pro Phe Met Cys Thr Trp Ser Tyr Cys
                645                 650                 655
Gly Lys Arg Phe Thr Arg Ser Asp Glu Leu Gln Arg His Lys Arg Thr
            660                 665                 670
His Thr Gly Glu Lys Lys Phe Ala Cys Pro Glu Cys Pro Lys Arg Phe
        675                 680                 685
Met Arg Ser Asp His Leu Ser Lys His Ile Lys Thr His Gln Asn Lys
    690                 695                 700
Lys Gly Gly Pro Gly Val Ala Leu Ser Val Gly Thr Leu Pro Leu Asp
705                 710                 715                 720
Ser Gly Ala Gly Ser Glu Gly Ser Gly Thr Ala Thr Pro Ser Ala Leu
                725                 730                 735
Ile Thr Thr Asn Met Val Ala Met Glu Ala Ile Cys Pro Glu Gly Ile
            740                 745                 750
Ala Arg Leu Ala Asn Ser Gly Ile Asn Val Met Gln Val Ala Asp Leu
        755                 760                 765
Gln Ser Ile Asn Ile Ser Gly Asn Gly Phe
    770                 775

<210> SEQ ID NO 56
<211> LENGTH: 5497
<212> TYPE: DNA
<213> ORGANISM: Homo sapiens

<400> SEQUENCE: 56
agttccggcc catgttgttt cggccgagga gccgtcgccg ccatttcaag accgtactag      60
gtagatggtc aattagagtt cccagggttt gaagcctgta actgctgccg ccgctcaagc     120
cctccagagc attgctacgg ctgctgccct tgtactacta cctccaaata cgttcttgct     180
ggtagtggcg gcagcaggac caattacctc ttttttgctc tccctcgaga agctccagat     240
ggcgtcttcc gtgggcaacg tggccgacag cacagaacca acgaaacgta tgctttcctt     300
ccaagggtta gctgagttgg cacatcgaga atatcaggca ggagattttg aggcagctga     360
gagacactgc atgcagctct ggagacaaga gccagacaat actggtgtgc ttttattact     420
ttcatctata cacttccagt gtcgaaggct ggacagatct gctcacttta gcactctggc     480
aattaaacag aaccccttc tggcagaagc ttattcgaat ttggggaatg tgtacaagga     540
aagagggcag ttgcaggagg caattgagca ttatcgacat gcattgcgtc tcaaacctga     600
tttcatcgat ggttatatta acctggcagc cgccttggta gcagcgggtg acatggaagg     660
ggcagtacaa gcttacgtct ctgctcttca gtacaatcct gatttgtact gtgttcgcag     720
tgacctgggg aacctgctca aagccctggg tcgcttggaa gaagccaagg catgttattt     780
gaaagcaatt gagacgcaac cgaactttgc agtagcttgg agtaatcttg gctgtgtttt     840
caatgcacaa ggggaaattt ggcttgcaat tcatcacttt gaaaaggctg tcacccttga     900
cccaaacttt ctggatgctt atatcaattt aggaaatgtc ttgaaagagg cacgcatttt     960
```

```
tgacagagct gtggcagctt atcttcgtgc cctaagtttg agtccaaatc acgcagtggt    1020
gcacggcaac ctggcttgtg tatactatga gcaaggcctg atagatctgg caatagacac    1080
ctacaggcgg gctatcgaac tacaaccaca tttccctgat gcttactgca acctagccaa    1140
tgctctcaaa gagaagggca gtgttgctga agcagaagat tgttataata cagctctccg    1200
tctgtgtccc acccatgcag actctctgaa taacctagcc aatatcaaac gagaacaggg    1260
aaacattgaa gaggcagttc gcttgtatcg taaagcatta gaagtcttcc cagagtttgc    1320
tgctgcccat tcaaatttag caagtgtact gcagcagcag ggaaaactgc aggaagctct    1380
gatgcattat aaggaggcta ttcgaatcag tcctaccttt gctgatgcct actctaatat    1440
gggaaacact ctaaaggaga tgcaggatgt tcagggagcc ttgcagtgtt atacgcgtgc    1500
catccaaatt aatcctgcat tgcagatgc acatagcaat ctggcttcca ttcataagga    1560
ttcagggaat attccagaag ccatagcttc ttaccgcacg gctctgaaac ttaagcctga    1620 tttttcctgat gcttattgta acttggctca ttgcctgcag attgtctgtg attggacaga    1680
ctatgatgag cgaatgaaga agttggtcag tattgtggct gaccagttag agaagaatag    1740 gttgcccttct gtgcatcctc atcatagtat gctatatcct ctttctcatg gcttcaggaa    1800
ggctattgct gagaggcacg gcaacctgtg cttagataag attaatgttc ttcataaacc    1860
accatatgaa catccaaaag acttgaagct cagtgatggt cggctgcgtg taggatatgt    1920
gagttccgac tttgggaatc atcctacttc tcaccttatg cagtctattc caggcatgca    1980
caatcctgat aaatttgagg tgttctgtta tgccctgagc ccagacgatg cacaaaactt    2040
ccgagtgaag gtgatggcag aagccaatca tttcattgat ctttctcaga ttccatgcaa    2100
tggaaaagca gctgatcgca tccatcagga tggaattcat atccttgtaa atatgaatgg    2160
ctatactaag ggcgctcgaa atgagctttt tgctctcagg ccagctccta ttcaggcaat    2220
gtggctggga taccctggga cgagtggtgc gcttttcatg gattatatta tcactgatca    2280
ggaaacttcg ccagctgaag ttgctgagca gtattccgag aaattggctt atatgcccca    2340
cacttttttt attggtgatc atgctaatat gttccctcac ctgaagaaaa aagcagtcat    2400
cgattttaag tccaatgggc acatttatga caatcggata gttctgaatg gcatcgacct    2460
caaagcattt cttgatagtc taccagatgt gaaaattgtc aagatgaagt gtcctgatgg    2520
aggagacaat gcagatagca gtaacacagc tcttaatatg cctgttattc ctatgaatac    2580
tattgcagaa gcagttattg aaatgattaa ccgaggacag attcaaataa caattaatgg    2640
attcagtatt agcaatggac tggcaactac tcagatcaac aataaggctg caactggaga    2700
ggaggttccc cgtaccatta ttgtaaccac ccgttctcag tacgggttac cagaagatgc    2760
catcgtatac tgtaacttta atcagttgta taaaattgac ccttctactt tgcagatgtg    2820
ggcaaacatt ctgaagcgtg ttcccaatag tgtactctgg ctgttgcgtt ttccagcagt    2880 aggaaacct aatattcaac agtatgcaca aacatgggc ctgccccaga accgtatcat    2940 ttttttcacct gttgctccta agaggaaca cgtcaggaga ggccagctgg ctgatgtctg    3000
cttggacact ccactctgta atgggcacac cacagggatg gatgtcctct gggcagggac    3060
ccccatggtg actatgccag agagactct tgcttctcga gttgcagcat cccagctcac    3120
ttgcttaggt tgtcttgagc ttattgctaa aaacagacaa gaatatgaag acatagctgt    3180
gaagctggga actgatctag aatacctgaa gaaagttcgt ggcaaagtct ggaagcaaag    3240
aatatctagc cctctgttca acaccaaaca atacacaatg gaactagagc ggctctatct    3300
```

```
acagatgtgg gagcattatg cagctggcaa caaacctgac cacatgatta agcctgttga    3360
agtcactgag tcagcataaa taaagactgc acaggagaat tacccctata cctgagcctc    3420
aaccttctgg gggaaaggga actagataac atacttctta cttgtctgta cagtaccttg    3480
ttgcagatgg gtgatatata atggtaatag aatagcacag ccagacttgc ttcctgcatg    3540
gtagggagag acacaaaaga tgggaaactg cttttccaca aggaatctcc gtagaatttt    3600
gcggcgacca gatggtgcat aggtctggaa ggtctgatct cccttggtct tccatgggat    3660
ggttagtgtg gaggggagat atagattgtc cggccgcttt gtgattccat ggattgattc    3720
agtcttctgg attttttttt ctttatattt tgggtactgg agcttttaaa aatgtttggt    3780
ttcaggtatt tttattcatg tgaagtgtat atgattctct tgagataagg ttttaagcta    3840
aaatgttact ccctgtttta gtttctgaac tctgacagat tgacagggac tttgctggtg    3900
tagtcttttt ataggtttta taaccacttt gagcctatat cagtcgtttt agtgtctgac    3960
ctaatatttg gagctatcag tgctttgttg atttagatga tgactcaaga ttttttctgg    4020
tccatttccc atttccttt cttccctgac ccccataccc tcacccttaa aattctcctg    4080
taactcaact aacaaaatca agcctgattc aaaacatcct agggtgtttt aaacacacca    4140
tctggtgcca aatgaagatt tttaggagtg attactaatt atcaagggca cagttgtggt    4200
actgtcattg ataataatat agttttttt tttttcctaa ttttgacctg tttcaccagt    4260
gttttaccct tgactgcccc ttctatgctg cttccaaaag tgatagtgtg tgtaagattt    4320
ttaccttcct ttctaaagtt ttttttttt ttttttaagt gagtcctgtt cttcctattt    4380
ctttcagcag aaatgaaatc ccaggtaagt ataagtattc aagtatttga tcagtaagtc    4440
acagttatct ccagtgcatt aaataacctt catcaagaaa taggttatag gtaaaatctc    4500
tgaaggatca tctatgtatt caagtaatta tttttagat aataactgtc ttctggactt    4560
ggtcttgaag tctgtacaga ttcagcctca gtagtagcga actgcactgc tgtttggttt    4620
ggagtacaaa ttagacttat agtcctcctg gaacttgagt tattaaaatc ataggaataa    4680
aattatggga tctcaacaaa gggtcgaggg tttgaggctt aaacaagcca acatatgaat    4740
atatgttttg tctcgctata ctgcacttac gctatccagt tgcaggtaat tttttgtctg    4800
ctagtagtgt tctagattat gtcttttccaa agcgctgagg ctgtgcacct attctgtagt    4860
tgcagctgat gcctgaatgt atcctagctg acaaattatt gattaataag aacttgaatt    4920
tctggaagat tcttactgtt aaccaaattt tgagcaagga gtctcaaagg taattctgaa    4980
ccagaattac atgttaatga acagtgtacc ttttaacagt gtaaatcacg gaatatccgt    5040
gaagggattt cttaatttat ttttttaccgg ttgattgaaa tatcagttaa aggttgccag    5100
catggttgca gataaactga tgtttgaaat tcgctgaaat acttaatgtg aataggata    5160
atatacttcc aatgccctca aggctgtgac cttacagcca ttttacatag cacatcattc    5220
ctcctatagg gatgaacttt ttcctggcac gaaaagtagc cgctctggtt gaagctttgc    5280
ttattgtaac aggcttttat ttccaggtaa tatgtcttgg aagacttaat tctgattaga    5340
gatatagata ttactggaaa ctaattgttt tttttctatt gtactctgct ttatcaaaga    5400
agtaaaacat ttaaatcgta ctacagaaat taagatgttg tcttgcgatc cttaataaat    5460
gaatgatttc cctttaatac ggaaaaaaaa aaaaaaa                              5497
```

<210> SEQ ID NO 57
<211> LENGTH: 1046
<212> TYPE: PRT
<213> ORGANISM: Homo sapiens

<400> SEQUENCE: 57

```
Met Ala Ser Ser Val Gly Asn Val Ala Asp Ser Thr Glu Pro Thr Lys
1               5                   10                  15

Arg Met Leu Ser Phe Gln Gly Leu Ala Glu Leu Ala His Arg Glu Tyr
            20                  25                  30

Gln Ala Gly Asp Phe Glu Ala Glu Arg His Cys Met Gln Leu Trp
        35                  40                  45

Arg Gln Glu Pro Asp Asn Thr Gly Val Leu Leu Leu Ser Ser Ile
    50                  55                  60

His Phe Gln Cys Arg Arg Leu Asp Arg Ser Ala His Phe Ser Thr Leu
65              70                  75                  80

Ala Ile Lys Gln Asn Pro Leu Leu Ala Glu Ala Tyr Ser Asn Leu Gly
                85                  90                  95

Asn Val Tyr Lys Glu Arg Gly Gln Leu Gln Glu Ala Ile Glu His Tyr
            100                 105                 110

Arg His Ala Leu Arg Leu Lys Pro Asp Phe Ile Asp Gly Tyr Ile Asn
        115                 120                 125

Leu Ala Ala Ala Leu Val Ala Ala Gly Asp Met Glu Gly Ala Val Gln
130                 135                 140

Ala Tyr Val Ser Ala Leu Gln Tyr Asn Pro Asp Leu Tyr Cys Val Arg
145                 150                 155                 160

Ser Asp Leu Gly Asn Leu Leu Lys Ala Leu Gly Arg Leu Glu Glu Ala
                165                 170                 175

Lys Ala Cys Tyr Leu Lys Ala Ile Glu Thr Gln Pro Asn Phe Ala Val
            180                 185                 190

Ala Trp Ser Asn Leu Gly Cys Val Phe Asn Ala Gln Gly Glu Ile Trp
        195                 200                 205

Leu Ala Ile His His Phe Glu Lys Ala Val Thr Leu Asp Pro Asn Phe
210                 215                 220

Leu Asp Ala Tyr Ile Asn Leu Gly Asn Val Leu Lys Glu Ala Arg Ile
225                 230                 235                 240

Phe Asp Arg Ala Val Ala Ala Tyr Leu Arg Ala Leu Ser Leu Ser Pro
                245                 250                 255

Asn His Ala Val Val His Gly Asn Leu Ala Cys Val Tyr Tyr Glu Gln
            260                 265                 270

Gly Leu Ile Asp Leu Ala Ile Asp Thr Tyr Arg Arg Ala Ile Glu Leu
        275                 280                 285

Gln Pro His Phe Pro Asp Ala Tyr Cys Asn Leu Ala Asn Ala Leu Lys
    290                 295                 300

Glu Lys Gly Ser Val Ala Glu Ala Glu Asp Cys Tyr Asn Thr Ala Leu
305                 310                 315                 320

Arg Leu Cys Pro Thr His Ala Asp Ser Leu Asn Asn Leu Ala Asn Ile
                325                 330                 335

Lys Arg Glu Gln Gly Asn Ile Glu Glu Ala Val Arg Leu Tyr Arg Lys
            340                 345                 350

Ala Leu Glu Val Phe Pro Glu Phe Ala Ala Ala His Ser Asn Leu Ala
        355                 360                 365

Ser Val Leu Gln Gln Gln Gly Lys Leu Gln Glu Ala Leu Met His Tyr
    370                 375                 380

Lys Glu Ala Ile Arg Ile Ser Pro Thr Phe Ala Asp Ala Tyr Ser Asn
385                 390                 395                 400

Met Gly Asn Thr Leu Lys Glu Met Gln Asp Val Gln Gly Ala Leu Gln
```

```
            405                 410                 415
Cys Tyr Thr Arg Ala Ile Gln Ile Asn Pro Ala Phe Ala Asp Ala His
            420                 425                 430

Ser Asn Leu Ala Ser Ile His Lys Asp Ser Gly Asn Ile Pro Glu Ala
            435                 440                 445

Ile Ala Ser Tyr Arg Thr Ala Leu Lys Leu Lys Pro Asp Phe Pro Asp
            450                 455                 460

Ala Tyr Cys Asn Leu Ala His Cys Leu Gln Ile Val Cys Asp Trp Thr
465                 470                 475                 480

Asp Tyr Asp Glu Arg Met Lys Lys Leu Val Ser Ile Val Ala Asp Gln
                485                 490                 495

Leu Glu Lys Asn Arg Leu Pro Ser Val His Pro His His Ser Met Leu
                500                 505                 510

Tyr Pro Leu Ser His Gly Phe Arg Lys Ala Ile Ala Glu Arg His Gly
                515                 520                 525

Asn Leu Cys Leu Asp Lys Ile Asn Val Leu His Lys Pro Pro Tyr Glu
            530                 535                 540

His Pro Lys Asp Leu Lys Leu Ser Asp Gly Arg Leu Arg Val Gly Tyr
545                 550                 555                 560

Val Ser Ser Asp Phe Gly Asn His Pro Thr Ser His Leu Met Gln Ser
                565                 570                 575

Ile Pro Gly Met His Asn Pro Asp Lys Phe Glu Val Phe Cys Tyr Ala
                580                 585                 590

Leu Ser Pro Asp Asp Gly Thr Asn Phe Arg Val Lys Val Met Ala Glu
                595                 600                 605

Ala Asn His Phe Ile Asp Leu Ser Gln Ile Pro Cys Asn Gly Lys Ala
            610                 615                 620

Ala Asp Arg Ile His Gln Asp Gly Ile His Ile Leu Val Asn Met Asn
625                 630                 635                 640

Gly Tyr Thr Lys Gly Ala Arg Asn Glu Leu Phe Ala Leu Arg Pro Ala
                645                 650                 655

Pro Ile Gln Ala Met Trp Leu Gly Tyr Pro Gly Thr Ser Gly Ala Leu
                660                 665                 670

Phe Met Asp Tyr Ile Ile Thr Asp Gln Glu Thr Ser Pro Ala Glu Val
            675                 680                 685

Ala Glu Gln Tyr Ser Glu Lys Leu Ala Tyr Met Pro His Thr Phe Phe
            690                 695                 700

Ile Gly Asp His Ala Asn Met Phe Pro His Leu Lys Lys Lys Ala Val
705                 710                 715                 720

Ile Asp Phe Lys Ser Asn Gly His Ile Tyr Asp Asn Arg Ile Val Leu
                725                 730                 735

Asn Gly Ile Asp Leu Lys Ala Phe Leu Asp Ser Leu Pro Asp Val Lys
            740                 745                 750

Ile Val Lys Met Lys Cys Pro Asp Gly Gly Asp Asn Ala Asp Ser Ser
            755                 760                 765

Asn Thr Ala Leu Asn Met Pro Val Ile Pro Met Asn Thr Ile Ala Glu
            770                 775                 780

Ala Val Ile Glu Met Ile Asn Arg Gly Gln Ile Gln Ile Thr Ile Asn
785                 790                 795                 800

Gly Phe Ser Ile Ser Asn Gly Leu Ala Thr Thr Gln Ile Asn Asn Lys
                805                 810                 815

Ala Ala Thr Gly Glu Glu Val Pro Arg Thr Ile Ile Val Thr Thr Arg
            820                 825                 830
```

Ser Gln Tyr Gly Leu Pro Glu Asp Ala Ile Val Tyr Cys Asn Phe Asn
            835                 840                 845

Gln Leu Tyr Lys Ile Asp Pro Ser Thr Leu Gln Met Trp Ala Asn Ile
    850                 855                 860

Leu Lys Arg Val Pro Asn Ser Val Leu Trp Leu Leu Arg Phe Pro Ala
865                 870                 875                 880

Val Gly Glu Pro Asn Ile Gln Gln Tyr Ala Gln Asn Met Gly Leu Pro
                885                 890                 895

Gln Asn Arg Ile Ile Phe Ser Pro Val Ala Pro Lys Glu Glu His Val
            900                 905                 910

Arg Arg Gly Gln Leu Ala Asp Val Cys Leu Asp Thr Pro Leu Cys Asn
            915                 920                 925

Gly His Thr Thr Gly Met Asp Val Leu Trp Ala Gly Thr Pro Met Val
        930                 935                 940

Thr Met Pro Gly Glu Thr Leu Ala Ser Arg Val Ala Ala Ser Gln Leu
945                 950                 955                 960

Thr Cys Leu Gly Cys Leu Glu Leu Ile Ala Lys Asn Arg Gln Glu Tyr
                965                 970                 975

Glu Asp Ile Ala Val Lys Leu Gly Thr Asp Leu Glu Tyr Leu Lys Lys
            980                 985                 990

Val Arg Gly Lys Val Trp Lys Gln Arg Ile Ser Ser Pro Leu Phe Asn
            995                 1000                1005

Thr Lys Gln Tyr Thr Met Glu Leu Glu Arg Leu Tyr Leu Gln Met
    1010                1015                1020

Trp Glu His Tyr Ala Ala Gly Asn Lys Pro Asp His Met Ile Lys
    1025                1030                1035

Pro Val Glu Val Thr Glu Ser Ala
    1040                1045

<210> SEQ ID NO 58
<211> LENGTH: 11242
<212> TYPE: DNA
<213> ORGANISM: Homo sapiens

<400> SEQUENCE: 58
tttttttttt ttttttttga gaaagggaa tttcatccca aataaaagga atgaagtctg      60
gctccggagg agggtccccg acctcgctgt gggggctcct gtttctctcc gccgcgctct    120
cgctctggcc gacgagtgga gaaatctgcg ggccaggcat cgacatccgc aacgactatc    180
agcagctgaa gcgcctggag aactgcacgg tgatcgaggg ctacctccac atcctgctca    240
tctccaaggc cgaggactac cgcagctacc gcttccccaa gctcacggtc attaccgagt    300
acttgctgct gttccgagtg gctggcctcg agagcctcgg agacctcttc cccaacctca    360
cggtcatccg cggctggaaa ctcttctaca actacgccct ggtcatcttc gagatgacca    420
atctcaagga tattgggctt acaacctga ggaacattac tcgggggggcc atcaggattg    480 agaaaaatgc tgacctctgt tacctctcca ctgtggactg gtccctgatc ctggatgcgg    540
tgtccaataa ctacattgtg ggaataagc ccccaaagga atgtggggac ctgtgtccag    600
ggaccatgga ggagaagccg atgtgtgaga agaccaccat caacaatgag tacaactacc    660
gctgctggac cacaaaccgc tgccagaaaa tgtgcccaag cacgtgtggg aagcgggcgt    720
gcaccgagaa caatgagtgc tgccaccccg agtgcctggg cagctgcagc gcgcctgaca    780
acgacacggc ctgtgtagct tgccgccact actactatgc cggtgtctgt gtgcctgcct    840

```
gcccgcccaa cacctacagg tttgagggct ggcgctgtgt ggaccgtgac ttctgcgcca    900
acatcctcag cgccgagagc agcgactccg aggggtttgt gatccacgac ggcgagtgca    960
tgcaggagtg cccctcgggc ttcatccgca acggcagcca gagcatgtac tgcatccctt   1020
gtgaaggtcc ttgcccgaag gtctgtgagg aagaaaagaa aacaaagacc attgattctg   1080
ttacttctgc tcagatgctc caaggatgca ccatcttcaa gggcaatttg ctcattaaca   1140
tccgacgggg gaataacatt gcttcagagc tggagaactt catggggctc atcgaggtgg   1200
tgacgggcta cgtgaagatc cgccattctc atgccttggt ctccttgtcc ttcctaaaaa   1260
accttcgcct catcctagga gaggagcagc tagaagggaa ttactccttc tacgtcctcg   1320
acaaccagaa cttgcagcaa ctgtgggact gggaccaccg caacctgacc atcaaagcag   1380
ggaaaatgta ctttgctttc aatcccaaat tatgtgtttc cgaaatttac cgcatggagg   1440
aagtgacggg gactaaaggg cgccaaagca aggggacat aaacaccagg aacaacgggg   1500
agagagcctc ctgtgaaagt gacgtcctgc atttcacctc caccaccacg tcgaagaatc   1560
gcatcatcat aacctggcac cggtaccggc cccctgacta cagggatctc atcagcttca   1620
ccgtttacta caaggaagca cccttttaaga atgtcacaga gtatgatggg caggatgcct   1680
gcggctccaa cagctggaac atggtggacg tggacctccc gcccaacaag gacgtggagc   1740
ccggcatctt actacatggg ctgaagccct ggactcagta cgccgtttac gtcaaggctg   1800
tgaccctcac catggtggag aacgaccata tccgtggggc caagagtgag atcttgtaca   1860
ttcgcaccaa tgcttcagtt ccttccattc ccttggacgt tctttcagca tcgaactcct   1920
cttctcagtt aatcgtgaag tggaaccctc cctctctgcc caacggcaac ctgagttact   1980
acattgtgcg ctggcagcgg cagcctcagg acggctacct ttaccggcac aattactgct   2040
ccaaagacaa aatccccatc aggaagtatg ccgacgcac catcgacatt gaggaggtca   2100
cagagaaccc caagactgag gtgtgtggtg gggagaaagg gccttgctgc gcctgcccca   2160
aaactgaagc cgagaagcag gccgagaagg aggaggctga ataccgcaaa gtctttgaga   2220
atttcctgca caactccatc ttcgtgccca cctgaaag gaagcggaga gatgtcatgc   2280
aagtggccaa caccaccatg tccagccgaa gcaggaacac cacggccgca gacacctaca   2340
acatcaccga cccggaagag ctggagacag agtacccttt ctttgagagc agagtggata   2400
acaaggagag aactgtcatt tctaaccttc ggcctttcac attgtaccgc atcgatatcc   2460
acagctgcaa ccacgaggct gagaagctgg gctgcagcgc ctccaacttc gtctttgcaa   2520
ggactatgcc cgcagaagga gcagatgaca ttcctgggcc agtgacctgg gagccaaggc   2580
ctgaaaactc catctttta aagtggccgg aacctgagaa tcccaatgga ttgattctaa   2640
tgtatgaaat aaaatacgga tcacaagttg aggatcagcg agaatgtgtg tccagacagg   2700
aatacaggaa gtatggaggg gccaagctaa accggctaaa cccggggaac tacacagccc   2760
ggattcaggc cacatctctc tctgggaatg ggtcgtggac agatcctgtg ttcttctatg   2820
tccaggccaa aacaggatat gaaaacttca tccatctgat catcgctctg cccgtcgctg   2880
tcctgttgat cgtgggaggg ttggtgatta tgctgtacgt cttccataga aagagaaata   2940
acagcaggct ggggaatgga gtgctgtatg cctctgtgaa cccggagtac ttcagcgctg   3000
ctgatgtgta cgttcctgat gagtgggagg tggctcggga agatcacc atgagccggg   3060
aacttgggca ggggtcgttt gggatggtct atgaaggagt tgccaagggt gtggtgaaag   3120
atgaacctga aaccagagtg ccattaaaa cagtgaacga ggccgcaagc atgcgtgaga   3180
ggattgagtt tctcaacgaa gcttctgtga tgaaggagtt caattgtcac catgtggtgc   3240
```

```
gattgctggg tgtggtgtcc caaggccagc aacactggt catcatggaa ctgatgacac    3300
ggggcgatct caaaagttat ctccggtctc tgaggccaga atggagaat aatccagtcc    3360
tagcacctcc aagcctgagc aagatgattc agatggccgg agagattgca gacggcatgg    3420
catacctcaa cgccaataag ttcgtccaca gagaccttgc tgcccggaat tgcatggtag    3480
ccgaagattt cacagtcaaa atcggagatt ttggtatgac gcgagatatc tatgagacag    3540
actattaccg gaaaggaggg aaagggctgc tgcccgtgcg ctggatgtct cctgagtccc    3600
tcaaggatgg agtcttcacc acttactcgg acgtctggtc cttcggggtc gtcctctggg    3660
agatcgccac actggccgag cagccctacc agggcttgtc caacgagcaa gtccttcgct    3720
tcgtcatgga gggcggcctt ctggacaagc agacaactg tcctgacatg ctgtttgaac    3780
tgatgcgcat gtgctggcag tataacccca agatgaggcc ttccttcctg gagatcatca    3840
gcagcatcaa agaggagatg gagcctggct ccgggaggt ctccttctac tacagcgagg    3900
agaacaagct gcccgagccg gaggagctgg acctggagcc agagaacatg gagagcgtcc    3960
ccctggaccc ctcggcctcc tcgtcctccc tgccactgcc cgacagacac tcaggacaca    4020
aggccgagaa cggcccggc cctggggtgc tggtcctccg cgccagcttc gacgagagac    4080
agccttacgc ccacatgaac gggggccgca agaacgagcg ggccttgccg ctgccccagt    4140
cttcgacctg ctgatccttg gatcctgaat ctgtgcaaac agtaacgtgt gcgcacgcgc    4200
agcggggtgg gggggagag agagttttaa caatccattc acaagcctcc tgtacctcag    4260
tggatcttca gaactgccct tgctgcccgc gggagacagc ttctctgcag taaaacacat    4320
ttgggatgtt ccttttttca atatgcaagc agcttttat tccctgccca aaccccttaac   4380
tgacatgggc ctttaagaac cttaatgaca acacttaata gcaacagagc acttgagaac    4440
cagtctcctc actctgtccc tgtccttccc tgttctccct ttctctctcc tctctgcttc    4500
ataacggaaa aataattgcc acaagtccag ctgggaagcc cttttttatca gtttgaggaa    4560
gtggctgtcc ctgtggcccc atccaaccac tgtacacacc cgcctgacac cgtgggtcat    4620
tacaaaaaaa cacgtggaga tggaaatttt tacctttatc tttcacctttc taggacat    4680
gaaatttaca aagggccatc gttcatccaa ggctgttacc attttaacgc tgcctaattt    4740
tgccaaaatc ctgaactttc tccctcatcg gcccggcgct gattcctcgt gtccggaggc    4800
atgggtgagc atggcagctg gttgctccat ttgagagaca cgctggcgac acactccgtc    4860
catccgactg cccctgctgt gctgctcaag gccacaggca cacaggtctc attgcttctg    4920
actagattat tatttggggg aactggacac aataggtctt tctctcagtg aaggtgggga    4980
gaagctgaac cggcttccct gccctgcctc ccagccccc tgcccaaccc ccaagaatct    5040
ggtggccatg ggccccgaag cagcctggcg gacaggcttg gagtcaaggg gccccatgcc    5100
tgcttctctc ccagccccag ctcccccgcc cgcccccaag gacacagatg ggaagggggtt   5160
tccagggact cagcccccact gttgatgcag gtttgcaagg aaagaaattc aaacaccaca    5220
acagcagtaa gaagaaaagc agtcaatgga ttcaagcatt ctaagctttg ttgacatttt    5280
ctctgttcct aggacttctt catgggtctt acagttctat gttagaccat gaaacatttg    5340
catacacatc gtctttaatg tcacttttat aacttttta cggttcagat attcatctat    5400
acgtctgtac agaaaaaaaa aagctgctat ttttttgtt cttgatcttt gtggatttaa    5460
tctatgaaaa ccttcaggtc caccctctcc cctttctgct cactccaaga aacttcttat    5520
gctttgtact agagtgcgtg actttcttcc tcttttcccg gtaatggata cttctatcac    5580
```

```
ataatttgcc atgaactgtt ggatgccttt ttataaatac atccccatc cctgctccca   5640
cctgccccctt tagttgtttt ctaacccgta ggctctctgg gcacgaggca gaaagcaggc   5700
cgggcaccca tcctgagagg gccgcgctcc tctccccagc ctgccctcac agcattggag   5760
cctgttacag tgcaagacat gatacaaact caggtcagaa aaacaaaggt taaatatttc   5820
acacgtcttt gttcagtgtt tccactcacc gtggttgaga agcctcaccc tctctttccc   5880
ttgcctttgc ttaggttgtg acacacatat atatatattt ttttaattct tgggtacaac   5940
agcagtgtta accgcagaca ctaggcattt ggattactat ttttcttaat ggctatttaa   6000
tccttccatc ccacgaaaaa cagctgctga gtccaaggga gcagcagagc gtggtccggc   6060
agggcctgtt gtggccctcg ccacccccct caccggaccg actgacctgt ctttggaacc   6120
agaacatccc aagggaactc cttcgcactg gcgttgagtg ggaccccggg atccaggctg   6180
gcccagggcg gcaccctcag ggctgtgccc gctggagtgc taggtggagg cagcacagac   6240
gccacggtgg cccaagagcc cctttgcttc ttgctggggg accagggctg tggtgctggc   6300
ccactttccc tcggccagga atccaggtcc ttggggccca ggggtcttgt cttgtttcat   6360
ttttagcact tctcaccaga gagatgacag cacaagagtt gcttctggga tagaaatgtt   6420
taggagtaag aacaaagctg ggatacggtg attgctagtg gtgactgaag attcaacaca   6480
gaaaagaaag tttatacggc ttttttgctg gtcagcagtt tgtcccactg ctttctctag   6540
tctctatccc atagcgtgtt cccttttaaaa aaaaaaaaaa ggtattatat gtaggagttt   6600
tctttaatt tattttgtga taaattacca gtttcaatca ctgtagaaaa gccccattat   6660
gaatttaaat ttcaaggaaa gggtgtgtgt gtgtgtatgt gtggggtgtg tgtgtgtgag   6720
agtgatggga cagttcttga tttttgggt tttttttccc ccaaacattt atctacctca   6780
ctcttatttt ttatatgtgt atatagacaa aagaatacat ctcaccttc tcagcacctg   6840
acaataggcc gttgatactg gtaacctcat ccacgccaca ggcgccacac ccaggtgatg   6900
caggggggaag ccaggctgta ttccggggtc aaagcaacac taactcacct ctctgctcat   6960
ttcagacagc ttgccttttt ctgagatgtc ctgttttgtg ttgctttttt tgttttgttt   7020
tctatcttgg tttccaccaa ggtgttagat ttctcctcct cctagccagg tggccctgtg   7080
aggccaacga gggcaccaga gcacacctgg gggagccacc aggctgtccc tggctggttg   7140
tctttggaac aaactgcttc tgtgcagatg gaatgaccaa cacatttcgt ccttaagaga   7200
gcagtggttc ctcaggttct gaggagagga aggtgtccag gcagcaccat ctctgtgcga   7260
atccccaggg taaaggcgtg gggcattggg tttgctcccc ttgctgctgc tccatccctg   7320
caggaggctc gcgctgaggc aggaccgtgc ggccatggct gctgcattca ttgagcacaa   7380
aggtgcagct gcagcagcag ctggagagca agagtcaccc agcctgtgcg ccagaatgca   7440
gaggctcctg acctcacagc cagtccctga tagaacacac gcaggagcag agtcccctcc   7500
cctccaggc tgccctctca acttctccct cacctcttc cctagggta gacagagatg   7560
taccaaacct tccggctgga aagcccagtg gccggcgccg aggctcgtgg cgtcacgccc   7620
cccccgccag ggctgtacct ccgtctccct ggtcctgctg ctcacaggac agacggctcg   7680
ctcccctctt ccagcagctg ctcttacagg cactgatgat ttcgctggga agtgtggcgg   7740
gcagctttgc ctaagcgtgg atggctcctc ggcaattcca gcctaagtga aggcgctcag   7800
gagcctcctg ctggaacgcg acccatctct cccaggaccc cggggatctt aaggtcattg   7860
agaaatactg ttgatcagg gttttgttct tccacactgt aggtgacccc ttggaataac   7920
ggcctctcct ctcgtgcaca tacctaccgg tttccacaac tggatttcta cagatcattc   7980
```

```
agctggttat aagggttttg tttaaactgt ccgagttact gatgtcattt tgttttttgtt   8040 ttatgtaggt agcttttaag tagaaaacac taacagtgta gtgcccatca tagcaaatgc   8100
ttcagaaaca cctcaataaa agagaaaact tggcttgtgt gatggtgcag tcactttact   8160
ggaccaaccc acccaccttg actataccaa ggcatcatct atccacagtt ctagcctaac   8220
ttcatgctga tttctctgcc tcttgatttt tctctgtgtg ttccaaataa tcttaagctg   8280
agttgtggca ttttccatgc aacctccttc tgccagcagc tcacactgct tgaagtcata   8340
tgaaccactg aggcacatca tggaattgat gtgagcatta agacgttctc ccacacagcc   8400
cttccctgag gcagcaggag ctggtgtgta ctggagacac tgttgaactt gatcaagacc   8460
cagaccaccc caggtctcct tcgtgggatg tcatgacgtt tgacatacct ttggaacgag   8520
cctcctcctt ggaagatgga agaccgtgtt cgtggccgac ctggcctctc ctggcctgtt   8580
tcttaagatg cggagtcaca tttcaatggt acgaaaagtg gcttcgtaaa atagaagagc   8640
agtcactgtg gaactaccaa atggcgagat gctcggtgca cattggggtg ctttgggata   8700
aaagatttat gagccaacta ttctctggca ccagattcta ggccagtttg ttccactgaa   8760
gcttttccca cagcagtcca cctctgcagg ctggcagccg aatggcttgc cagtggctct   8820
gtggcaagat cacactgaga tcgatgggtg agaaggctag gatgcttgtc tagtgttctt   8880
agctgtcacg ttggctcctt ccagggtggc cagacggtgt tggccactcc cttctaaaac   8940
acaggcgccc tcctggtgac agtgacccgc cgtggtatgc cttggcccat tccagcagtc   9000
ccagttatgc atttcaagtt tggggtttgt tcttttcgtt aatgttcctc tgtgttgtca   9060
gctgtcttca tttcctgggc taagcagcat tgggagatgt ggaccagaga tccactcctt   9120
aagaaccagt ggcgaaagac actttctttc ttcactctga agtagctggt ggtacaaatg   9180
agaacttcaa gagaggatgt tatttagact gaacctctgt tgccagagat gctgaagata   9240
cagaccttgg acaggtcaga gggtttcatt tttggccttc atcttagatg actggttgcg   9300
tcatttggag aagtgagtgc tccttgatgg tggaatgacc gggtggtggg tacagaacca   9360
ttgtcacagg gatcctggca cagagaagag ttacgagcag cagggtgcag ggcttggaag   9420
gaatgtgggc aaggttttga acttgattgt tcttgaagct atcagaccac atcgaggctc   9480
agcagtcatc cgtgggcatt tggttttcaac aaagaaacct aacatcctac tctgaaaact   9540
gatctcggag ttaaggcgaa ttgttcaaga acacaaaacta catcgcactc gtcagttgtc   9600
agttctgggg catgacttta gcgttttgtt tctgcgagaa cataacgatc actcattttt   9660
atgtcccacg tgtgtgtgtc cgcatctttc tggtcaacat tgtttttaact agtcactcat   9720 tagcgttttc aatagggctc ttaagtccag tagattacgg gtagtcagtt gacgaagatc   9780
tggtttacaa gaactaatta aatgtttcat tgcatttttg taagaacaga ataatttttat   9840 aaaatgtttg tagtttataa ttgccgaaaa taatttaaag acactttttt tttctctgtg   9900
tgtgcaaatg tgtgtttgtg atccattttt tttttttttt tttaggacac ctgtttacta   9960
gctagcttta caatatgcca aaaaaggatt tctccctgac cccatccgtg gttcaccctc  10020
tttccccccc atgcttttg ccctagttta taacaaagga atgatgatga tttaaaaagt  10080
agttctgtat cttcagtatc ttggtcttcc agaaccctct ggttgggaag gggatcattt  10140
tttactggtc atttcccttt ggagtgtagc tactttaaca gatggaaaga acctcattgg  10200
ccatggaaac agccgaggtg ttggagccca gcagtgcatg gcaccgttcg gcatctggct  10260
tgattggtct ggctgccgtc attgtcagca cagtgccatg gacatgggaa gacttgactg  10320
```

-continued

```
cacagccaat ggttttcatg atgattacag catacacagt gatcacataa acgatgacag      10380
ctatggggca cacaggccat ttgcttacat gcctcgtatc atgactgatt actgctttgt      10440
tagaacacag aagagaccct atttatttta aggcagaacc ccgaagatac gtatttccaa      10500
tacagaaaag aattttttaat aaaaactata acatacacaa aaattggttt taaagttgac     10560
tccacttcct ctaactccag tggattgttg gccatgtctc cccaactcca caatatctct      10620
atcatgggaa acacctgggg ttttttgcgct acataggaga aagatctgga aactatttgg     10680
gttttgtttt caacttttca tttggatgtt tggcgttgca cacacacatc caccggtgga      10740
agagacgccc ggtgaaaaca cctgtctgct ttctaagcca gtgaggttga ggtgagaggt      10800
ttgccagagt ttgtctacct ctgggtatcc ctttgtctgg gataaaaaaa atcaaaccag      10860
aaggcgggat ggaatggatg caccgcaaat aatgcatttt ctgagttttc ttgttaaaaa      10920 aaaattttt taagtaagaa aaaaaaggt aataacatgg ccaatttgtt acataaaatg       10980
actttctgtg tataaattat tcctaaaaaa tcctgtttat ataaaaaatc agtagatgaa      11040
aaaaatttca aaatgttttt gtatattctg ttgtaagaat ttattcctgt tattgcgata     11100
tactctggat tctttacata atggaaaaaa gaaactgtct attttgaatg gctgaagcta     11160
aggcaacgtt agtttctctt actctgcttt tttctagtaa agtactacat ggtttaagtt     11220
aaataaaata attctgtatg ca                                               11242
```

<210> SEQ ID NO 59
<211> LENGTH: 1367
<212> TYPE: PRT
<213> ORGANISM: Homo sapiens

<400> SEQUENCE: 59

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205
```

-continued

```
Asn Arg Cys Gln Lys Met Cys Pro Ser Thr Cys Gly Lys Arg Ala Cys
    210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                245                 250                 255
Ala Gly Val Cys Val Pro Ala Cys Pro Pro Asn Thr Tyr Arg Phe Glu
            260                 265                 270
Gly Trp Arg Cys Val Asp Arg Asp Phe Cys Ala Asn Ile Leu Ser Ala
        275                 280                 285
Glu Ser Ser Asp Ser Glu Gly Phe Val Ile His Asp Gly Glu Cys Met
    290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
    370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
        435                 440                 445
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Thr Trp His Arg Tyr
            500                 505                 510
Arg Pro Pro Asp Tyr Arg Asp Leu Ile Ser Phe Thr Val Tyr Tyr Lys
        515                 520                 525
Glu Ala Pro Phe Lys Asn Val Thr Glu Tyr Asp Gly Gln Asp Ala Cys
    530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
        595                 600                 605
Ser Val Pro Ser Ile Pro Leu Asp Val Leu Ser Ala Ser Asn Ser Ser
    610                 615                 620
Ser Gln Leu Ile Val Lys Trp Asn Pro Pro Ser Leu Pro Asn Gly Asn
```

-continued

```
            625                 630                 635                 640
Leu Ser Tyr Tyr Ile Val Arg Trp Gln Arg Gln Pro Gln Asp Gly Tyr
                    645                 650                 655
Leu Tyr Arg His Asn Tyr Cys Ser Lys Asp Lys Ile Pro Ile Arg Lys
                    660                 665                 670
Tyr Ala Asp Gly Thr Ile Asp Ile Glu Glu Val Thr Glu Asn Pro Lys
                    675                 680                 685
Thr Glu Val Cys Gly Gly Glu Lys Gly Pro Cys Cys Ala Cys Pro Lys
        690                 695                 700
Thr Glu Ala Glu Lys Gln Ala Glu Lys Glu Ala Glu Tyr Arg Lys
705                 710                 715                 720
Val Phe Glu Asn Phe Leu His Asn Ser Ile Phe Val Pro Arg Pro Glu
                    725                 730                 735
Arg Lys Arg Arg Asp Val Met Gln Val Ala Asn Thr Thr Met Ser Ser
                    740                 745                 750
Arg Ser Arg Asn Thr Thr Ala Ala Asp Thr Tyr Asn Ile Thr Asp Pro
            755                 760                 765
Glu Glu Leu Glu Thr Glu Tyr Pro Phe Phe Glu Ser Arg Val Asp Asn
    770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
                    805                 810                 815
Ala Ser Asn Phe Val Phe Ala Arg Thr Met Pro Ala Glu Gly Ala Asp
                820                 825                 830
Asp Ile Pro Gly Pro Val Thr Trp Glu Pro Arg Pro Glu Asn Ser Ile
            835                 840                 845
Phe Leu Lys Trp Pro Glu Pro Glu Asn Pro Asn Gly Leu Ile Leu Met
        850                 855                 860
Tyr Glu Ile Lys Tyr Gly Ser Gln Val Glu Asp Gln Arg Glu Cys Val
865                 870                 875                 880
Ser Arg Gln Glu Tyr Arg Lys Tyr Gly Gly Ala Lys Leu Asn Arg Leu
                    885                 890                 895
Asn Pro Gly Asn Tyr Thr Ala Arg Ile Gln Ala Thr Ser Leu Ser Gly
                900                 905                 910
Asn Gly Ser Trp Thr Asp Pro Val Phe Phe Tyr Val Gln Ala Lys Thr
            915                 920                 925
Gly Tyr Glu Asn Phe Ile His Leu Ile Ile Ala Leu Pro Val Ala Val
        930                 935                 940
Leu Leu Ile Val Gly Gly Leu Val Ile Met Leu Tyr Val Phe His Arg
945                 950                 955                 960
Lys Arg Asn Asn Ser Arg Leu Gly Asn Gly Val Leu Tyr Ala Ser Val
                    965                 970                 975
Asn Pro Glu Tyr Phe Ser Ala Ala Asp Val Tyr Val Pro Asp Glu Trp
                980                 985                 990
Glu Val Ala Arg Glu Lys Ile Thr Met Ser Arg Glu Leu Gly Gln Gly
            995                 1000                1005
Ser Phe Gly Met Val Tyr Glu Gly Val Ala Lys Gly Val Val Lys
    1010                1015                1020
Asp Glu Pro Glu Thr Arg Val Ala Ile Lys Thr Val Asn Glu Ala
    1025                1030                1035
Ala Ser Met Arg Glu Arg Ile Glu Phe Leu Asn Glu Ala Ser Val
    1040                1045                1050
```

```
Met Lys Glu Phe Asn Cys His His Val Val Arg Leu Leu Gly Val
1055                1060                1065

Val Ser Gln Gly Gln Pro Thr Leu Val Ile Met Glu Leu Met Thr
1070                1075                1080

Arg Gly Asp Leu Lys Ser Tyr Leu Arg Ser Leu Arg Pro Glu Met
1085                1090                1095

Glu Asn Asn Pro Val Leu Ala Pro Pro Ser Leu Ser Lys Met Ile
1100                1105                1110

Gln Met Ala Gly Glu Ile Ala Asp Gly Met Ala Tyr Leu Asn Ala
1115                1120                1125

Asn Lys Phe Val His Arg Asp Leu Ala Ala Arg Asn Cys Met Val
1130                1135                1140

Ala Glu Asp Phe Thr Val Lys Ile Gly Asp Phe Gly Met Thr Arg
1145                1150                1155

Asp Ile Tyr Glu Thr Asp Tyr Tyr Arg Lys Gly Gly Lys Gly Leu
1160                1165                1170

Leu Pro Val Arg Trp Met Ser Pro Glu Ser Leu Lys Asp Gly Val
1175                1180                1185

Phe Thr Thr Tyr Ser Asp Val Trp Ser Phe Gly Val Val Leu Trp
1190                1195                1200

Glu Ile Ala Thr Leu Ala Glu Gln Pro Tyr Gln Gly Leu Ser Asn
1205                1210                1215

Glu Gln Val Leu Arg Phe Val Met Glu Gly Gly Leu Leu Asp Lys
1220                1225                1230

Pro Asp Asn Cys Pro Asp Met Leu Phe Glu Leu Met Arg Met Cys
1235                1240                1245

Trp Gln Tyr Asn Pro Lys Met Arg Pro Ser Phe Leu Glu Ile Ile
1250                1255                1260

Ser Ser Ile Lys Glu Glu Met Glu Pro Gly Phe Arg Glu Val Ser
1265                1270                1275

Phe Tyr Tyr Ser Glu Glu Asn Lys Leu Pro Glu Pro Glu Glu Leu
1280                1285                1290

Asp Leu Glu Pro Glu Asn Met Glu Ser Val Pro Leu Asp Pro Ser
1295                1300                1305

Ala Ser Ser Ser Ser Leu Pro Leu Pro Asp Arg His Ser Gly His
1310                1315                1320

Lys Ala Glu Asn Gly Pro Gly Pro Gly Val Leu Val Leu Arg Ala
1325                1330                1335

Ser Phe Asp Glu Arg Gln Pro Tyr Ala His Met Asn Gly Gly Arg
1340                1345                1350

Lys Asn Glu Arg Ala Leu Pro Leu Pro Gln Ser Ser Thr Cys
1355                1360                1365

<210> SEQ ID NO 60
<211> LENGTH: 16142
<212> TYPE: DNA
<213> ORGANISM: Homo sapiens

<400> SEQUENCE: 60
gcccccgccg cccccgggcc ctgatggact gaatgaaggc tgcctacacc gcctatcgat    60
gcctcaccaa agacctagaa ggctgcgcca tgaacccgga gctgacaatg gaaagtctgg   120
gcactttgca cgggccggcc ggcggcggca gtggcggggg cggcggcggg ggcggcgggg   180
gcggcggcgg gggcccgggc catgagcagg agctgctggc cagccccagc ccccaccacg   240
```

```
cgggccgcgg cgccgctggc tcgctgcggg gccctccgcc gcctccaacc gcgcaccagg    300
agctgggcac ggcggcagcg gcggcagcgg cggcgtcgcg ctcggccatg gtcaccagca    360
tggcctcgat cctggacggc ggcgactacc ggcccgagct ctccatcccg ctgcaccacg    420
ccatgagcat gtcctgcgac tcgtctccgc ctggcatggg catgagcaac acctacacca    480
cgctgacacc gctccagccg ctgccaccca tctccaccgt gtctgacaag ttccaccacc    540
ctcacccgca ccaccatccg caccaccacc accaccacca ccaccagcgc ctgtccggca    600
acgtcagcgg cagcttcacc ctcatgcgcg acgagcgcgg gctcccggcc atgaacaacc    660
tctacagtcc ctacaaggag atgcccggca tgagccagag cctgtccccg ctggccgcca    720
cgccgctggg caacgggcta ggcggcctcc acaacgcgca gcagagtctg cccaactacg    780
gtccgccggg ccacgacaaa atgctcagcc caacttcga cgcgcaccac actgccatgc    840
tgacccgcgg tgagcaacac ctgtcccgcg gcctgggcac cccacctgcg gccatgatgt    900
cgcacctgaa cggcctgcac cacccggccc acactcagtc tcacgggccg gtgctggcac    960
ccagtcgcga gcggccaccc tcgtcctcat cgggctcgca ggtggccacg tcgggccagc   1020
tggaagaaat caacaccaaa gaggtggccc agcgcatcac agcggagctg aagcgctaca   1080
gtatccccca ggcgatcttt gcgcagaggg tgctgtgccg gtctcagggg actctctccg   1140
acctgctccg gaatccaaaa ccgtggagta aactcaaatc tggcagggag accttccgca   1200
ggatgtggaa gtggcttcag gagcccgagt ccagcgcat gtccgcctta cgcctggcag   1260
cgtgcaaacg caaagagcaa gaaccaaaca aagacaggaa caattcccag aagaagtccc   1320
gcctggtgtt cactgacctc aacgccgaa cactcttcgc catcttcaag gagaacaaac   1380
gcccgtcaaa ggagatgcag atcaccattt cccagcagct gggcctggag ctcacaaccg   1440
tcagcaactt cttcatgaac gcccggcgcc gcagcctgga aagtggcaa gacgatctga   1500 gcacaggggg ctcctcgtcc acctccagca cgtgtaccaa agcatgatgg aaggactctc   1560
acttgggcac aagtcacctc caaatgagga caacagatac caaaagaaaa caaggaaaa   1620 agacaccgga ttcctagctg gggccttca ctggtgattt gaaagcacaa ttctcttgca   1680
aagaaactta tattctagct gtaatcatag gccaggtgtt cttcttttgt ttttaatggc   1740
tatggagtcc aagtgcaagc tgaaaaatta atctcttaga accagacact gttctctgag   1800
catgctaagc atcccagaaa cccaaatggg gccttcctgg agcgagttaa ttccagtatg   1860
gtgtcaacca agctcgggat tgcttaaaat atcatccatc ccacttcagg tcctgtcagc   1920
ttcttgcagt cagagttcct atgagtaaca ataggagttt ggcctatgta aggactctga   1980
gtttaggctt ccaagataca acaataagag aagaatctag caacgagaat gacctcattt   2040
gctttccaca tgcttagcct cattataccag tgttatgtcc aagttcacag ccacaacatc   2100
agaatggtaa ttactgagca caagttttaa atatggacgt taaaaaaaaa aatccaagga   2160
cctgtttttc caacccagac atcttttcat tgaatgattt agaaagcttt aagttgatcc   2220
agcttacaat ttttttttc tttacctcct ggaaatctca tatggtcttg gatccgtcaa   2280
aaaaaccagt cagttcactt gcgctcaaag tatcaagcac aacaaagata aacagaagtg   2340
aggaaggttc tgggttcact acatctggat tttcaagaca cctattgtga agtcattagg   2400
gaattgatga gaatatggct tcaagcacat tttgcagttt gctacaaatt ctgttgtaca   2460
taatgcagac gcacactcag gaggccaatt taactgttaa cagtgcatgg agcgaatgca   2520
gcattttaaa agatctaggt tttttaggt cattaatgtg tccttggttg atcagtcatc   2580
```

```
tggtccctcc tactgtgtgt tatgaccacc acgtaatcca ttctcgctct ttctgatttg    2640 gggttttttcc tcatccatcc cattagtagg gatgttttct gtgttttcta gcaagaaaaa    2700
aaaatcaatc aatcaaacct gcatacatgt tactcatgac tgtcatctag tcctaaatct    2760
cttctgttgt tgaatcatcc ttgcaaaaca gctgaataca tctggagaaa acacagcaca    2820
ccaaagaagc agaatactgc aaaccaaaga catttatgac ttgtcatttt ctagcctaaa    2880
aatactgtga ttacttttag aaatcagaaa acctctgcaa ctccgaatgg cattcagctc    2940
ttgcatttgg cgcatcatcg ggctgagcgg accagctaca ccaaggacat tagccaagcc    3000
acccagaggg gtggctttgc cacaccagtt gtcaccttcc catagcaagt ggaagagcgc    3060
ccacagaact ctgggagatt gcaaaggtca caatgtgcat atttaccagt gaatggcccc    3120 gggtgggggcc acgtggggt gttcaaagca agccaaacgc tgcaatcatt ctttacagac    3180
acttgagact gactttttta tgaattactt agtcgaaacc aaagaaactt tttctgcacc    3240
tacttctgca acaaacaaaa ctgtcccatt aaaatgaata aataaatccg taaatcaatg    3300
gaaatcacca ccaataagaa ggaagcacgc cagaaaataa acgaaaacaa aaacagggag    3360
acacactgtg ttcaaacaga cctcttggga cattttttgg aagcagattt taaagaaagg    3420
gttgagacaa agatagaaat aaggaagagc ctcagtggct gctgcttcat ttgacaactc    3480
acacggtaat cttaaagctg aagattgtct ttaatttgtg cctatgcagt ttttcaaaag    3540
aacacggaac agagcaacag aaacctcaac agctacaata ccaaagatga ggatttctca    3600 cacctttttgt ttcagttcat tatctcctct tgcctggcta aaatactaat agcgccattg    3660
aactgtataa aggtaatcaa ttatgttttct ctgagcaaca aaaggaaagg gccatttatt    3720
tgattttatt gtttcatttc aattttgtct tatggttttt tgccccaaca tggaatctct    3780
caaaagtttc catggactcc aagtttaaga tgttgggata ttgaacagtt ctctctgctc    3840
agcagagggt agggaataac attatcactt gaatgttctt tgcttaaccc ttagacttgg    3900
ttccttctat gttcagagtc tcatcatcag gggaaggaaa gggagtgagg gtcagggata    3960
ggggtcttgg tgatgcatcc tctcccgagc cacagaacca aagagtttat agaggaattt    4020
acagcctcgt tttcatgtga ttgctacatc ctaacagggc ttcatttggg ggtgggggga    4080
aacatgtaaa aataattgcc agtttctact tttctattag cttttttaaaa atcagctgta    4140 aagttgcatt tctaaagaaa gatatatata atatataaaa tacatatata gatcaacttg    4200
acattggtga taaccaaaat tattgctgtc caaattcatg tcttgttttg gtccagtgct    4260
tcatttgcta agtattcggt tcagaatttt tctcatttct catgccattc cagagttaat    4320
ttgccactgt ggatgatttg aagtattcag atctctatgg aagtttctgg gacaggttta    4380
aagtcaagat caagcatttt agcatttaac ctgttgataa atggatccat ggtgtacatg    4440
agttttattt gtattcggag tcatctctat tctatccctc agcctcgatt aaggtggtga    4500
gtgaagtgca tccaacagac tcggcccaga actgggtcct gacagtgggg tgctcatctt    4560
ctgtaactgt tgggaaggct cggtggtcca ttttcaccag ttaaagaata tgaggccagc    4620
ccagaaatct gttctccagg agctgccctg tcccatctgg gtgtgccaga cccctcagt     4680 gagcaggtcc accaaaggga cttctcacag gggaagccca actcctgttg caatgggttg    4740
atagatttcc tcagggtggt aattaccaat tcgtatttg acaagcctat gtgcaaccac     4800
agctggcact ggggtgggca gtggtgttgg gtgggatggg ggagagtgtc tcaatcctga    4860
agagaaaata taaagcaggt tttggggaga cttctggagt cctgcccta gagagcccca     4920 ttgttgttct ttgtgccccc tcctcattcc ccctatgtgg gtctccctat gcaggagctg    4980
```

```
tgagagaatg tgactctcca caattttat aattcatcct tcctaggaga ttgttcattg    5040
gctcttccct tgtgtccctt tgtcccttgc tcatactcca tgtttccttt gtcaaaggac    5100
taagaaaaga gcatatttca gcagaggagt gttcccatgt gggttgattt caacttgggt    5160
atttctaaaa gagtccttgt gacatgtgtc cagtggaaat ggttgctctt ttccagactg    5220
gattgaggaa tggagcctgt ttgatttggt tagtgattct ttgacatact aatctcagcg    5280
tttgggtctc cagcatcctc tgaagatgtc tagactagta gaggctgcct ttgtgacctg    5340
acattacaac attggtcaaa ccagtcctct gataatcaga agaacatgtc ataattgttt    5400
aaaaaaaaaa aaaaggcaag aatttctctc caaggagctt taataaatgt ctcattccag    5460
ataatgtcat accagagaaa agtgcttgct tttagaaaat tatttacata catatataaa    5520
tatatatgtg tatctataca gttatgtatc aaaattttaa gccctgcaga atttcaattt    5580
gttagaaatc taacagaaaa aaatttctat attgaaaggt aatagaattt aacccagtga    5640
gtttactcaa ggattttaa atttaagtta ataatttcag agaaaataac catttgggtg    5700
tggttatagt ttagtatcca ttacctcaat ccaaggaaaa ttccaggcat tcctcaacca    5760
tcaggaaaag gtacagtgtg aaggaacagt tctcagccaa atttcacatt cttgaggcaa    5820
cagaaatcaa aacactcaga gccattgagt ggaaaaacaa tttactttat tcctttacac    5880
aaataggctt gcattgtttt tgttttaatg tgattttggt actagggata taattatttc    5940
attccaggaa ataataaaaa aaaacagaca gagccaatac atttctttt ttaaaggaaa    6000 cagcaacaac aataaaaact cagcaccaat atttaaaagc ttttccaaaa tgtaaaagaa    6060
gtgtttagct tgcaccatgc ataaaggtgc aggctagttg aaccaggaag catggcactt    6120
cctctggaga aatccagaaa gagttgcttc taagctccct tttccccctg caggctcttg    6180
gcaattgtag gctttagcaa atccagaata attttcaatt caagctaaaa taaaatcaac    6240
atttggaatg taaatctgat acacacacac ttttctaagt caaacaacat atttcaaaac    6300
caaaaataaa taccttttag ataatcagtt attttctttg tctatactgg gcacccacct    6360
actagtgcca gtaaattcaa gttgaacaga ttttttaaaat cactattatc tgggtatggg    6420
ggaaacttcc ccacttttga aaatgttggt agaattatag gaatgtctgt ttgattatca    6480
ttaccaaagt gtcatgacag tatgcctttg tagtgaactc ggattttcag gagtttgaat    6540
agttggatat tttaaaatct aagaagaaaa ggcctgtttc caatgttgtt gaagaataat    6600
gaactctatt aaaagtggaa gaaaagata atacatgtgg tcaaggttga ccacaaggcc    6660
caggcacaac taccttggcg ataatcttct agattcgtaa caggttagag ctgacttttt    6720 gttttttgttg ttgctgatgc tgtgtgattc agacttctca gcctaaccag gaagagtaag    6780
tggaaatggt agatgaagaa ggggtagagc tggtgtatct ataactttct gatatttgtc    6840
tgccaaactt gatatattag taatttttt atctttagct aagatcaagt caccccctgaa    6900 acaacaggag attctagttt taaaataagg ccacaaaaat ccttacggaa tgaagaatgg    6960
caccccagtt ggttgtataa gtctcataag ataatgatgt tgattttaaa tatggatgtc    7020
tcaatgcctg ttttctatca atgatttgtt tgtttccaag gtcggggagg gaaagagggg    7080
agggtttatc tgttttagaa agtctcagaa tactataaa atacagaagt agttattaaa    7140
atatatagga cctcacatag gtagatacag aacttaccat tgaggctgat gggctgttgt    7200
gtgaatcaca caggacctta aatgaggctc attattctca cacaccaaaa tgactctgac    7260
agcctgaagc agttattgct agagcccaag ctttccttgg aggttttgga gttaggttga    7320
```

-continued

```
ttggaagtaa ccagctaata ccttttctag tggagaaaaa gacattgcta ccagcttgtt    7380
catcccatag aagtcttcca ctctgctcca tttttagcag caagcatttc atgtagcata    7440
aaccttggca gataagtgtg cctaaggttt atacagtctg tccgcttgga tgtatacaaa    7500
tttagataca tattttaaca tgtgttctca tagatgactt tataacaaca cacattacct    7560
ataggtgtct agactgtgta catacaagtg tgtacagaca agcttcatac gtatatactg    7620
taatccgtta caacaaataa attttaaatc atcgtttaac atgtatgtgg tacttctaca    7680
gtgtacattg ttttcattat ttattgtaac attgaaaacc acagtgcagg aaaacaaaa     7740
gtatcccagc atcttcatcc tgtacacttg gaattaattt catttgggca tatccaagat    7800
aaactcaact ttcaagaaat cttgtatatt atttaatcat ctgtgttagg atgacaccta    7860
tgattgatga cttcggttga atagctttat tctggatttt tcataactaa agctaaatcc    7920
aaagacctga aaaggacaa aagaaaaaa aaaaaagaa aaacaaaga aaagaagaa          7980
aaaataataa agtcaagcgc aaactgatgg ggagacagtg ggctctggtt tccaggattg    8040
agacaatggt actgcggtct tggggagact gcgttagcta gtggggagtg gtgatttttt    8100
tcatgcttgt cacatctaaa tggtctttaa catgagaaag ttttagaggt tataatttcc    8160
tgctttgttt ttatttagac tatcaaatga agttatacat gttgtcagtc aaaaaatgaa    8220
gacaccctct gccccacccc acagaatgct ttttatcttg tctctttggg ttatgaccca    8280
acaagctaag taccattaat gtaattaact tatttaaatt agttcctagt acataaatgt    8340
ataggatttg ggtaattatt taatcatcct tccttagttt gattctactc cttgtactta    8400
tttatcaaaa cctagaccaa tggtgcatca gagatgcaaa attctacttg gaatactctt    8460
gaagtttagt ttgctttata aagcagtgaa attctgttac agacagggaa gaaatacagg    8520
ttacaaaaag agaatttggg atattcttcc ctcttaaatt aacttttaaa atagtctaag    8580
taacaatttt taaattattt aacttaagtt cgcagcccca cctggtacca ggcgaacttc    8640
acctcttaat tattgtggcc ctcggagcct tcatattgta acttatttat ttaacttatt    8700
cagcatctgt gaaaggtgca ctgtatagtt tatatttta atttaaaaca acagagagca    8760
ctgcagtttg tttgctgtca gaacaacaga gcaaattttg tggacaagca atgactattc    8820
agcctgaacc tgtgcattca gaaaacataa gctgagaccc tgcttcacca gcctggattt    8880
cggggcttct atacagaaac tggaaaaata aatttaaaa aaatcgtaaa caaaagaga     8940
gaaaccctta cactagctgc ttccaagaat gaactctgtg tgtatgtaaa gcaacaaaac    9000
aaaaaaggaa aaaacaaaa agcagaaaaa agaaaaaaa aatgaaaaac tttctatttc     9060
tagtgagaac caaagaaggc tacctcactg acttttccca tttgtaattt taatcgtgtt    9120
gatgacacca aagataccaa agatttcttt ctctgtgcgg tctgcatttt gcttgtgctc    9180
ttttataatt tgaacgattt tctctgacat atggtatgta cagccacagc tcagataccc    9240
caaagaaata attatctatg cgacggcggc tgctaatttg gaaagggata ttttctgtgt    9300
ttctcttata tgtttgctgt ctgctcgaca tgttcaagat gcgagttcag atgctgctgt    9360
aattggattc cttaaattct gattacaaat tgaggaagga aactggttgg aaatggcctt    9420
cagtcctagc catggcctct atccccgctg ggacctgtca cagtaaagac tgccaattac    9480
tgaaccacag aagctctgac cattgagtag ttgagctgga agagacctta ggaatcattt    9540
agtccaagcc ccggtggccc agaggaatga aatagttatc caaatcaaat aactcttgag    9600
agtgaaagcc cacacatgcc tcctggttcc tgccccagtc ctccgcttat tgtacagtgc    9660
tacctctgca tgagagcggt cccacattga caaataggat ggtggcaatc ctttagcaat    9720
```

```
gagcagggac tggggtttat ctcttaacat tttcagctgt aaaattagtc acaagcattt    9780
tcagtgtccc attagtacat agtcacatat ggtcggttgc ttcgtgaagg tggcctgtct    9840
tgaaatacta gggctcatac gggattttg ccctaggaaa acatgttga tcccaatgat     9900 gtgatcactt ttgaaccttt ccattacaaa gcattgtata gataactttt taattcagta    9960
ggaggagaaa gttcattctt ggcctgttgg ctttgattat tatgggtact ttaaagtcag   10020
tatttatcaa gaaagggaac ttgaccacca ttggcacatg tgacatttaa gctcttcagc   10080
cttttccttt ttagttgtag gtgtttacat ttcatttcta agccaactct gtatttatga   10140
gagaagttta agccttacat catttgatac taaagggtta tttgtggtaa atgaaaaatg   10200
accccaaaat tacagaggaa tatgccagtt taagaaatgg ctacttaaag ttgcttctct   10260
ctttccttct tactcatgaa attaattggt cttcttcaag tttctttaga ttccattaaa   10320
tgattaaatc actattaaga gccattcatc aacgtgattt gtgtgttagc caatgaatct   10380
gtctcagctt ttgaccaaat gggttttaga caaatgcaaa gatctgcctc tagtccatat   10440 ggctctttt gagtgctagt attttgcatt tcacataatg tagttatttt gagcttttaa    10500
agagagcatt tagacaaaga agcaaagaga ggaagggacc aatcaactca tcagttccat   10560
gcatcaacaa agcatagcta gtagaggaat ataaatgaca gattgacaaa ctgtaggaaa   10620
cactgttact ctcttctga agttttcaag caccatccta tgtgaaagtt ccctcctgtc     10680
caaacaagct caaggcccat cttctcccta tacaaggcaa acctgtaagg ccttccttcc   10740
aaagagtaca ttgctttggt tttcttccta aattcctatt ggaattagaa ctctcagaat   10800
ccctgggaga cagagcaaag atgacttaat tcattgagca gcagagctcc ctataagtga   10860
acatcacctt ccccatcttt cctactgcca cacccatacg agagaggatc tagaaagagc   10920
gatggcagcc tgaacacaga aaacatcccc acttggcaga cctctcctca gcaatccccc   10980
cagcctcatg cttcacttgc aaagtgtgac ataaccacgg gacgagtgcc ttgcttgaac   11040
caaagcaacg atttagccag tctggacctc tctgtgcttt ttttaattct tcctgtgaat   11100
acctcagctt caactgggcc tccatacagt cagttggtgg gcttattgta ctgtggtgct   11160
ttgcaatgca accctgcaaa gaacaagatt tgtactaata ccaaaggttc tttctctatg   11220
tctcctcctc tgcctccctc gttcttccct tttttctagt tcttcacggt tccaaagctt   11280
tactatgaac ctgggcatgt tggcaatgca gaccgcgcaa ttccttaccg aattttctca   11340
gatatacctc atagacaata gtgtttagag taatgttatt atagcgtatg taataaatta   11400
ttcactgttt cttttggtaa ctgtgattta aaaaagaaa aagaaaaaa aagctttata    11460 cgttttaggt tgtgctttg taatagatga aaaaggtgc gcttaaaaag aaaatgtatg    11520 ttttttccc cctttggatt ttatttatgc tggattgggg aaagttgcag aatgagccca   11580
aagtttacag tttcatattt tgctgaagaa acaatctgtg ttcatttgct ctgttgaaaa   11640
gaataattat tttctacatt tgtgccactt ggtctgaaca attaattgtt ccgtgttaac   11700
agtgtagtat tatgattagc aactgccaat cagtgctata attttatgca tgaggctaaa   11760
aatttagcag tgtgatgcat tgtggtctta atagcaacat ttttcatttt gaactagatc   11820 ttccccttg gttcaatgga ctttatttat gcatgggcgc ctattgtttg ttagcagttg   11880
tggaacagtt gtgtatacat taaactgtga aaatgtacac agttcagcct cagacggtgg   11940
taatattggt tttattggga gatgtgtcac ctcgaaaata ccctttacat ctgttgggat   12000
ctgaaaatga gtcacattga attgggttcc agctttataa tgagaaacgt tattcctaat   12060
```

```
tttgagtta gccaatttgc attccacaaa ttgggatcct cataacccaa atatatcacc   12120
gtatgtgaga gggatttgaa agcgagtatt gaaaaactca cctttgcata tttaatttcc   12180
accaaaagga gttatttggg ctttatgctc atgaacttag acctaactgg ccatgtatat   12240
gtagatgcaa attcatctag ctgtggccct ctttgatctc tgcttgggaa tggctatttt   12300
tgactatgcg tggtttcttc tcgtattttg tgatcaggtc agctcccagt agaaactcaa   12360
atggcatcaa tattactaac tcttctctgc ccacttctct tttgtccact ctccagaca   12420 ttcccaccaa ctgttccagt gatttgggca aaaatacgca gccatttccc aaaacttcac   12480
atgtgcagct atcatggctg tccctcccta gacttggagg tgactctcac ttaattttta   12540
cctgcccaac aatgttccat ctaccatcta aaaggtaata taagaagaag ttttgaaacc   12600
cactttagga aaaccatctt ctttaaatcc ttcaattatc tgaggcctct atatgtcaaa   12660
actatttttc agttgcaggg gattgggcaa acttgttctt tcttatactt gggttcaaag   12720
acccattctc cagtttcata tttcccaaac caaaatgctt gacataaagc caaatcaact   12780
gccaagcaca ctttattttg cataggagta tgcagcctag gaaccttggg ttgaaaagca   12840
gcagtctgct atgcaaaata ttggaaatca ctgacagtgt agcattcata ttatctgtca   12900
atgagggtat attgggaacg tgctctcgtg aataataaaa agcaacatat ttttatttgg   12960
cctataaaat taggttgtgg taatgtaaac tttgatatat agtctttta tttttctctt   13020 attaatctgc caaagatggg aacagataca agaattttc aaattggctt ttgtaagaca   13080
attgatgatt gtaatagtgt ttaatcttcc agaaagcttt atatgttgtt ccacaataaa   13140
attgatattt gtttcagcaa agttttcctg acactcacaa acccacaaac tgttcctctt   13200
aatgcagata ttgtagaatc tacaaagttc aaatccattt ttgatccaaa gaaagtagag   13260
gagtatttga gacatgagtg taccccagccc tttttttaat cacaggcaat gcatgggtct   13320
ggctggttac acttttgccaa gaagacttgt cttatgaaac ccaaggtata ttttgttatg   13380
ccattttatg tcctttttctt ttaacattgt ggaaagtggt atgttgaatc aagtgtaagc   13440
tgagttttcc agacaactga agtagctaca tcatgaatgt tattttgtta ttaaagggtt   13500
tttactcagt gctttgtgcc aatggatgtc cttttccttg gagacacata actacaaaat   13560
tacctcagct tggcctggtt ttctctcctg ccctcttggg gaaacatggg cctggcctgg   13620
gaaaaggcag gtcatgggct ggaaggtagg ttttggtact aggaagaaat ctctgtatct   13680
gtcagcttta aagagaactg ggccaaaaat ctctaacctc actctctctg gactccaaca   13740
cttccctgca atcctttggt cttgagcatg tgccagcatg aaggcagact ccagttcata   13800
catgaaaggc aagaaaaaga aaatagtaac cttgaatctt ctgtgggcca ccaggcactc   13860
acctttcccc accttgcaca ctatccagtc aaggctattg cagcccatct ggtggcttta   13920
catgggacat taccaaaggc ttcttcctcc atcctggggt tgcaaaggat ccaggtcccc   13980
tccatccagt ggggctcttc cacatcagaa gtcccctcc caccatcctc tgcatcctgt   14040
ttagctatcc catctatacc ttttggagat gattatttag aaaacaaaga aaggtatgga   14100
atggggtttc ctattgtttg ctaggttata ttttagcaat tctcaattct ttgatctgga   14160
aaaatacaag agggaaaagg agacccccact atctccctgt gctttgctcc catctcaggg   14220 ggcagggca gtgcacattg cctatgctgt tgatctgtct tgggcgacag gctgaatcac   14280
agctattgcc ccagccaaaa acatggccca tcaatgccta ctttatctct gcttgaaaat   14340
cctattcaaa aagttgtaga gtttgaggtt tttatccccc catatccttt gctttggtcc   14400
agtttggcct ttagcataag agtcagcttt atctctagga aagttttttc agattatgac   14460
```

-continued

```
aaggaacctg ccacctggga agaaaagagt ccgaagacta gcaatcggat aggtagtcat  14520
accattaaca gatacttcct tgaaggtaga atattatttc ctttctttac agttttgtgt  14580
tacacaagtc caagtggtgc cagcaaactt cttaccgtga atgttgtaa  acacctggc   14640
atactgaaat ttctgaaaca aaaacacaag ctccacattg ataacttgat aaataaccac  14700
taaagtttag atgcagggac tgagatgata caggcaaaat cttggtgttg gtttctcttt  14760
taattcgtat cttcgatcac ctaacctttc tcaatccaag agcagttcag tcttttctcc  14820
ccaagtctag gatgccaaag agcatcatag gaaagataa  ttagggattg accagcattt  14880
caattagttc tcttcttcat ctttgcattt ctcaaaagtg ttctcctgga ccagagggaa  14940
agagctggtc cattttttt  cattctttct attcaaattt ttccacccag acaatacttt  15000
attaacacag atactgtaga tccttccttg gtcagtgaat tattacaaga ggagctatcc  15060
ttccaccaaa gtgagtgaaa acaagttcca gtatctttc  ttccatccag ttttgttctc  15120
agaatccaag tcagtcctgg gtctttctc  actttagacc ctggcctcag atgtgtttat  15180
tcttgctatt taaaaatacc tttaaatttc acatgctggc ctgcagaact tgcatccttt  15240
gttctatact gttgactgct tgatggtatt gaaaggtgac tataatgagg gaagaaagga  15300
ggaggtaaag agagaagaat tgtcccaga  tctgtttaaa gtttcaaaat ttaaaagggg  15360
acccattaaa ttatgggaaa atggctatag agtgtgagcc tccgttgacc atatgctcaa  15420
agaccgtact ctgccacctg ccttccaggt agctattcta gaaactcagt cctttgtgga  15480
aacccaacta ccttttaaaa gtctctttcc agattccaaa aggacaagag atcagagagt  15540
cacatatacg cctcttgttt tattttcttg ctttcacggg tattattgcc aagaaaatcg  15600
tagggaaaaa ctttaaactt ttcttttcag ttgatcccttt tgacatcacc tctcatgttt  15660
aaaatcagga aaacacaccc ctaaaatttg cactctcttc cgttttgaaa aagaaaaccc  15720
acacacaaat gcacactatt accgtctttc accctgcgct atatttccaa agtgtattat  15780
aatccagata ttgccccatc tcaaacatgt taagtcagac tgtgctgaaa gactttccag  15840
ggacggtcaa cagggtatat gttcagtggc tgccctgaaa tcctggtggg gatgaggatc  15900
acgcttcatc atcaagggga tgcccatccc ctgataagct cccagtcctt ttggaagatt  15960
tctttgaatg ttaattgcat tttcagtttt gctcatttcc caccccaatg ttttgtctgc  16020
aacatcgctt acactggatt cttttctattt ttattcctat cattaaatgg tagtgctgta  16080
aattctgcaa ttaatgttaa ataaactgct ttaattcatt gaaaaaaaaa aaaaaaaaaa  16140
aa                                                                 16142
```

<210> SEQ ID NO 61
<211> LENGTH: 504
<212> TYPE: PRT
<213> ORGANISM: Homo sapiens

<400> SEQUENCE: 61

```
Met Lys Ala Ala Tyr Thr Ala Tyr Arg Cys Leu Thr Lys Asp Leu Glu
 1               5                  10                  15

Gly Cys Ala Met Asn Pro Glu Leu Thr Met Glu Ser Leu Gly Thr Leu
             20                  25                  30

His Gly Pro Ala Gly Gly Ser Gly Gly Gly Gly Gly Gly Gly Gly Gly
         35                  40                  45

Gly Gly Gly Gly Gly Gly Pro Gly His Glu Gln Glu Leu Leu Ala Ser
     50                  55                  60
```

-continued

```
Pro Ser Pro His His Ala Gly Arg Gly Ala Ala Gly Ser Leu Arg Gly
 65                  70                  75                  80

Pro Pro Pro Pro Pro Thr Ala His Gln Glu Leu Gly Thr Ala Ala Ala
                 85                  90                  95

Ala Ala Ala Ala Ala Ser Arg Ser Ala Met Val Thr Ser Met Ala Ser
            100                 105                 110

Ile Leu Asp Gly Gly Asp Tyr Arg Pro Glu Leu Ser Ile Pro Leu His
            115                 120                 125

His Ala Met Ser Met Ser Cys Asp Ser Ser Pro Pro Gly Met Gly Met
        130                 135                 140

Ser Asn Thr Tyr Thr Thr Leu Thr Pro Leu Gln Pro Leu Pro Pro Ile
145                 150                 155                 160

Ser Thr Val Ser Asp Lys Phe His His Pro His Pro His His Pro
                165                 170                 175

His His His His His His His Gln Arg Leu Ser Gly Asn Val Ser
            180                 185                 190

Gly Ser Phe Thr Leu Met Arg Asp Glu Arg Gly Leu Pro Ala Met Asn
        195                 200                 205

Asn Leu Tyr Ser Pro Tyr Lys Glu Met Pro Gly Met Ser Gln Ser Leu
        210                 215                 220

Ser Pro Leu Ala Ala Thr Pro Leu Gly Asn Gly Leu Gly Gly Leu His
225                 230                 235                 240

Asn Ala Gln Gln Ser Leu Pro Asn Tyr Gly Pro Pro Gly His Asp Lys
                245                 250                 255

Met Leu Ser Pro Asn Phe Asp Ala His His Thr Ala Met Leu Thr Arg
            260                 265                 270

Gly Glu Gln His Leu Ser Arg Gly Leu Gly Thr Pro Pro Ala Ala Met
        275                 280                 285

Met Ser His Leu Asn Gly Leu His His Pro Gly His Thr Gln Ser His
        290                 295                 300

Gly Pro Val Leu Ala Pro Ser Arg Glu Arg Pro Pro Ser Ser Ser Ser
305                 310                 315                 320

Gly Ser Gln Val Ala Thr Ser Gly Gln Leu Glu Glu Ile Asn Thr Lys
                325                 330                 335

Glu Val Ala Gln Arg Ile Thr Ala Glu Leu Lys Arg Tyr Ser Ile Pro
            340                 345                 350

Gln Ala Ile Phe Ala Gln Arg Val Leu Cys Arg Ser Gln Gly Thr Leu
        355                 360                 365

Ser Asp Leu Leu Arg Asn Pro Lys Pro Trp Ser Lys Leu Lys Ser Gly
        370                 375                 380

Arg Glu Thr Phe Arg Arg Met Trp Lys Trp Leu Gln Glu Pro Glu Phe
385                 390                 395                 400

Gln Arg Met Ser Ala Leu Arg Leu Ala Ala Cys Lys Arg Lys Glu Gln
                405                 410                 415

Glu Pro Asn Lys Asp Arg Asn Asn Ser Gln Lys Lys Ser Arg Leu Val
            420                 425                 430

Phe Thr Asp Leu Gln Arg Arg Thr Leu Phe Ala Ile Phe Lys Glu Asn
        435                 440                 445

Lys Arg Pro Ser Lys Glu Met Gln Ile Thr Ile Ser Gln Gln Leu Gly
        450                 455                 460
```

```
-continued

Leu Glu Leu Thr Thr Val Ser Asn Phe Phe Met Asn Ala Arg Arg Arg
465                 470                 475                 480

Ser Leu Glu Lys Trp Gln Asp Asp Leu Ser Thr Gly Gly Ser Ser Ser
                485                 490                 495

Thr Ser Ser Thr Cys Thr Lys Ala
            500
```